United States Patent
Yoder et al.

(10) Patent No.: US 10,563,175 B2
(45) Date of Patent: Feb. 18, 2020

(54) METHOD FOR GENERATING ENDOTHELIAL COLONY FORMING CELL-LIKE CELLS

(71) Applicant: Indiana University Research and Technology Corporation, Indianapolis, IN (US)

(72) Inventors: Mervin Yoder, Indianapolis, IN (US); Nutan Prasain, Greenwood, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 431 days.

(21) Appl. No.: 15/124,280

(22) PCT Filed: Mar. 11, 2015

(86) PCT No.: PCT/US2015/020008
§ 371 (c)(1),
(2) Date: Sep. 7, 2016

(87) PCT Pub. No.: WO2015/138634
PCT Pub. Date: Sep. 17, 2015

(65) Prior Publication Data
US 2017/0022476 A1    Jan. 26, 2017

Related U.S. Application Data

(60) Provisional application No. 61/951,103, filed on Mar. 11, 2014.

(51) Int. Cl.
   *C12N 5/071*    (2010.01)
   *A61K 35/44*    (2015.01)
   *G01N 33/50*    (2006.01)

(52) U.S. Cl.
   CPC ............ *C12N 5/069* (2013.01); *A61K 35/44* (2013.01); *G01N 33/5064* (2013.01); *C12N 2501/115* (2013.01); *C12N 2501/155* (2013.01); *C12N 2501/16* (2013.01); *C12N 2501/165* (2013.01); *C12N 2506/02* (2013.01); *C12N 2506/03* (2013.01); *C12N 2506/45* (2013.01)

(58) Field of Classification Search
   CPC .......... C12N 2506/03; C12N 2501/115; C12N 2501/155; C12N 2501/165; C12N 2501/16; C12N 2506/45
   See application file for complete search history.

(56) References Cited

U.S. PATENT DOCUMENTS

2008/0025956 A1    1/2008   Yoder et al.
2012/0301443 A1*  11/2012   Raffi ............... C12N 5/069
                                                        424/93.7

OTHER PUBLICATIONS

R. Ian Freshney, "Subculture and Cell Lines." In: Culture of Animal Cell: A Manual of Basic Technique and Specialized Applications. (Hoboken, NJ, John Wiley & Sons, Inc., 2010), pp. 187-206. QH585.2.F74 2010. (Year: 2010).*
International Search Report in PCT/US2015/20008, dated Jun. 8, 2015, 3 pages.
Written Opinion of the International Searching Authority in PCT/US2015/20008, dated Jun. 8, 2015, 5 pages.
Meador, J.L., Derivation of Endothelial Colony Forming Cells from Human Cord Blood and Embryonic Stem Cells, Indiana University, Aug. 2013, 81 pages.
Extended European Search Report issued by the European Patent Office, Munich, Germany, dated Jul. 6, 2017, for European Patent Application No. 15761667.3; 11 pages.
White, Mark P. et al., "Limited Gene Expression Variation in Human Embryonic Stem Cell and Induced Pluripotent Stem Cell-Derived Endothehal Cells", *Stem Cells*, vol. 31, No. 1, Jan. 2013 (first published Dec. 19, 2012), pp. 92-103, XP055383022, ISSN: 1066-5099, DOI: 10.1002/stem.1267.
Rufaihah, Abdul Jalil et al., "Original Article Human induced pluripotent stem cell-derived endothelial cells exhibit functional heterogeneity", *American Journal of Translational Research*, vol. 5, No. 1, Jan. 2013, pp. 21-35, XP055270661.
Prasain, Nutan et al., "Differentiation of human pluripotent stem cells to cells similar to cord-blood endothelial colony-forming cells", *Nature Biotechnology*, vol. 32, No. 11, Oct. 12, 2014, pp. 1151-1157, XP055383069, ISSN: 1087-0156, DOI: 10.1038/nbt.3048.
Chiang, Pro-Min, et al., "Differentiation of an embryonic stem cell to hemogenic endothelium by defined factors: essential role of bone morphogenetic protein 4", *Development*, vol. 138, No. 13, Jul. 1, 2011, pp. 2833-2843, XP055383059, ISSN: 0950-4991, DOI: 10.1242/dev.061440.
Pearson, Stella, et al., "The stepwise specification of embryonic stem cells to hematopoietic fate is driven by sequential exposure to Bmp4, activin A, bFGF and VEGF"*Development*, Published by The Company of Biologists Ltd., GB., vol. 135, No. 8, Apr. 1, 2008, pp. 1525-1535, XP008092701, ISSN: 0950-1991, DOI: 10.1242/DEV.011767.

(Continued)

*Primary Examiner* — Kara D Johnson
(74) *Attorney, Agent, or Firm* — Faegre Baker Daniels LLP

(57) ABSTRACT

The present disclosure relates generally to methods and compositions useful in cell and tissue biology and therapeutics. In particular, an in vitro method for differentiating pluripotent cells into endothelial colony forming cell-like cells (ECFC-like cells) is provided. A purified human cell population of NRP-1+CD31+ ECFC-like cells is provided, wherein at least some of the cells in the population have a high proliferation potential. Therapeutic and test agent screening methods for using the cell populations of the present disclosure are provided.

15 Claims, 31 Drawing Sheets

(56) References Cited

OTHER PUBLICATIONS

Yoder, M.C. et al. Redefining endothelial progenitor cells via clonal analysis and hematopoietic stem/progenitor cell principals. Blood 109, 1801-1809 (2007).

Ingram, D.A. et al. Vessel wall-derived endothelial cells rapidly proliferate because they contain a complete hierarchy of endothelial progenitor cells. Blood 105, 2783-2786 (2005).

Ingram, D.A. et al. Identification of a novel hierarchy of endothelial progenitor cells using human peripheral and umbilical cord blood. Blood 104, 2752-2760 (2004).

Critser, P.J., Kreger, S.T., Voytik-Harbin, S.L. & Yoder, M.C. Collagen matrix physical properties modulate endothelial colony forming cell-derived vessels in vivo. Microvasc Res 80, 23-30 (2010).

Au, P. et al. Differential in vivo potential of endothelial progenitor cells from human umbilical cord blood and adult peripheral blood to form functional long-lasting vessels. Blood 111, 1302-1305 (2008).

Melero-Martin, J.M. et al. Engineering robust and functional vascular networks in vivo with human adult and cord blood-derived progenitor cells. Circ Res 103, 194-202 (2008).

Lin, Y., Weisdorf, D.J., Solovey, A. & Hebbel, R.P. Origins of circulating endothelial cells and endothelial outgrowth from blood. J Clin Invest 105, 71-77 (2000).

Ikpeazu, C., Davidson, M.K., Halteman, D., Browning, P.J. & Brandt, S.J. Donor origin of circulating endothelial progenitors after allogeneic bone marrow transplantation. Biol Blood Marrow Transplant 6, 301-308 (2000).

Moubarik, C. et al. Transplanted late outgrowth endothelial progenitor cells as cell therapy product for stroke. Stem Cell Rev 7, 208-220 (2011).

Schwarz, T.M. et al. Vascular incorporation of endothelial colony-forming cells is essential for functional recovery of murine ischemic tissue following cell therapy. Arterioscler Thromb Vasc Biol 32, e13-21 (2012).

Saif, J. et al. Combination of injectable multiple growth factor-releasing scaffolds and cell therapy as an advanced modality to enhance tissue neovascularization. Arterioscler Thromb Vasc Biol 30, 1897-1904 (2010).

Dubois, C. et al. Differential effects of progenitor cell populations on left ventricular remodeling and myocardial neovascularization after myocardial infarction. J Am Coll Cardiol 55, 2232-2243 (2010).

Schuh, A. et al. Transplantation of endothelial progenitor cells improves neovascularization and left ventricular function after myocardial infarction in a rat model. Basic Res Cardiol 103, 69-77 (2008).

Stitt, A.W. et at Vascular stem cells and ischaemic retinopathies. Prog Retin Eye Res 30, 149-166 (2011).

Medina, R.J., O'Neill, C.L., Humphreys, M.W., Gardiner, T.A. & Stitt, A.W. Outgrowth endothelial cells: characterization and their potential for reversing ischemic retinopathy. Invest Ophthalmol Vis Sci 51, 5906-5913 (2010).

Bouvard, C. et al. alpha6-integrin subunit plays a major role in the proangiogenic properties of endothelial progenitor cells. Arterioscler Thromb Vasc Biol 30, 1569-1575 (2010).

Lee, J.H., Lee, S.H., Yoo, S.Y., Asahara, T. & Kwon, S.M. CD34 Hybrid Cells Promote Endothelial Colony-Forming Cell Bioactivity and Therapeutic Potential for Ischemic Diseases. Arterioscler Thromb Vasc Biol (2013).

Stroncek, J.D., Ren, L.C., Klitzman, B & Reichert, W.M. Patient-derived endothelial progenitor cells improve vascular graft patency in a rodent model. Acta Biomater 8, 201-208 (2012).

Robbins, R.D., Prasain, N., Maier, B.F., Yoder, M.C. & Mirmira, R.G. Inducible pluripotent stem cells: not quite ready for prime time? Curr Opin Organ Transplant 15, 61-67 (2010).

Broxmeyer, H.E. et al. Hematopoietic stem/progenitor cells, generation of induced pluripotent stem cells, and isolation of endothelial progenitors from 21- to 23.5-year cryopreserved cord blood. Blood 117, 4773-4777 (2011).

Lee, M.R. et al. Epigenetic regulation of NANOG by miR-302 cluster-MBD2 completes induced pluripotent stem cell reprogramming. Stem Cells 31, 666-681 (2012).

Choi, K.D. et al. Hematopoietic and endothelial differentiation of human induced pluripotent stem cells. Stem Cells 27, 559-567 (2009).

Cimato, T. et al. Neuropilin-1 identifies endothelial precursors in human and murine embryonic stem cells before CD34 expression. Circulation 119, 2170-2178 (2009).

James, D. et al. Expansion and maintenance of human embryonic stem cell-derived endothelial cells by TGFbeta inhibition is Id1 dependent. Nat Biotechnol (2010).

Taura, D. et al. Induction and isolation of vascular cells from human induced pluripotent stem cells—brief report. Arterioscler Thromb Vasc Biol 29, 1100-1103 (2009).

Goldman, O. et al. A boost of BMP4 accelerates the commitment of human embryonic stem cells to the endothelial lineage. Stem Cells 27, 1750-1759 (2009).

Feng, Q. et al. Hemangioblastic derivatives from human induced pluripotent stem cells exhibit limited expansion and early senescence. Stem Cells 28, 704-712 (2010).

Rufaihah, A.J. et al. Endothelial cells derived from human iPSCS increase capillary density and improve perfusion in a mouse model of peripheral arterial disease. Arterioscler Thromb Vasc Biol 31, e72-79 (2011).

Nourse, M.B. et al. VEGF induces differentiation of functional endothelium from human embryonic stem cells: implications for tissue engineering. Arterioscler Thromb Vasc Biol 30, 80-89 (2010).

Sone, M. et al. Pathway for differentiation of human embryonic stem cells to vascular cell components and their potential for vascular regeneration. Arterioscler Thromb Vasc Biol 27, 2127-2134 (2007).

Vodyanik, M.A., Bork, J.A., Thomson, J.A. & Slukvin, II Human embryonic stem cell-derived CD34+ cells: efficient production in the coculture with OP9 stromal cells and analysis of lymphohematopoietic potential. Blood 105, 617-626 (2005).

Ginsberg, M. et al. Efficient direct reprogramming of mature amniotic cells into endothelial cells by ETS factors and TGFbeta suppression. Cell 151, 559-575 (2012).

Carmeliet, P. et al. Abnormal blood vessel development and lethality in embryos lacking a single VEGF allele. Nature 380, 435-439 (1996).

Gerber, H.P. et al. VEGF is required for growth and survival in neonatal mice. Development 126, 1149-1159 (1999).

Staton, C.A., Kumar, I., Reed, M.W. & Brown, N.J. Neuropilins in physiological and pathological angiogenesis. J Pathol 212, 237-248 (2007).

Takashima, S. et al. Targeting of both mouse neuropilin-1 and neuropilin-2 genes severely impairs developmental yolk sac and embryonic angiogenesis. Proc Natl Acad Sci U S A 99, 3657-3662 (2002).

Evseenko, D. et al. Mapping the first stages of mesoderm commitment during differentiation of human embryonic stem cells. Proc Natl Acad Sci U S A 107, 13742-13747 (2010).

Kuilman, T., Michaloglou, C., Mooi, W.J. & Peeper, D.S. The essence of senescence. Genes Dev 24, 2463-2479 (2010).

Kitsukawa, T., Shimono, A., Kawakami, A., Kondoh, H. & Fujisawa, H. Overexpression of a membrane protein, neuropilin, in chimeric mice causes anomalies in the cardiovascular system, nervous system and limbs. Development 121, 4309-4318 (1995).

Zachary, I.C. How neuropilin-1 regulates receptor tyrosine kinase signalling: the knowns and known unknowns. Biochem Soc Trans 39, 1583-1591 (2011).

Soker, S., Miao, H.Q., Nomi, M., Takashima, S & Klagsbrun, M. VEGF165 mediates formation of complexes containing VEGFR-2 and neuropilin-1 that enhance VEGF165-receptor binding. J Cell Biochem 85, 357-368 (2002).

(56) References Cited

OTHER PUBLICATIONS

Pan, Q. et al. Blocking neuropilin-1 function has an additive effect with anti-VEGF to inhibit tumor growth. Cancer Cell 11, 53-67 (2007).

Herzog, B., Pellet-Many, C., Britton, G., Hartzoulakis, B. & Zachary, I.C. VEGF binding to NRP1 is essential for VEGF stimulation of endothelial cell migration, complex formation between NRP1 and VEGFR2, and signaling via FAK Tyr407 phosphorylation. Mol Biol Cell 22, 2766-2776 (2011).

Evans, I.M. et al. Neuropilin-1 signaling through p130Cas tyrosine phosphorylation is essential for growth factor-dependent migration of glioma and endothelial cells. Mol Cell Biol 31, 1174-1185 (2011).

Uniewicz, K.A., Cross, M.J. & Fernig, D.G. Exogenous recombinant dimeric neuropilin-1 is sufficient to drive angiogenesis. J Biol Chem 286, 12-23 (2011).

Lippmann, E.S. et al. Derivation of blood-brain barrier endothelial cells from human pluripotent stem cells. Nat Biotechnol 30, 783-791 (2012).

Thomson, J.A. et al. Embryonic stem cell lines derived from human blastocysts. Science 282, 1145-1147 (1998).

Yu, J. et al. Human induced pluripotent stem cells free of vector and transgene sequences. Science 324, 797-801.

Prasain, N., Meador, J.L. & Yoder, M.C. Phenotypic and functional characterization of endothelial colony forming cells derived from human umbilical cord blood. J Vis Exp (2012).

Bailey, J.L. et al. Collagen oligomers modulate physical and biological properties of three-dimensional self-assembled matrices. Biopolymers 95, 77-93 (2011).

Samuel, et al. Generation of functionally competent and durable engineered blood vessels from human induced pluripotent cells. *PNAS* Early Edition 1310675110.

* cited by examiner

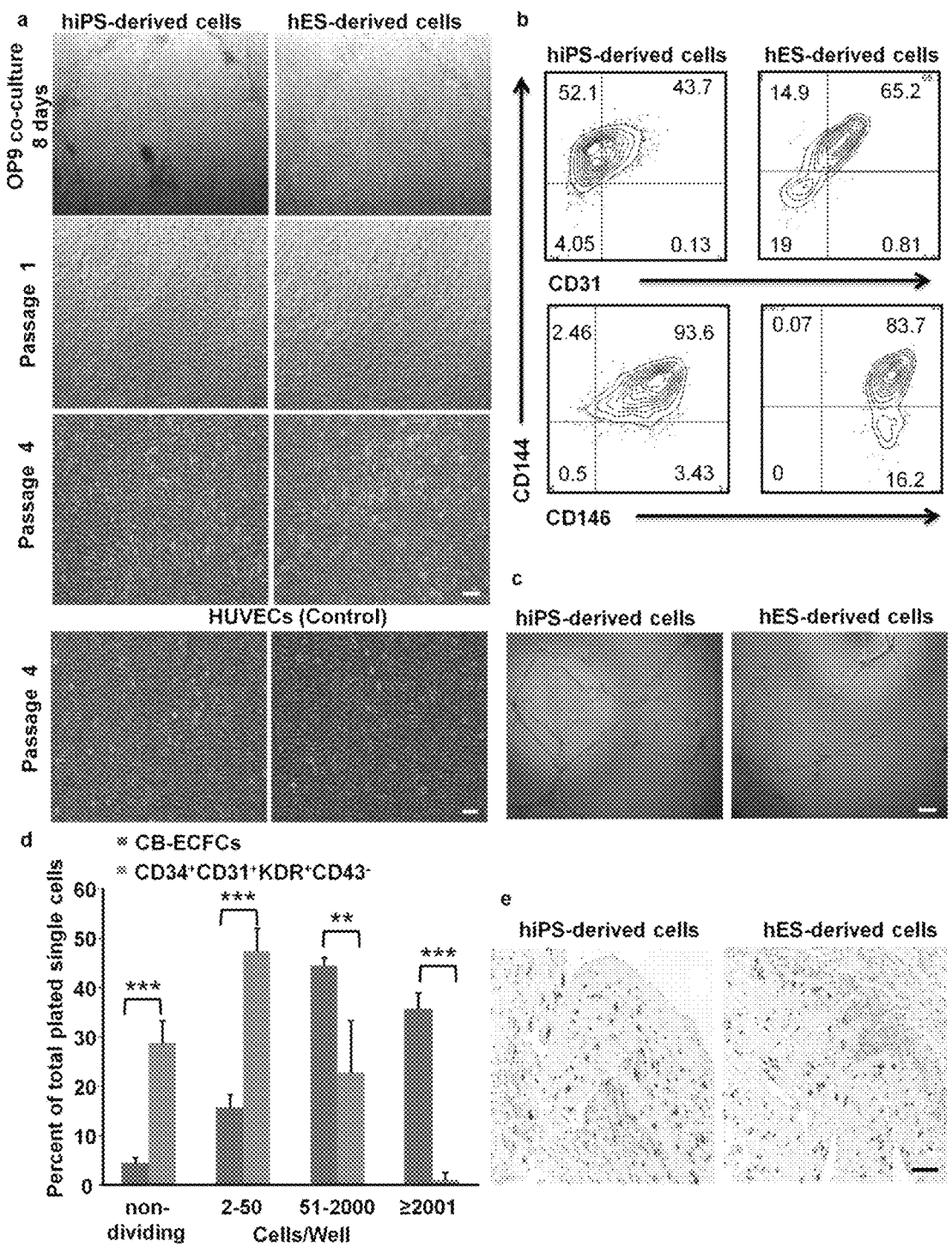
FIGS. 1A-E

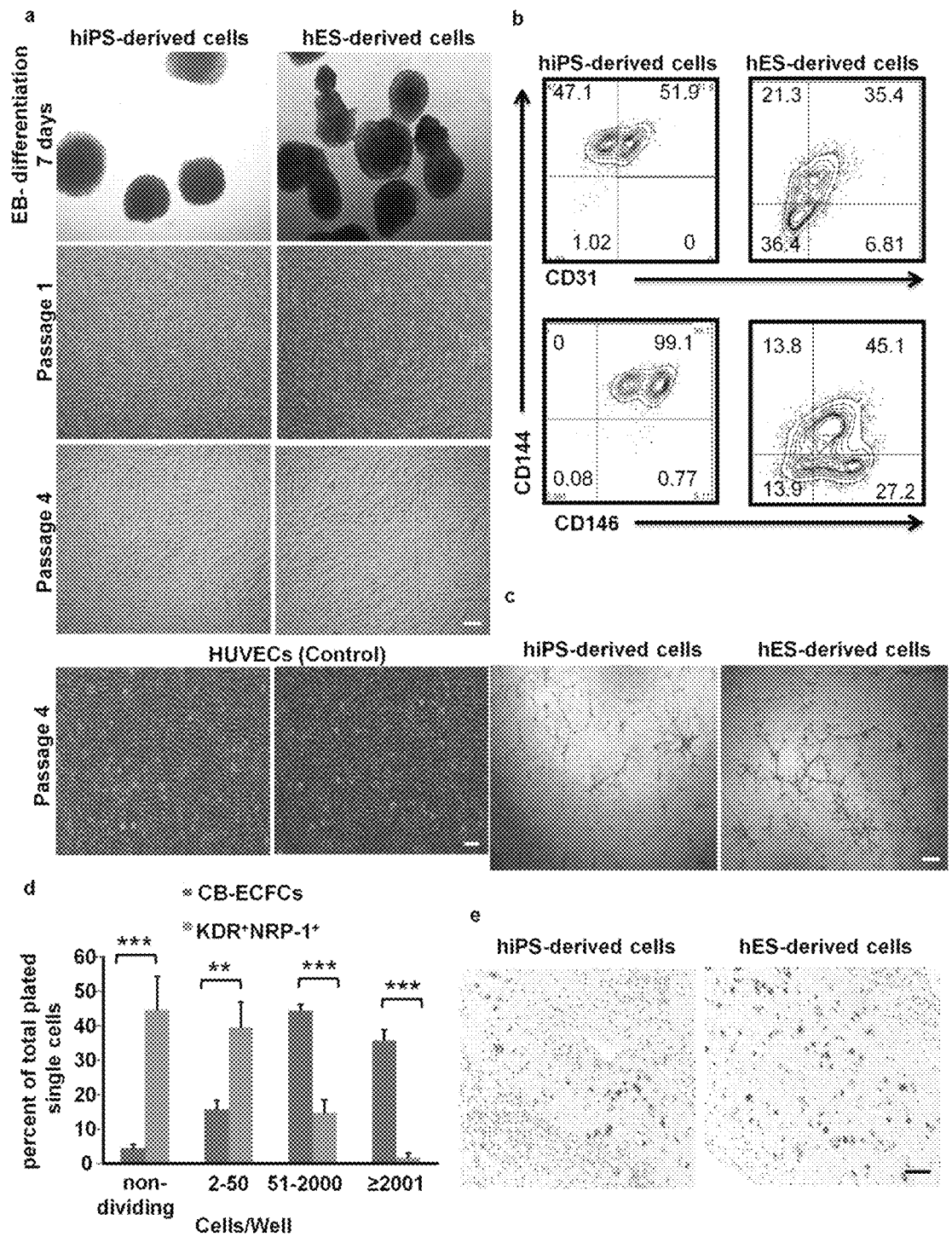
FIGS. 2A-E

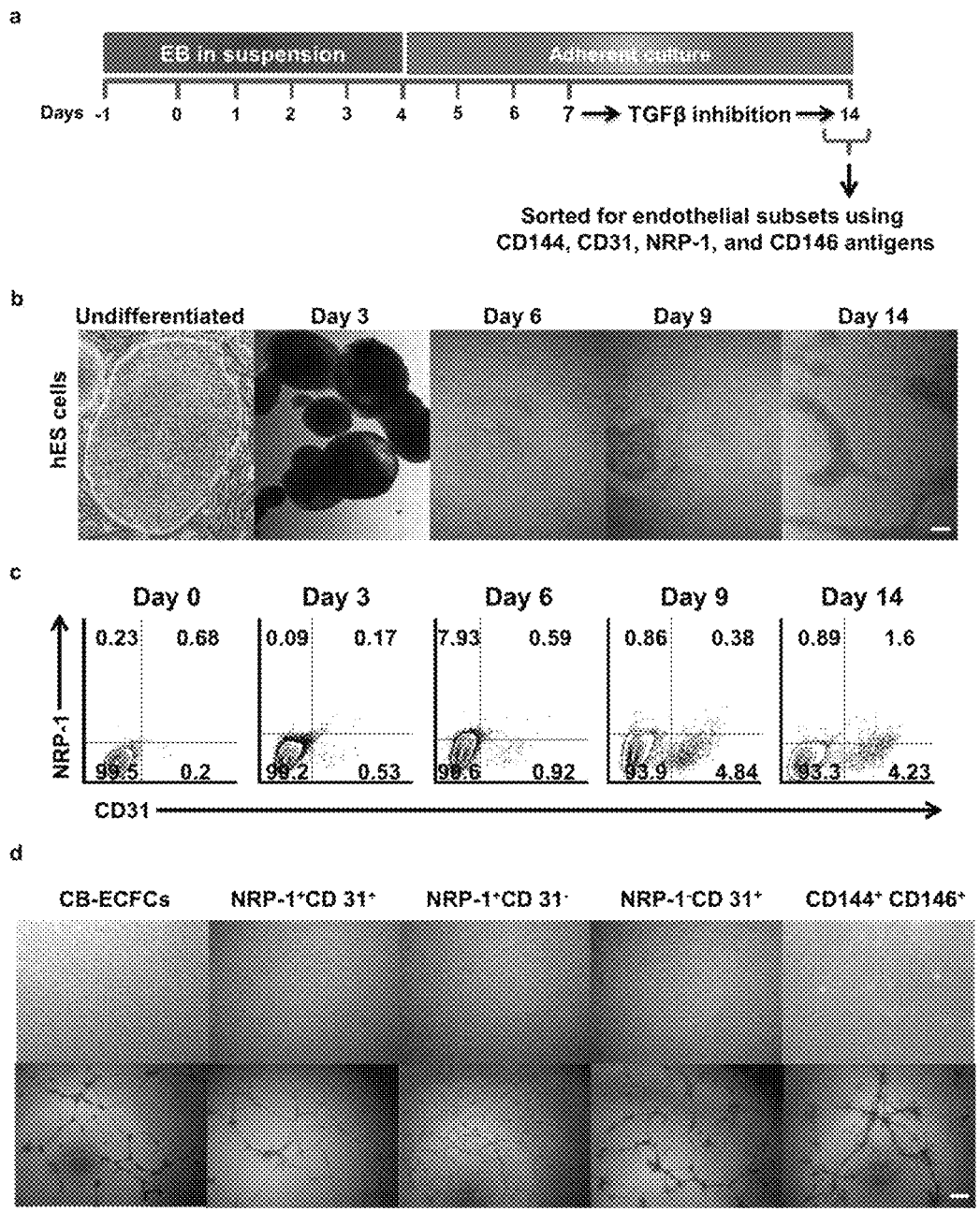
FIGS. 3A-D

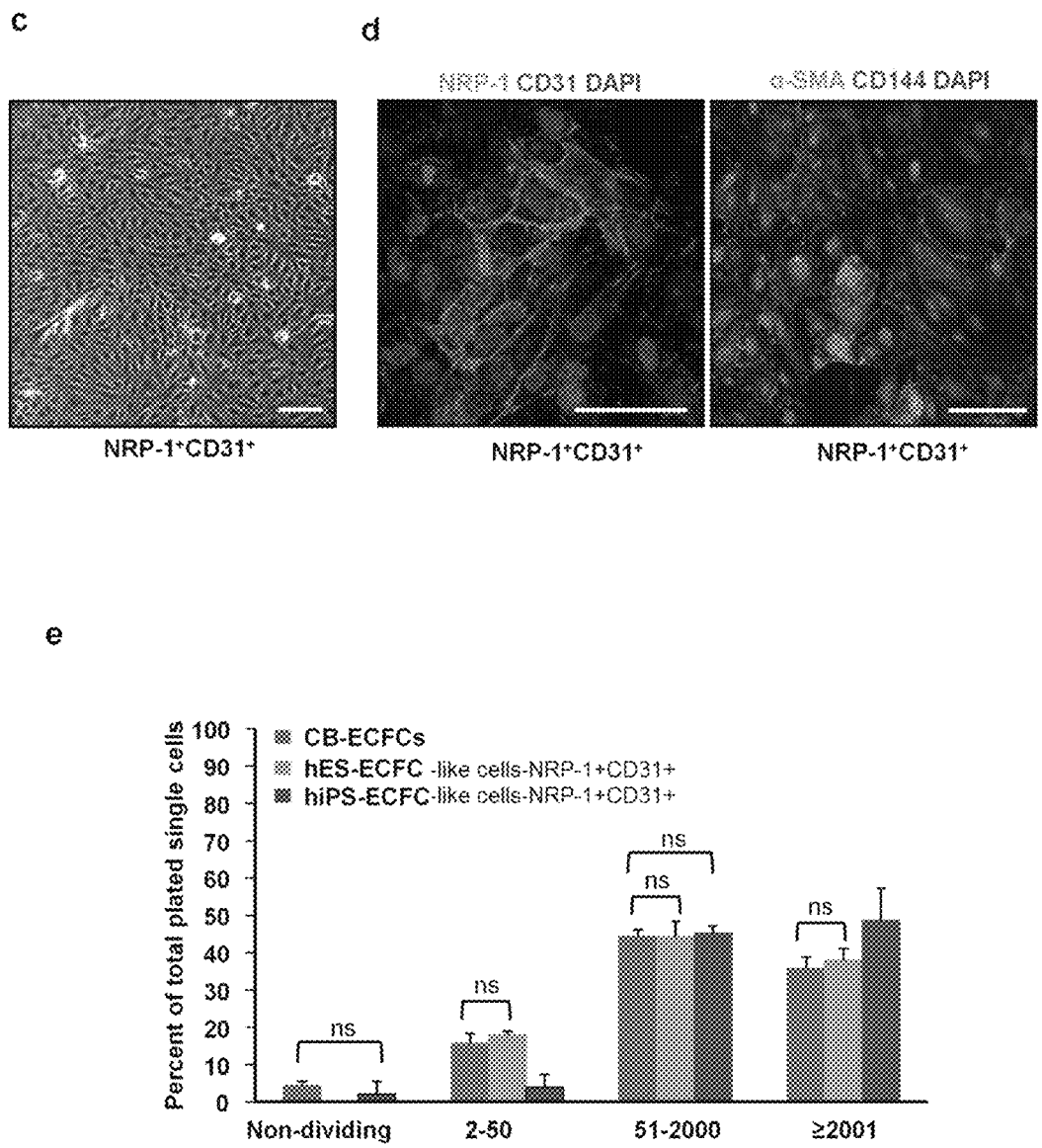
FIGS. 4C-E

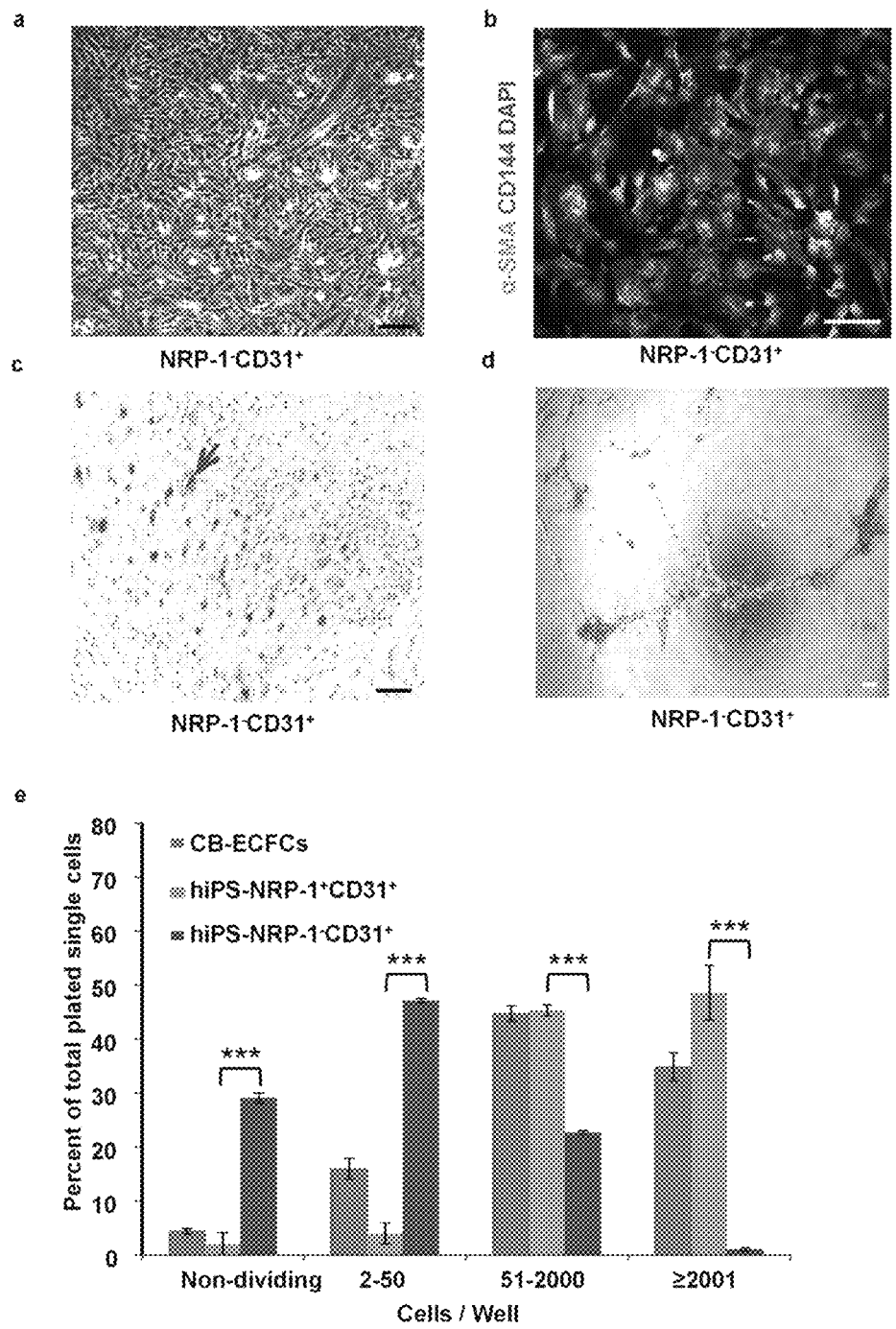
FIGS. 6A-E

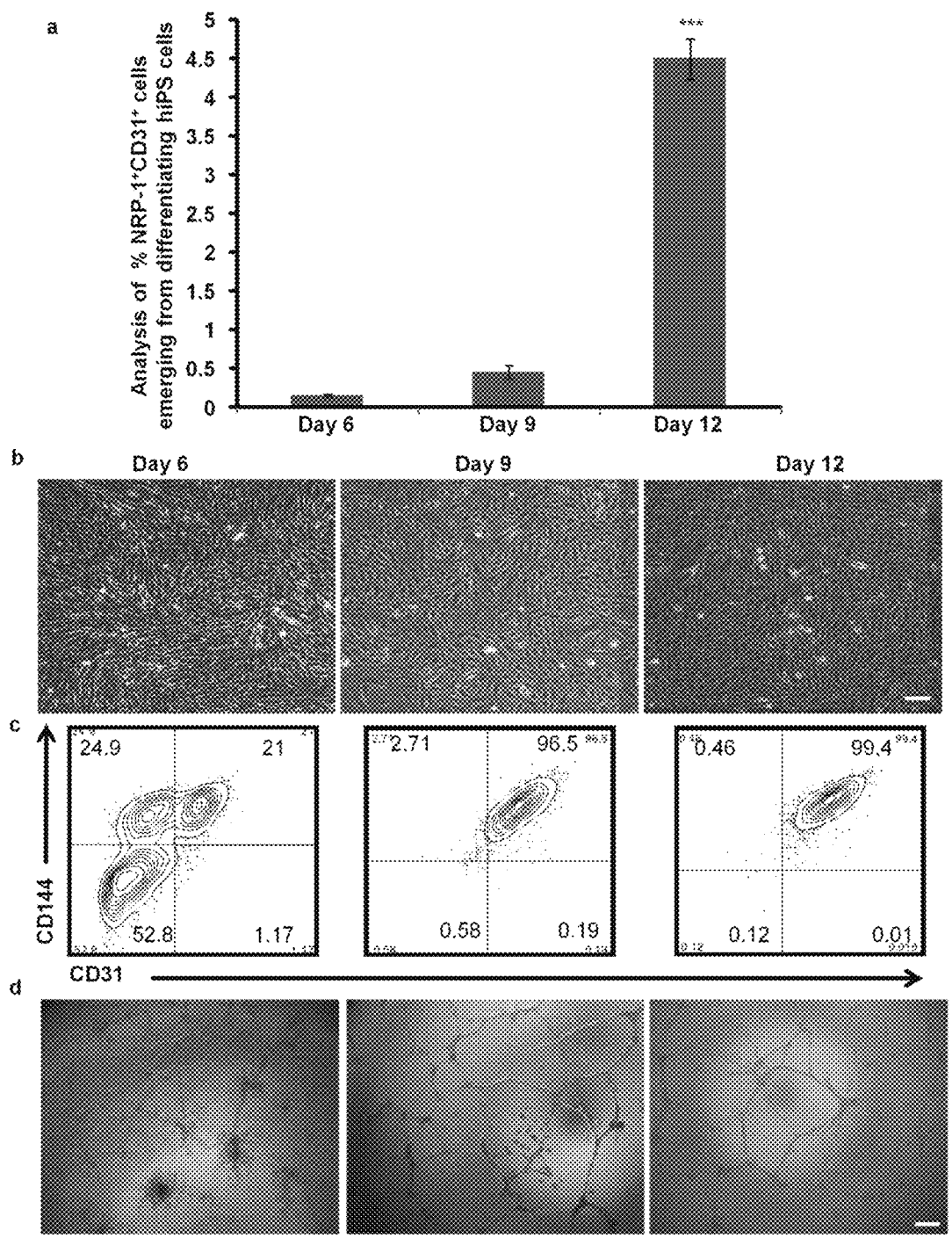
FIGS. 7A-D

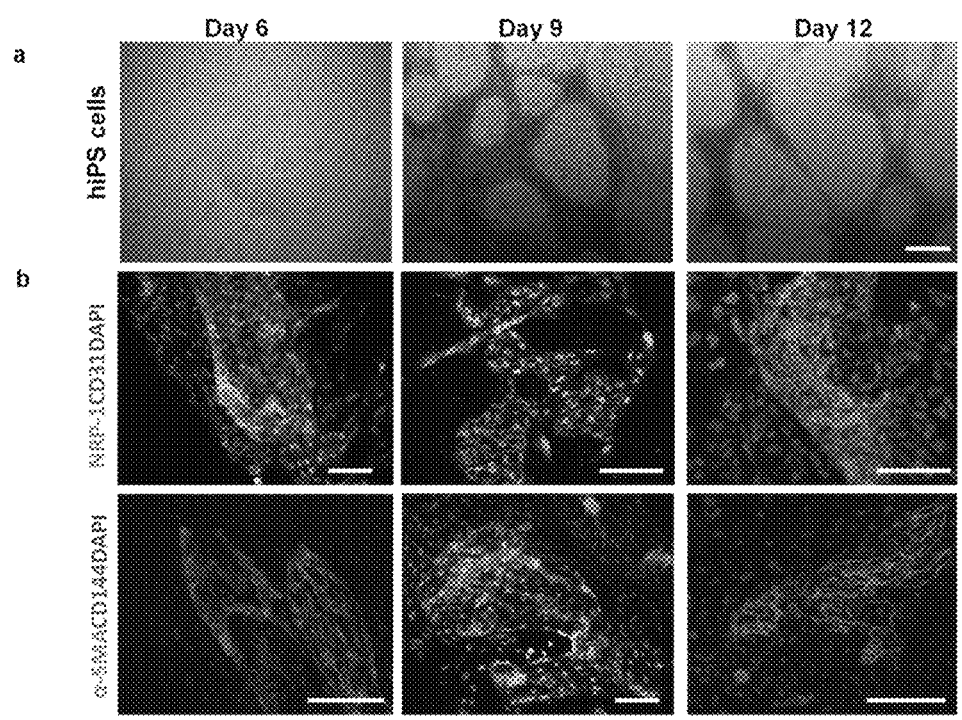
FIGS. 8A-B

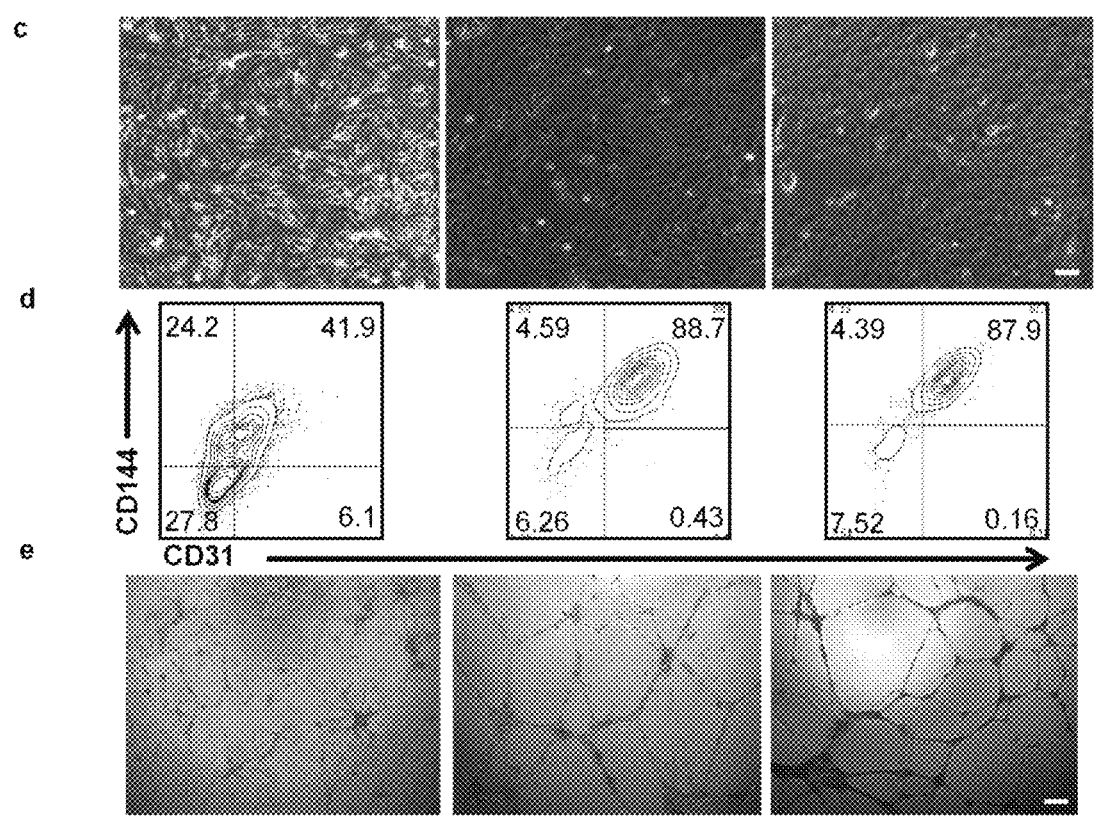
FIGS. 8C-E

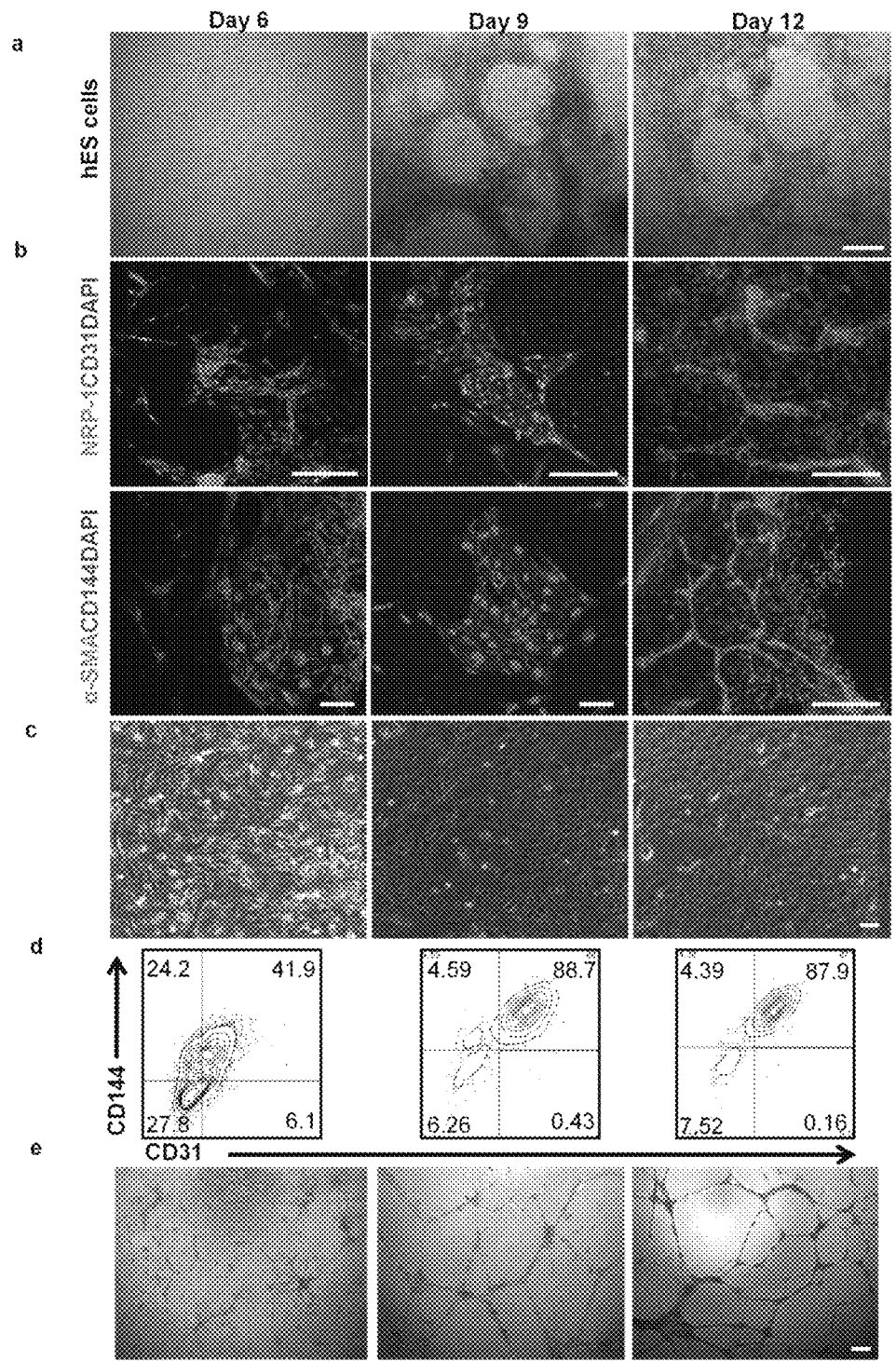
FIGS. 9A-E

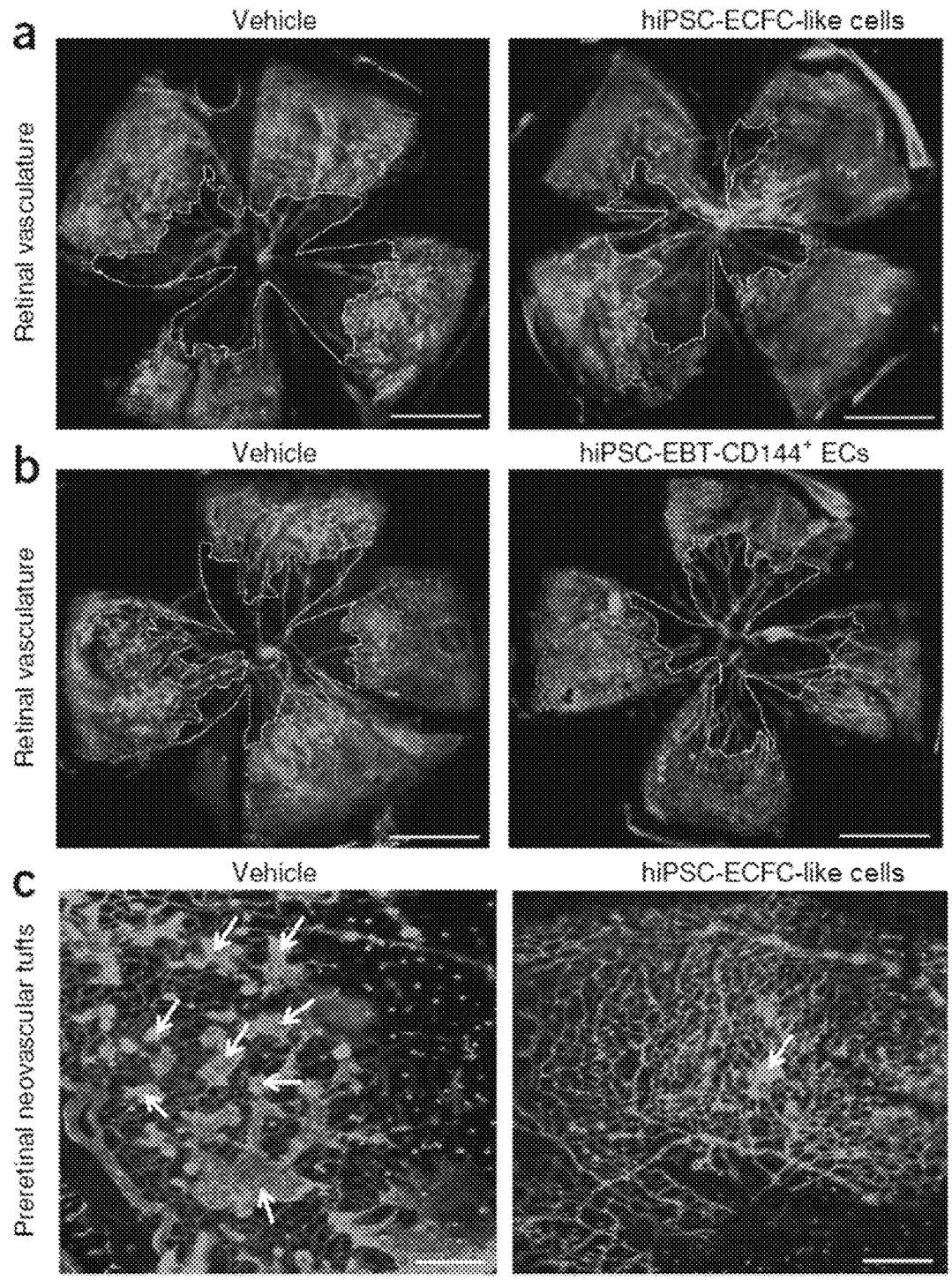
FIGS. 10A-C

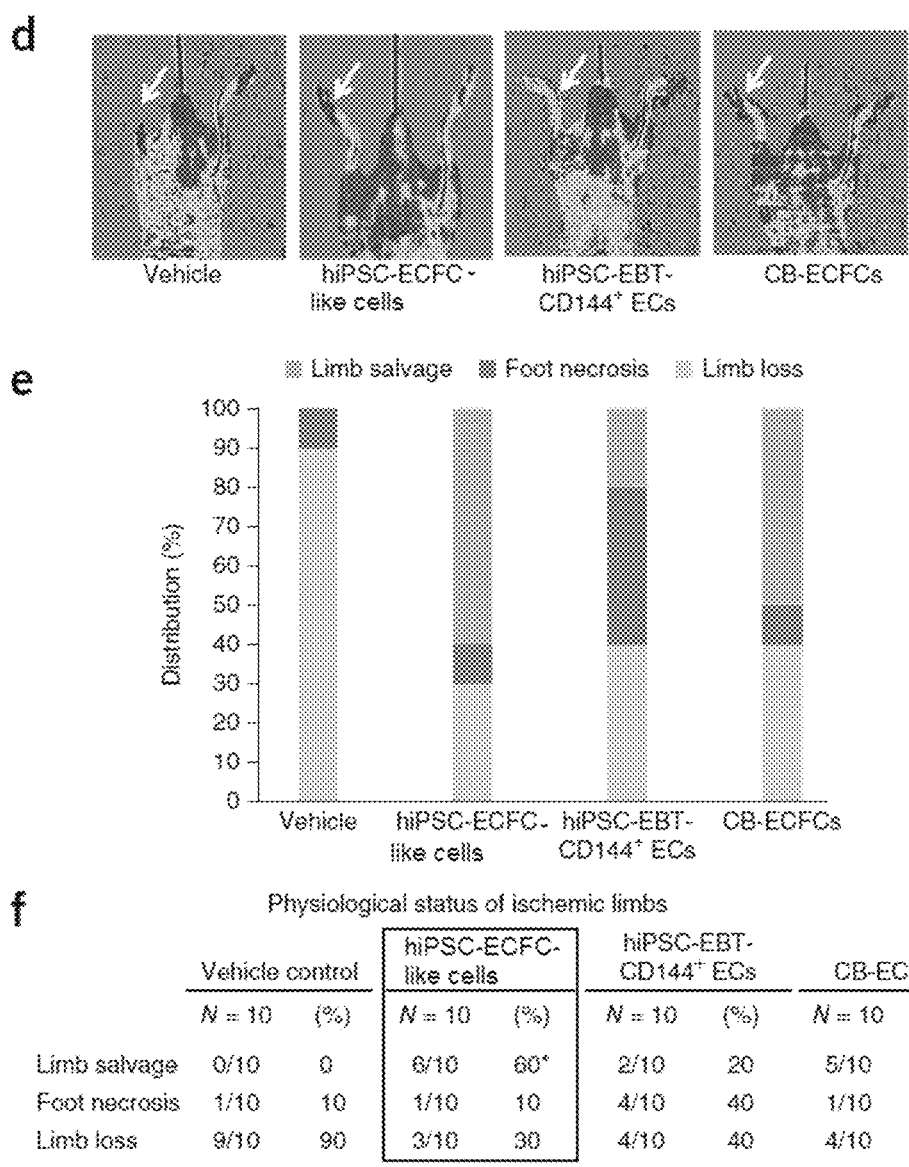
FIGS. 10D-F a b

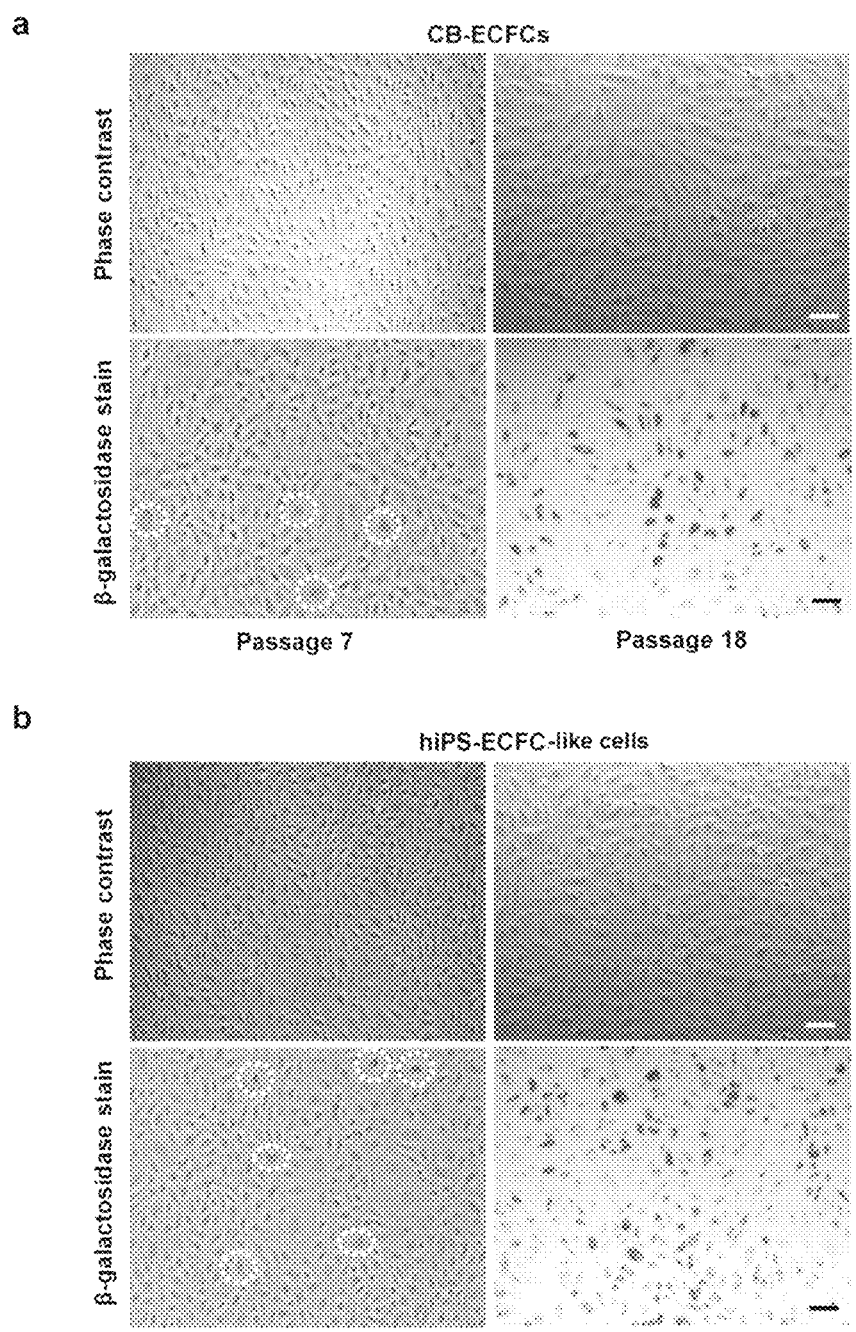
FIGS. 12A-B

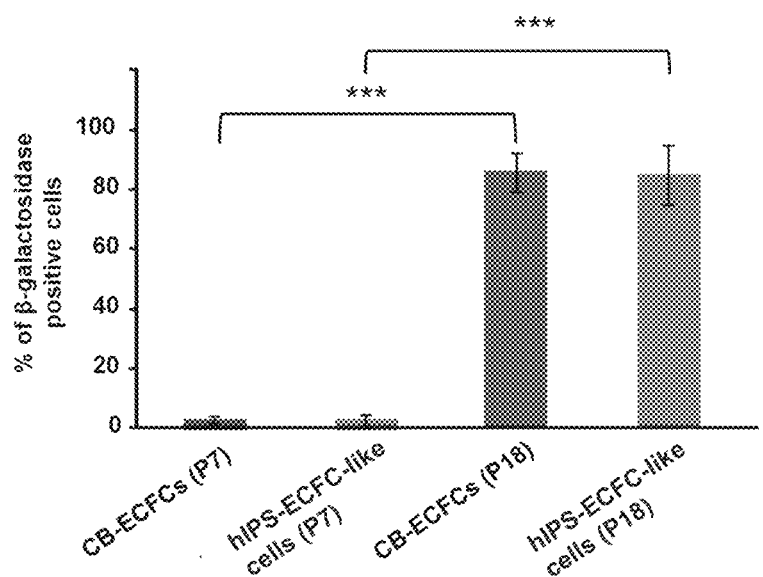
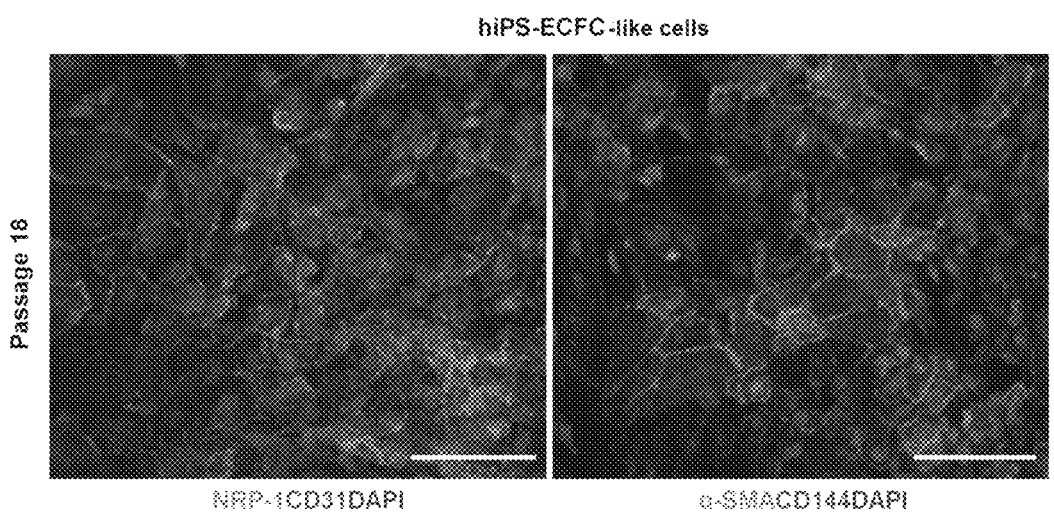
FIGS. 12C-D

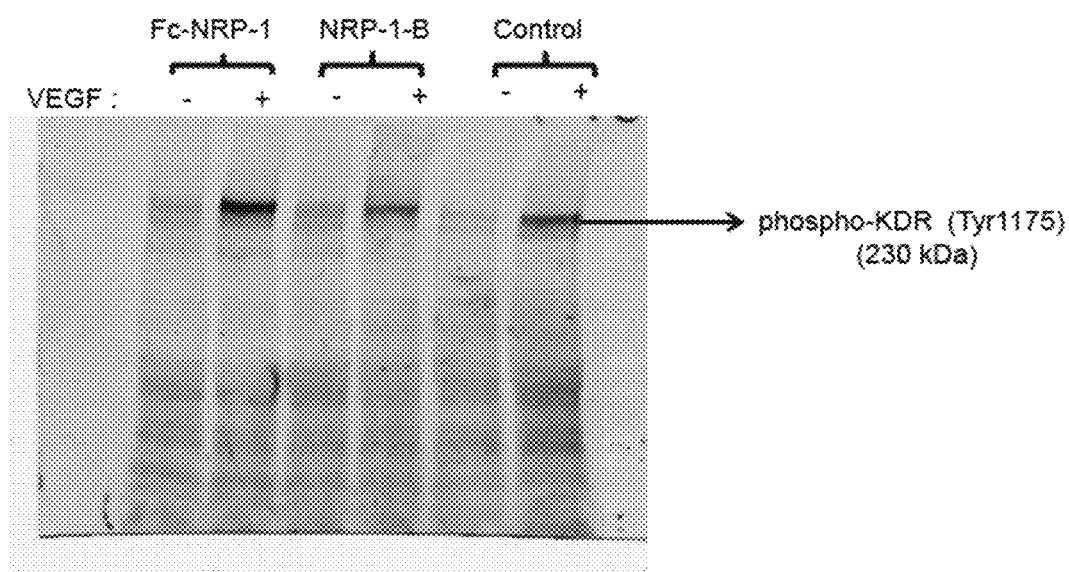
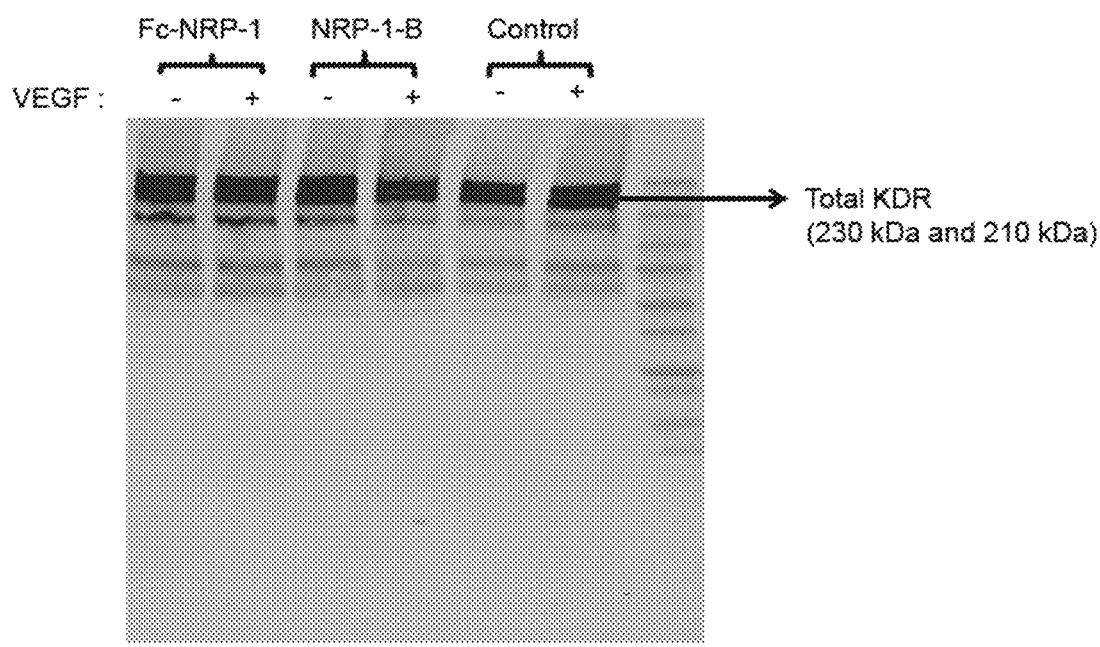
FIGS. 14A-B

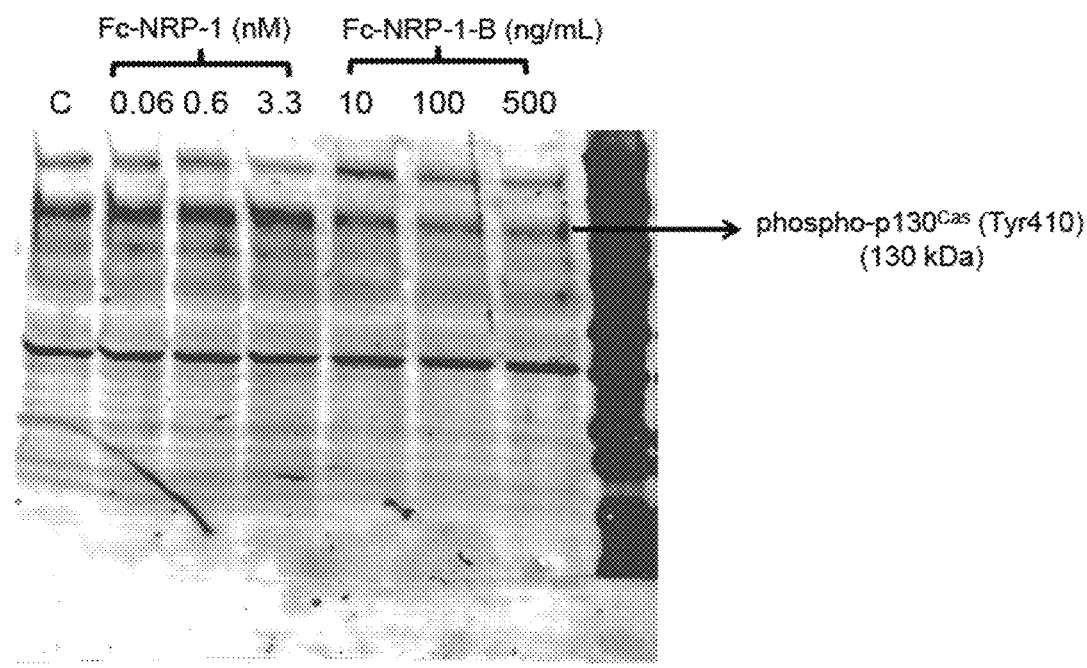
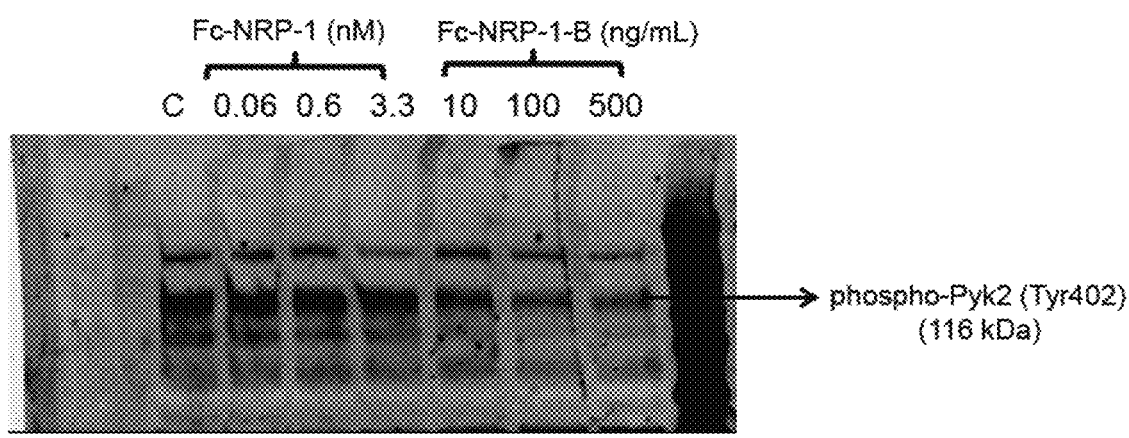
FIGS. 14C-D

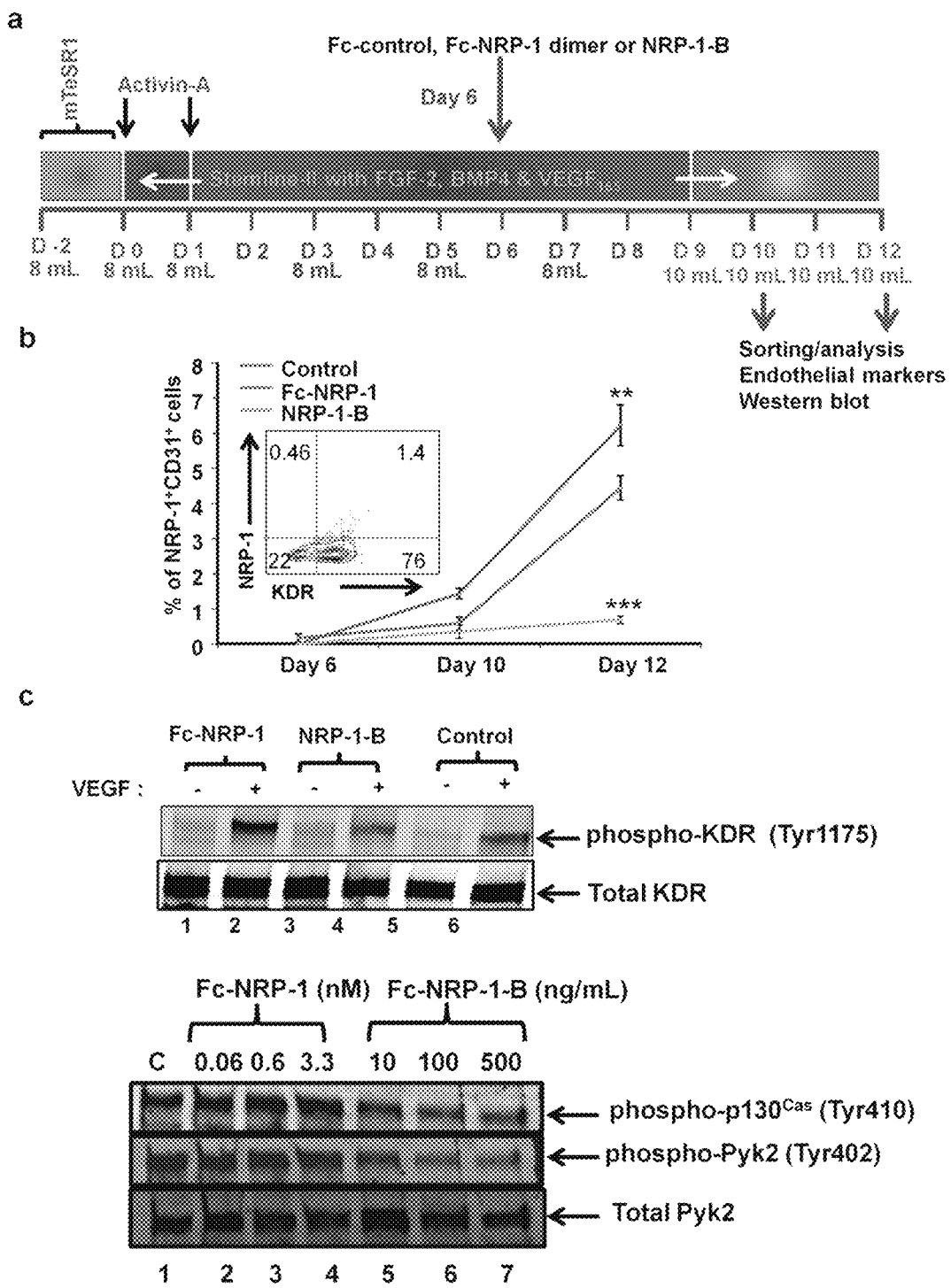
FIGS. 15A-C

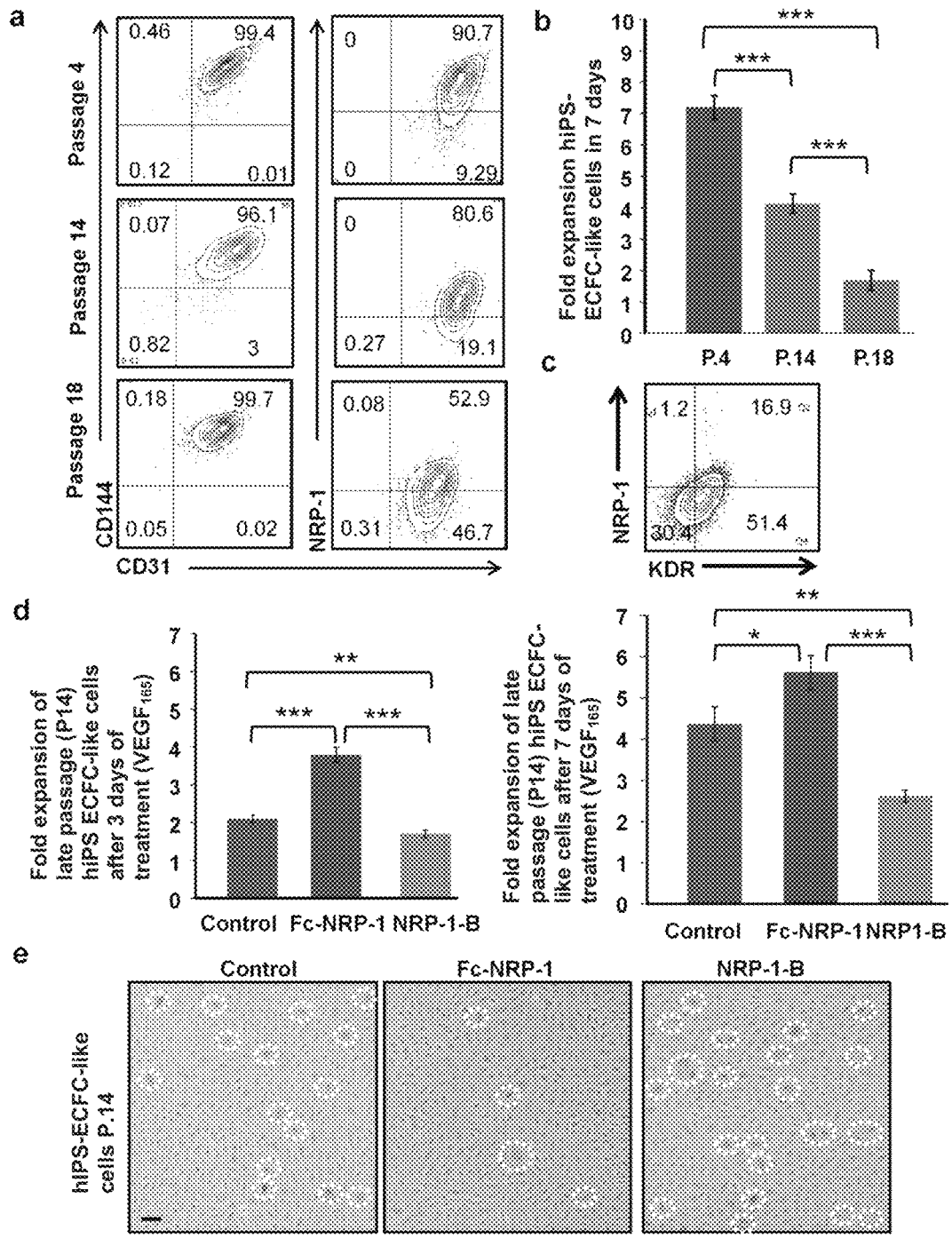
FIGS. 16A-E

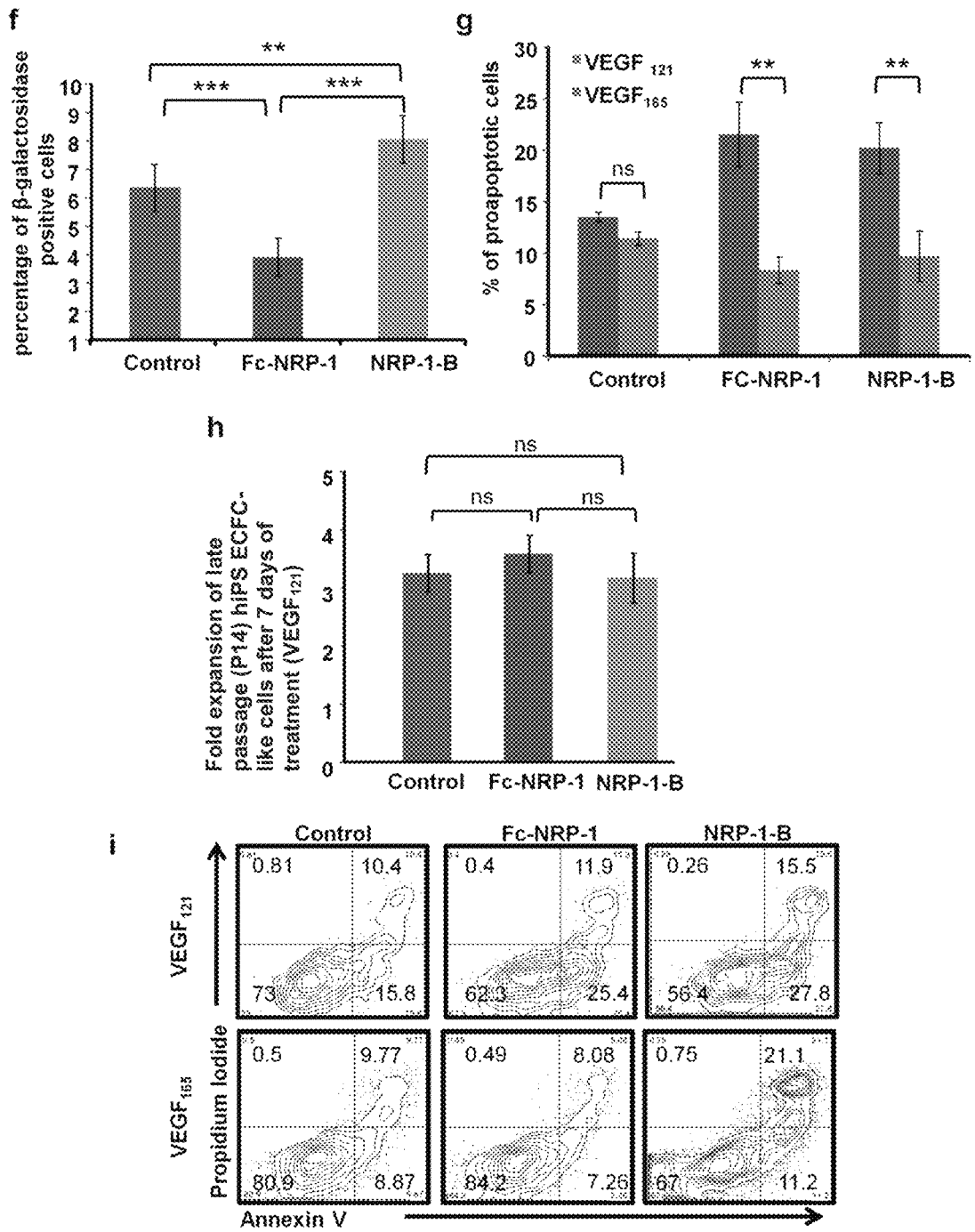
FIGS. 16F-I

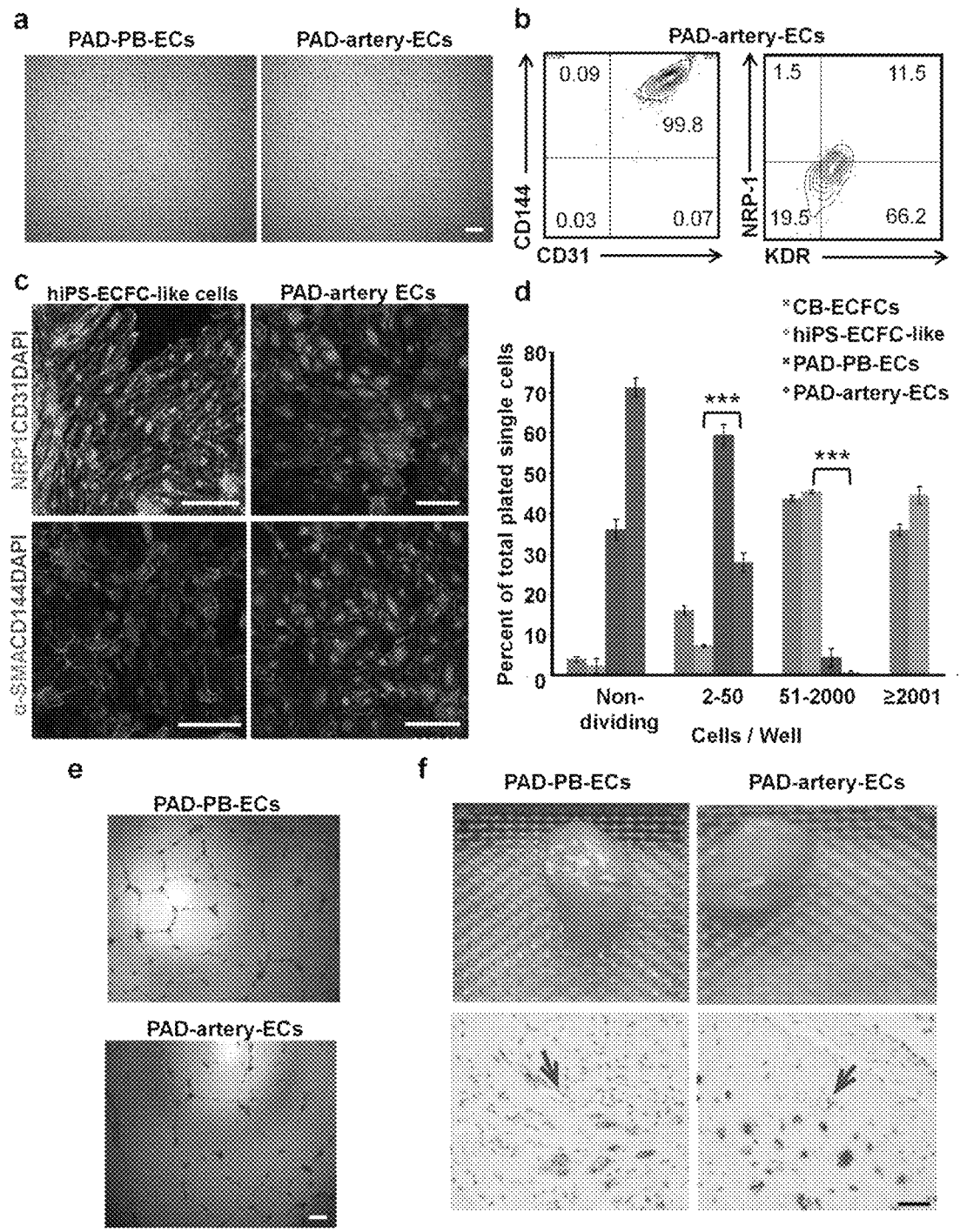
FIGS. 17A-F

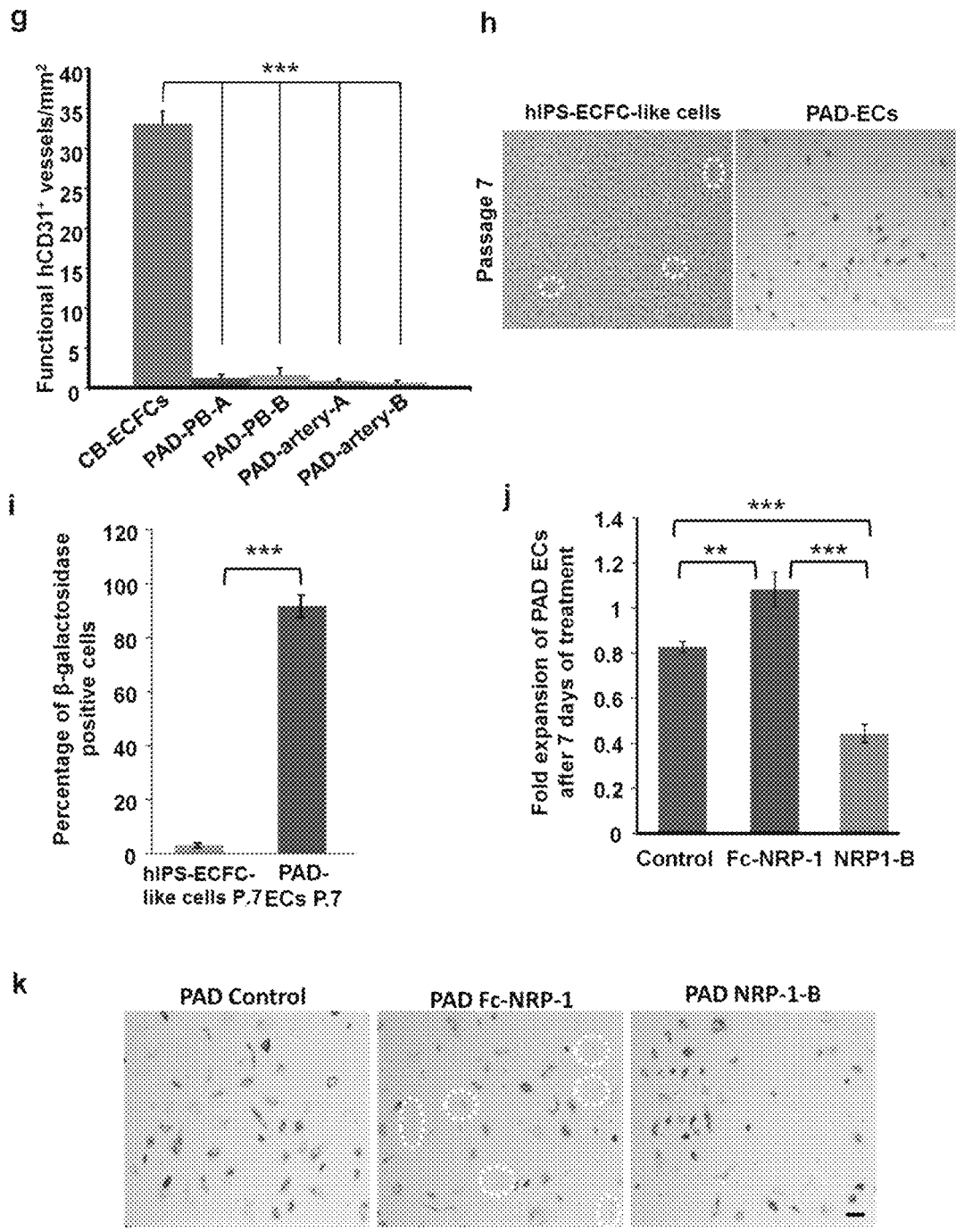
FIGS. 17G-K

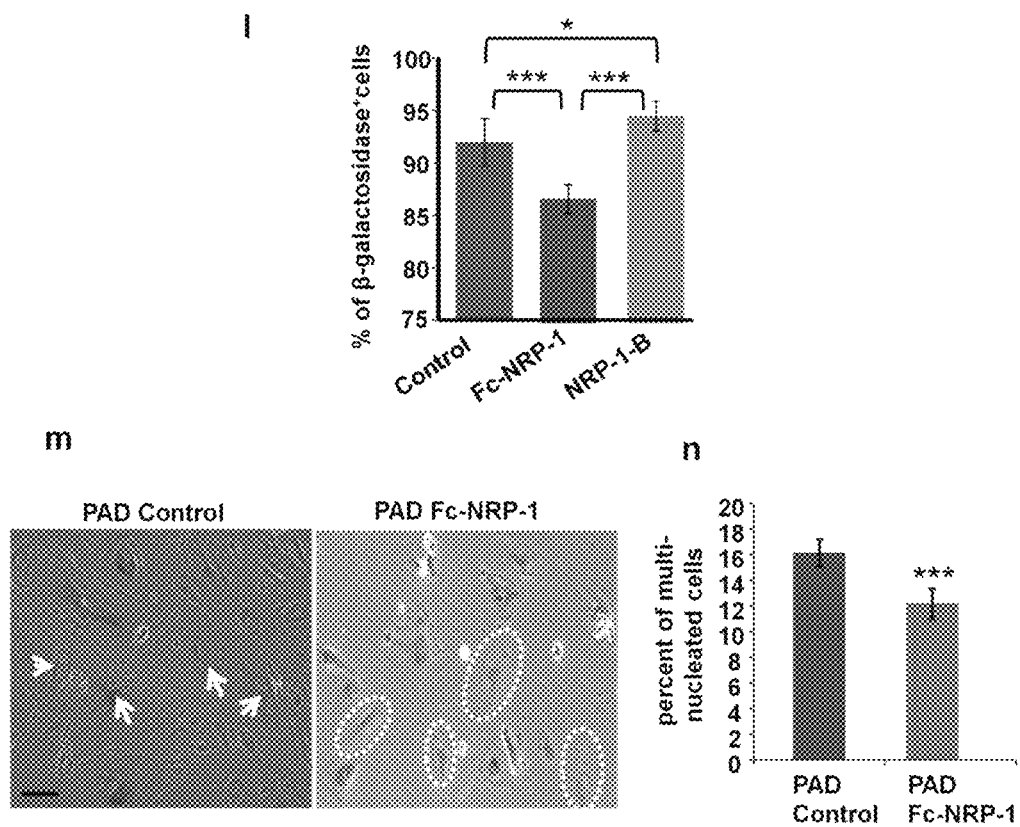
FIGS. 17L-N

METHOD FOR GENERATING ENDOTHELIAL COLONY FORMING CELL-LIKE CELLS

CROSS REFERENCE TO PRIOR APPLICATIONS

This application is a U.S. National Phase filing of PCT/US2015/020008, filed Mar. 11, 2015, which claims the benefit of U.S. Provisional Patent Application No. 61/951,103, filed Mar. 11, 2014, the entire disclosures of both of which are hereby expressly incorporated by reference herein.

FIELD OF THE DISCLOSURE

The present disclosure relates to the fields of cell and tissue biology. More particularly, the present disclosure relates to lineage-specific differentiation of pluripotent stem cells into endothelial colony forming cell-like cells (ECFC-like cells).

BACKGROUND OF THE DISCLOSURE

Endothelial colony forming cells (ECFCs) are rare circulating endothelial cells, particularly abundant in umbilical cord blood, with clonal proliferative potential and intrinsic in vivo vessel forming ability[1-6]. ECFCs, also called blood outgrowth endothelial cells (BOEC)[7], have been shown to be directly transplantable in sex-mismatched human bone marrow transplant patients, with the most proliferative circulating BOEC displaying genetic markings of the donor marrow[7,8]. It is not understood what type of cell within donor marrow gives rise to ECFCs. When cultured ECFCs are injected intravenously into pre-clinical rodent vascular injury models, they are rapidly recruited the site of vascular injury or tissue ischemia to orchestrate initiation of a vasculogenic response[9-11]. Human ECFCs have been reported to enhance vascular repair and improve blood flow following myocardial infarction[12,13], stroke[9], ischemic retinopathy[14,15], ischemic limb injury[10,11,16,17], and to engraft and re-endothelialize denuded vascular segments or implanted grafts[18]. In elderly patients and subjects with peripheral arterial disease (PAD) and critical limb ischemia (CLI), circulating or resident ECFCs may become prone to replicative senescence (i.e., ECFCs may lack proliferative potential), thus rendering them impotent for autologous vascular repair. At least for these reasons, it is desirable to find an alternate source of ECFCs that may be used for vascular repair.

Human pluripotent stem cells (human embryonic stem cells and induced pluripotent stem cells, collectively hPSCs) display virtually unlimited self-renewal capacity and ability to differentiate into any cell type in the animal body[19-21]. Human pluripotent stem cells have been reported to differentiate into cells of the endothelial lineage[22-31]. However, in vitro hPSC-derived endothelial cells are unstable (e.g., reported to drift to various non-endothelial phenotypes[24,32]), exhibit low proliferative potential with a proclivity to reach replicative senescence within 5-7 passages[26,27,32], and/or lack a capacity for blood vessel formation in vivo in the absence of co-implantation with supportive cells[51]. There is no published evidence (other than that of the inventors) for in vitro derivation from hPSCs of endothelial cells having proliferative potential equal to or greater than that of cord blood ECFCs (CB-ECFCs) and having the capacity to form blood vessels in vivo in the absence of co-cultured or co-implanted cells.

It is desirable to mitigate and/or obviate one or more of the above deficiencies.

SUMMARY OF THE DISCLOSURE

The present disclosure is broadly summarized as relating to methods for generating endothelial colony forming cell-like cells (ECFC-like cells) from hPSCs. A protocol for reproducibly differentiating hPSCs into populations of ECFC-like cells having molecular, morphological and functional properties that are similar to CB-ECFCs is provided herein.

In an aspect of the present disclosure, the is provided a method for generating an isolated population of human endothelial colony forming cell-like cells (ECFC-like cells) from human pluripotent stem cells, the method comprising:
  a) providing pluripotent stem cells;
  b) inducing the pluripotent stem cells to undergo endothelial differentiation, wherein inducing comprises:
    i) culturing the pluripotent stem cells for about 24 hours in an endothelial differentiation medium comprising Activin A, BMP-4, VEGF and FGF-2; and
    ii) replacing the medium of step i) with an endothelial differentiation medium comprising BMP-4, VEGF and FGF-2 about every one or two days thereafter; and
  c) isolating from the cells induced to undergo differentiation the ECFC-like cells, wherein the ECFC-like cells are CD31+NRP-1+ and exhibit a cobblestone morphology.

In another aspect of the present disclosure, there is provided an isolated population of human NRP-1+CD31+ endothelial colony forming cell-like cells (ECFC-like cells), wherein the isolated ECFC-like cells have a capacity to form blood vessels when implanted into a mammal in the absence of co-implanted cells and wherein the isolated ECFC-like cells were derived in vitro from human pluripotent cells.

In another aspect of the present disclosure, there is provided an isolated population of human NRP-1+CD31+ endothelial colony forming cell-like cells (ECFC-like cells) obtained according to a method as described herein.

In another aspect of the present disclosure, there is provided a method for transplantation in a subject in need thereof, the method comprising providing to the subject an isolated population of cells as described herein.

In another aspect of the present disclosure, there is provided a method of treating a subject in need of epithelial repair, the method comprising providing to the subject a therapeutically effective amount of a population of cells as described herein.

In another aspect of the present disclosure, there is provided a pharmaceutical composition comprising endothelial colony forming cell-like cells (ECFC-like cells) obtained by a method as described herein.

In another aspect of the present disclosure, there is provided a method of examining a test agent for its ability to modify cellular activity, the method comprising:
  exposing at least one of the cells of the population of cells as described herein to a test agent and;
  observing the effect of the test agent on one or more of cell growth and cell viability.

BRIEF DESCRIPTION OF THE DRAWINGS

The patent or application file contains at least one drawing in color. Copies of this patent or patent application publication with color drawings will be provided by the Office upon request and payment of the necessary fee.

The features of the disclosure will become more apparent in the following detailed description in which reference is made to the appended drawings wherein:

FIGS. 1A-E illustrate examination of morphology, endothelial antigen expression, clonal proliferative potential, and in vitro and in vivo vessel forming potential of endothelial cells derived from hES and hiPS cells differentiated by co-culturing them in vitro with OP9 stromal cells.

FIG. 1A depicts representative phase contrast photomicrographs of hES and hiPS cells at day 8 after undergoing endothelial lineage differentiation in co-culture with OP9 cells (top panels); culture of isolated cells at P1 and P4 (middle panels); and characteristic cobblestone endothelial phenotype in human umbilical vein endothelial cells (HUVECs) control cells. All experiments were performed 5 times in duplicate; scale bars, 100 μm.

FIG. 1B depicts hiPS and hES-derived cells (P4) obtained from co-culturing cells with OP9 were stained with monoclonal antibodies against human CD31, CD144 and CD146. Percentages in the top panel contour plots indicates CD144 and CD31 double positive cells, percentages in the bottom panel contour plots indicates CD144 and CD146 double positive cells. All experiments were performed 4 times in duplicate; a representative contour plot is shown for each group.

FIG. 1C depicts representative photomicrographs of OP9 co-cultured hiPS and hES-derived cells (P4), which have formed a few large branches of capillary-like networks on Matrigel™. All experiments were performed 5 times in duplicate. Scale bar, 100 μm.

FIG. 1D depicts a bar graph showing clonal proliferative analysis of OP9 co-cultured hES-derived cells (P3 to P4) compared to a CB-ECFC control. All experiments were performed 4 times in triplicate; values represent mean±SD. Student's t-test: p<0.01 and *p<0.001. Scale bar, 100 μm.

FIG. 1E depicts representative photomicrographs of OP9 co-cultured hiPS and hES-derived cells (P4) that failed to form mouse red blood cell-filled functional human vessels in vivo upon implantation. All experiments were performed 5 times in duplicate. Scale bar, 100 μm.

FIGS. 2A-E illustrate examination of morphology, endothelial antigen expression, clonal proliferative potential, and in vitro and in vivo vessel forming potential of endothelial cells obtained from EB-mediated endothelial lineage differentiation of hES and hiPS cells.

FIG. 2A depicts representative phase contrast photomicrographs of hES and hiPS-derived EBs at day 7 of EB-mediated endothelial lineage differentiation (top panels); culture of isolated cells at P1 and P4 (middle panels); and characteristic cobblestone endothelial phenotype in human umbilical vein endothelial cells (HUVECs; bottom panels). All experiments were performed 5 times in duplicate. Scale bars, 100 μm.

FIG. 2B depicts hiPS and hES-derived cells (P4) obtained from the EB-based protocol were stained with monoclonal antibodies against human CD31, CD144 and CD146. Percentages in top panel contour plots depict CD144 and CD31 double positive cells and percentages in the bottom panel contour plots indicate CD144 and CD146 double positive cells. All experiments were performed 4 times in duplicate.

FIG. 2C depicts representative photomicrographs of EB-based hiPS and hES-derived cells (P4) that formed capillary-like networks with numerous smaller incomplete branches on Matrigel™. All experiments were performed 5 times in duplicate. Scale bar, 100 μm.

FIG. 2D depicts a bar graph showing clonal proliferative analysis of EB-based hES-derived cells (P3 to P4) compared to CB-ECFC control cells. All experiments were performed 4 times in triplicate; values represent mean±SD. Student's t-test: p<0.01 and *p<0.001.

FIG. 2E depicts representative photomicrographs of EB-based hiPS and hES-derived cells (P4) that failed to form mouse red blood cell-filled functional human vessels in vivo upon implantation. All experiments were performed 5 times in duplicate. Scale bar, 100 μm.

FIGS. 3A-E illustrate examination of morphology, endothelial antigen expression, clonal proliferative potential, and in vitro Matrigel™ network forming potential of endothelial cells obtained from EBs plus 2D-based endothelial lineage differentiation of hES cells (in the presence of TGF-beta inhibitor).

FIG. 3A is a schematic representation of endothelial lineage differentiation of hES cells in EBs plus 2D-based differentiation protocol, as previously described[24].

FIG. 3B depicts representative phase contrast photomicrographs of hES cells undergoing endothelial lineage differentiation at different days in EB plus 2D-based differentiation protocol. All experiments were performed 5 times in duplicate. Scale bar, 100 μm.

FIG. 3C depicts representative contour plots of hES cells undergoing endothelial lineage differentiation at different days in the EB plus 2D-based differentiation protocol. Cells were stained with monoclonal antibodies against various human endothelial antigens at different time points while undergoing 14 days of endothelial lineage differentiation. Percentages in contour plots indicate NRP-1 and CD31 double positive cells. All experiments were performed 5 times in duplicate.

FIG. 3D depicts representative phase contrast photomicrographs of different subsets (NRP-1$^+$CD31$^+$, NRP-1$^+$CD31$^-$, NRP-1$^-$CD31$^+$ and CD144$^+$CD146$^+$) of sorted cells derived at day 14 from hES cells undergoing endothelial lineage differentiation in the EB plus 2D-based differentiation protocol. All experiments were performed 5 times in duplicate. Scale bar, 100 μm.

FIG. 3E depicts a bar graph showing the results of a clonal proliferative analysis of EB-2D-based hES-derived various subsets (P3 to P4) in comparison with CB-ECFC control. All experiments were performed 4 times in triplicate; values represent mean±SD.

FIGS. 4A-G illustrate a one-step 2D serum-free endothelial lineage differentiation protocol provided herein that does not require EB formation or TGF-β inhibition and yields ECFC-like cells similar to CB-ECFCs.

FIG. 4A is a schematic representation of an endothelial lineage differentiation protocol for differentiating hES and hiPS cells into over a trillion ECFC-like cells in 61 days starting from 10$^4$ hES or hiPS cells, as provided herein. Generation of 3×10$^4$ hPS cells in 12 days is shown on the left. A representative flow cytometry contour plot (bottom) indicates the percent expression of NRP-1 and CD31 in day 12 differentiated cells. Day 12 NRP-1+CD31+ cells give rise to stable ECFC-like cell colonies that undergo extensive expansion.

FIG. 4B depicts bar graphs showing that day 12 differentiated cells sorted for NRP-1$^+$CD31$^+$ and NRP-1$^-$CD31$^+$ cell fractions and cultured in transitioning media for endothelial growth. All experiments were performed 6 times in triplicate and values represent mean±SD. Student's t-test: ***p<0.001.

FIG. 4C is a representative photomicrograph of an ECFC-like cell colony obtained from an NRP-1$^+$CD31$^+$ cell fraction that exhibited characteristic cobblestone morphology and contained a homogenous population of endothelial cells within each colony. Experiments were performed 8 times in duplicates. Scale bars, 50 μm.

FIG. 4D depicts representative immunofluorescence micrographs of ECFC-like cells exhibiting cell surface expression for typical endothelial markers CD31, CD144 and NRP-1 and not the non-endothelial marker α-SMA. In the left panel, NRP-1 expression is represented in green; CD31 expression is represented in red. In the right panel, α-SMA expression is represented in green; CD144 expression is represented in red. DAPI was used to stain the nucleus in blue. All experiments were performed 3 times in duplicates.

FIG. 4E is a bar graph that represents clonal proliferative analysis of hES- and hiPS-derived ECFC-like cells in comparison with CB-ECFC control. All experiments were performed 4 times in triplicate and values represent mean±SD.

FIG. 4F depicts representative phase contrast photomicrographs illustrating the iPS-derived ECFC-like cell's ability to display characteristic cobblestone morphology and to form complete capillary-like networks on Matrigel™, similar to that exhibited by CB-ECFCs. All experiments were performed 5 times in duplicate. Scale bar, 100 μm.

FIG. 4G illustrates that ECFC-like cells form durable and functional in vivo human vessels in immunodeficient mice. Arrows in the representative photomicrograph depict anti-human CD31$^+$ stained functional human blood vessels that are perfused with circulating host murine red blood cells. Scale bar, 50 μm. A bar graph (bottom) represents quantification of functional hCD31$^+$ vessels counted per mm$^2$ in each group. All experiments were performed 6 times in triplicates and values represent mean±SD. Student's t-test: p=ns. Scale bar, 50 μm.

FIGS. 6A-E illustrate that NRP-1$^-$CD31$^+$ cells do not exhibit ECFC properties.

FIG. 6A depicts a representative photomicrograph of an endothelial colony obtained from NRP-1$^-$CD31$^+$ cells exhibiting heterogeneous morphologies. Experiments were performed 8 times in duplicate. Scale bar, 100 μm.

FIG. 6B depicts a representative immunofluorescence micrograph of NRP-1 CD31$^+$ cells exhibiting predominant expression of the non-endothelial marker α-SMA with few cells expressing the endothelial surface marker CD144. CD144 expression represented in red; α-SMA expression represented in green; and DAPI was used to stain the nucleus in blue. Experiments were performed 4 times in duplicate. Scale bar, 100 μm.

FIG. 6C depicts a representative photomicrograph of NRP-1$^-$CD31$^+$ cells exhibiting the inability to form murine red blood cell-filled functional human vessels in vivo upon implantation. Instead, the NRP-1$^-$CD31$^+$ cells formed small lumens with no RBCs (indicated by arrow) suggesting a defect in inosculation. All experiments were performed 5 times in duplicate. Scale bar, 100 μm.

FIG. 6D depicts a representative phase contrast photomicrograph of NRP-1 CD31$^+$ cells exhibiting formation of incomplete capillary-like networks on Matrigel™. All experiments were performed 5 times in duplicate. Scale bar, 100 μm.

FIG. 6E depicts a bar graph showing the results of clonal proliferative analysis of hiPS-derived NRP-1$^-$CD31$^+$ and NRP-1$^+$CD31$^+$ cells compared to single plated CB-ECFC control. All experiments were performed 4 times in triplicate; values represent mean±SD. Student's t-test: ***p<0.001.

FIGS. 7A-D illustrate that NRP-1$^+$CD31$^+$ cells that give rise to a stable ECFC-like phenotype begin to appear at day 9 of differentiation and a significant increase in the emergence of NRP-1$^+$CD31$^+$ cells that give rise to a stable ECFC-like cell occurs at day 12 of differentiation.

FIG. 7A depicts a bar chart illustrating that the percentage of emerging NRP-1$^+$CD31$^+$ cells derived from human iPS cells using the ECFC-like cell protocol provided herein at days 6, 9 and ay 12 of differentiation. All experiments were performed 4 times in duplicate. Values represent mean±SD. Student's t-test: ***p<0.001.

FIG. 7B depicts representative photomicrographs of endothelial colonies obtained from hiPS-derived NRP-1$^+$CD31$^+$ cells examined at days 6, 9 and 12 of differentiation. Day 12-derived NRP-1$^+$CD31$^+$ cells exhibited cobblestone morphology and contained a homogenous population of endothelial cells within each colony. All experiments were performed 8 times in duplicate. Scale bar, 50 μm.

FIG. 7C depicts representative contour plots of an hiPS-derived NRP-1$^+$CD31$^+$ cell fraction obtained using the ECFC-like cell protocol provided herein at days 6, 9 and 12 of differentiation. The percentages shown in the contour plots indicate CD144 and CD31 double positive cells. All experiments were performed 4 times in duplicate.

FIG. 7D depicts representative phase contrast photomicrographs showing Matrigel™ network forming potential. All experiments were performed 5 times in duplicate. Scale bar, 100 μm.

FIGS. 8A-E illustrate examination of morphology, endothelial antigen expression, and in vitro Matrigel™ network forming potential of hES-derived endothelial cells obtained from ECFC-like cell differentiation protocol provided herein.

FIG. 8A depicts representative phase contrast photomicrographs of hiPS cells undergoing endothelial lineage differentiation at different days in the ECFC-like cell differentiation protocol provided herein. Human iPS cells in 2D culture grew to form colonies of cells with endothelial like morphology (at days 6 and 9) and became confluent by day 12. Experiments were performed 8 times in duplicate. Scale bar, 100 μm.

FIG. 8B depicts representative immunofluorescence micrographs of cells undergoing ECFC-like cell differentiation at different days exhibiting cell surface expression for the typical endothelial markers CD31, CD144 and NRP-1 and not the non-endothelial marker α-SMA. NRP-1$^+$CD31$^+$ cells emerged as a cluster of cells within the mass of differentiating cells and completely lacked α-SMA expression at day 12. NRP-1 expression represented in green; CD31 expression represented in red; α-SMA expression represented in green; CD144 expression represented in red; and DAPI was used to stain the nucleus in blue. Experiments were performed 4 times in duplicate. Scale bars, 50 μm.

FIG. 8C depicts representative photomicrographs of endothelial colonies obtained from hiPS-derived NRP-1$^+$CD31$^+$ cell fraction examined at days 6, 9 and 12. Day 12-derived NRP-1$^+$CD31$^+$ cells exhibited characteristic cobblestone morphology containing a homogenous population of endothelial cells within each colony. All experiments were performed 8 times in duplicate. Scale bar, 50 µm.

FIG. 8D depicts representative contour plots of the hiPS-derived NRP-1$^+$CD31$^+$ cell fraction obtained using the ECFC-like cell protocol at days 6, 9 and 12. NRP-1$^+$CD31$^+$ cells derived at different days were cultured in endothelial growth media and formed confluent monolayers of cells. These cells were stained with monoclonal antibodies against human CD31 and CD144 endothelial antigens to examine for typical endothelial gene co-expression. The percentages indicated in the contour plots indicate CD144 and CD31 double positive cells. The highest percentage of cells co-expressing CD144 and CD31 appeared from NRP-1$^+$CD31$^+$ cells derived on day 12. All experiments were performed 5 times in duplicates.

FIG. 8E depicts representative phase contrast photomicrographs showing Matrigel™ network forming potential. Human iPS-derived NRP-1$^+$CD31$^+$ cell fractions were obtained using the ECFC-like cell protocol at days 6, 9 and 12 of ECFC-like cell differentiation protocol. After culturing and expanding NRP-1$^+$CD31$^+$ cells from each of these days, in vitro capillary-like network formation assay was performed on Matrigel™ coated dishes. While day 6-derived cells formed incomplete capillary-like networks upon plating on Matrigel™, day 9- and day 12-derived cells formed complete capillary-like networks. All experiments were performed 4 times in duplicate. Scale bar, 100 µm.

FIGS. 9A-E illustrate examination of morphology, endothelial antigen expression, and in vitro Matrigel™ network forming potential of hES-derived endothelial cells obtained from the ECFC-like cell differentiation protocol provided herein.

FIG. 9A depicts representative phase contrast photomicrographs of hES cells undergoing endothelial lineage differentiation at different days in the ECFC-like cell differentiation protocol. All experiments were performed 8 times in duplicate. Scale bar, 100 µm.

FIG. 9B depicts representative immunofluorescence micrographs of cells undergoing ECFC-like cell differentiation at different days exhibiting cell surface expression of the typical endothelial markers CD31, CD144 and NRP-1 and not the non-endothelial marker α-SMA. NRP-1$^+$CD31$^+$ cells emerge as a cluster of cells within the mass of differentiating cells and completely lack α-SMA expression at day 12. NRP-1 expression represented in green; CD31 expression represented in red; α-SMA expression represented in green; CD144 expression represented in red; and DAPI was used to stain the nucleus in blue. All experiments were performed 4 times in duplicate. Scale bars, 100 µm.

FIG. 9C depicts representative photomicrographs of endothelial colonies obtained from hES-derived NRP-1$^+$CD31$^+$ cells examined at days 6, 9 and 12 of differentiation. All experiments were performed 8 times in duplicate. Scale bar, 50 µm.

FIG. 9D depicts representative contour plots of hES-derived NRP-1$^+$CD31$^+$ cell fraction obtained using the ECFC-like cell protocol at days 6, 9 and 12. NRP-1$^+$CD31$^+$ cells derived at different days were cultured in endothelial growth media and formed confluent monolayers of cells. The percentages in contour plots indicate CD144 and CD31 double positive cells. All experiments were performed 4 times in duplicate.

FIG. 9E depicts representative phase contrast photomicrographs showing Matrigel™ network forming potential. All experiments were performed 5 times in duplicate. Scale bar, 100 µm.

FIGS. 10A-F depict how hiPSC-derived ECFC-like cells contribute to vascular repair of both ischemic retina and limb in pre-clinical animal models of human disease.

FIG. 10A depicts representative flat-mounted retinas of C57/BL6 mice injected with vehicle (left) or hiPSC-derived ECFC-like cells (right). Retinal vasculature stained in green with isolectin B4. Avascular area indicated by white line. All experiments were performed ≥4 times and percentage of avascular area calculated. Scale bars, 1 mm.

FIG. 10B depicts representative flat-mounted retinas of C57/BL6 mice injected with vehicle (left) or hiPSC-EBT-CD144+ ECs (right). Retinal vasculature stained in green with Isolectin B4. Avascular area indicated by white line. All experiments were performed ≥4 times and percentage of avascular area calculated. Scale bars, 1 mm.

FIG. 10C depicts representative pathological preretinal neovascularisation in C57/BL6 mice injected with vehicle (left) or hiPSC-derived ECFC-like cells (right). Preretinal neovascular tufts predominately seen in vehicle-injected eyes when compared to contra lateral hiPSC-derived ECFCs-like cell-injected eyes. Arrows indicate preretinal neovascular tufts. All experiments were performed ≥4 times. Scale bars, 200 µm.

FIG. 10D depicts representative laser Doppler perfusion imaging showing therapeutic neovascularization by hiPSC-derived ECFC-like cells in athymic nude mice. A greater increase in limb blood perfusion was observed in the ischemic limbs (arrow) of mice that received hiPSC derived ECFC-like cells or CB-ECFCs transplantation than in the vehicle or hiPSC-EBT-CD144+ ECs-injection groups. All experiments were performed ≥10 times.

FIG. 10E depicts a stacked bar graph represents the percentage distribution of the physiological status of the instrumented ischemic limbs on day 28 post-implantation of vehicle, hiPSC-derived ECFC-like cells, hiPSC-EBT-CD144+ ECs or CB-ECFCs. All experiments were performed ≥10 times.

FIG. 10F depicts a table representing the physiological status of the ischemic limbs on day 28 post-implantation of vehicle, hiPSC-derived ECFC-like cells, hiPSC-EBT-CD144+ ECs or CB-ECFCs. All experiments were performed ≥10 times and values represent percentage limb salvage, necrosis or loss. Parametric Chi-squared test: *P<0.05.

FIG. 11A depicts hiPSC-derived ECFC-like cells (top right) or hiPSC-EBT-CD144+ ECs (top left) that were labeled in red with quantum dots and injected into ischemic retinas and subsequently incorporated into the resident vasculature (stained green with isolectin B4). hiPSC-derived ECFC-like cells integrate in higher numbers and wider distribution in host retinas when compared to hiPSC-EBT-CD144+ ECs. All experiments were performed ≥4 times. Scale bars, 50 µm.

FIG. 11B depicts red quantum dot labelled hiPSC-derived ECFC-like cells that are present in close association with host vasculature as single cells and also appear to form vascular tube like structures in the superficial retinal plexus. All experiments were performed ≥4 times. Scale bars, 25 µm.

FIGS. 12A-D illustrate hiPS-derived CD31$^+$NRP-1$^+$ ECFC-like cells undergo extensive expansion, maintain stable endothelial phenotype, and exhibit characteristics of primary cells by ultimately becoming senescent after long term culture.

FIG. 12A depicts representative phase contrast photomicrographs of CB-ECFCs showing β-galactosidase staining. CB-ECFCs were stained with β-galactosidase as per manufacturer's instruction. CB-ECFCs exhibited few β-galactosidase positive blue cells (indicated by circles) at P7 but by P18 almost all of these cells were positive for β-galactosidase blue staining. All experiments were performed 8 times in duplicate. Scale bar, 50 μm.

FIG. 12B depicts representative phase contrast photomicrographs of hiPS-derived ECFC-like cells showing β-galactosidase staining. hiPS ECFC-like cells were stained with β-galactosidase as per manufacturer's instruction. hiPS-derived ECFC-like cells exhibited few β-galactosidase positive blue cells (indicated by circles) at P7 but by P18 almost all of these cells were positive for β-galactosidase blue staining. All experiments were performed 4 times in duplicate. Scale bar, 50 μm.

FIG. 12C depicts a bar graph showing the percentages of β-galactosidase positive cells in CB-ECFCs and hiPS-derived ECFC-like cells from different passages. All experiments were performed 4 times in triplicate; values represent mean±SD. Student's t-test: ***$p<0.001$.

FIG. 12D depicts representative immunofluorescence micrographs of hiPS-derived ECFC-like cells displaying expression of the endothelial markers CD31, CD144 and NRP-1 and not the non-endothelial marker α-SMA. In the top panel, NRP-1 expression is represented in green; CD31 expression is represented in red. In the bottom panel, α-SMA expression is represented in green; CD144 expression is represented in red. DAPI was used to stain the nucleus in blue. All experiments were performed 3 times in duplicate. Scale bars, 100 μm.

FIG. 13A depicts a heatmap of relative transcriptional levels for a select group of genes defining individual germ layers and specific lineages.

FIG. 13B depicts heatmaps of relative transcriptional levels for a select group of vascular, angiocrine, and non-vascular genes, as previously described[32]. Human iPS-derived ECFC-like cells and hES-derived ECFC-like cells exhibited high expression profiles for many vascular (top panel) and angiocrine (middle panel) genes and decreased expression for non-vascular genes (bottom panel), similar to that exhibited by CB-ECFCs.

FIGS. 14A-E depicts full length western blots showing KDR, p130$^{Cas}$ and Pyk phosphorylation.

FIG. 14A depicts a western blot that was first prepared with phospho-KDR antibody to identify phosphorylated KDR.

FIG. 14B depicts a western blot that was first prepared with phospho-KDR antibody and then stripped to incubate with total KDR antibody.

FIG. 14C depicts a western blot that was prepared with phospho-p130$^{Cas}$.

FIG. 14D depicts a western blot that was first prepared with phosphr-p130$^{Cas}$ and then stripped to re-incubate with phospho-Pyk2 antibody.

FIG. 14E depicts a western blot that was first prepared with phospho-p130$^{Cas}$ and then stripped to re-incubate with total phospho-Pyk2 antibody.

FIGS. 15A-C illustrate that NRP-1 is critical for the emergence of ECFC-like cells from hiPS cells.

FIG. 15A is a schematic representation of the treatment strategy used to examine the role of NRP-1 in the emergence of ECFC-like cells from hiPS cells.

FIG. 15B is a line graph representing quantification of the percentage emergence of NRP-1$^+$CD31 (double) positive cells following treatment with control (blue), Fc-NRP-1 (red) and NRP-b (green) after 4 and 6 days of treatment. In the insert, a flow cytometry contour plot indicates the percent expression of KDR and NRP-1 in day 6 differentiated cells showing abundant KDR expression and diminished NRP-1 expression. All experiments were performed 6 times in triplicate; values represent mean±SD. Student's t-test: $p<0.01$ and *$p<0.001$.

FIG. 15C depicts Western blots showing KDR, p130$^{Cas}$ and Pyk2 phosphorylation. All experiments were performed 4 times in duplicates.

FIGS. 16A-I illustrate that NRP-1 is critical for the maintenance of ECFC-like cell proliferative potential.

FIG. 16A depicts hiPS-derived ECFC-like cells from different passages (P4, P14 and P18) that were stained with monoclonal antibodies against CD31, CD144 and NRP-1. Percentages in each contour plot indicate CD31 and CD144 double positive cells (left panel), while percentages in the right panel contour plot indicate CD31 and NRP-1 double positive cells. All experiments were performed 4 times in duplicate.

FIG. 16B depicts fold expansion of hiPS-derived ECFC-like cells when counted at different passages (P4, P14 and P18) after 7 days of culture. All experiments were performed 3 times in triplicate; values represent mean±SD. Student's t-test: ***$p<0.001$.

FIG. 16C depicts passage 14 hiPS-derived ECFC-like cells that were stained with monoclonal antibodies against KDR and NRP-1. Percentages in each contour plot indicate NRP-1 and KDR positive cells. All experiments were performed 4 times in duplicate.

FIG. 16D depicts late passage (P14) hiPS-derived ECFC-like cells that were treated with control, Fc-NRP-1 and NRP-1-B in order to allow examination of fold expansion after 3 or 7 days of treatment. Bar graphs represent fold expansion of (P14) hiPS-derived ECFC-like cells following 3 days (left bar graph) and 7 days (right bar graph) of treatment with control, Fc-NRP-1 and NRP-1-B. All experiments were performed 5 times in triplicate; values represent mean±SD. Student's t-test: *$p<0.05$, $p<0.01$ and *$p<0.001$.

FIG. 16E depicts late passage (P14) hiPS-derived ECFC-like cells that were treated with control, Fc-NRP-1 and NRP-1-B for 7 days and were stained with β-galactosidase, as per manufacturer's instruction. Circles represent β-galactosidase positively stained cells. Fc-NRP-1 treatment decreased the number of β-galactosidase positive blue cells (dotted circles) compared to control-treated cells. NRP-1-B treatment increased the number of blue cells compared to control. All experiments were performed 4 times in triplicate. Scale bar, 50 μm.

FIG. 16F depicts a bar graph representing percentages of β-galactosidase positive blue cells following the treatment of late passage (P14) hiPS-ECFC like cells with control, Fc-NRP-1 and NRP-1-B for 7 days. All experiments were performed 4 times in triplicate; values represent mean±SD. Student's t-test: $p<0.01$ and *$p<0.001$.

FIG. 16G depicts late passage (P14) hiPS-derived ECFC-like cells that were cultured in regular EGM-2 media containing VEGF165 and EGM-2 media with VEGF121 and treated with control, Fc-NRP-1 and NRP-1-B for 7 days. After 7 days, cells were collected, counted and stained with propidium iodide and annexin V to examine for live, proapoptotic, and dead cells in each of these treatment groups. A bar graph represents the percentage of proapoptotic cells in VEGF165 and VEGF121 containing media following 7 days of treatment with control, Fc-NRP-1 and NRP-1-B. A significantly decreased percentage of pro-apoptotic cells were observed in both Fc-NRP-1 and NRP-1-B treated groups in cells cultured in VEGF165 containing media compared to cells cultured in the presence of VEGF121. All experiments were performed 4 times in triplicate; values represent mean±SD. Student's t-test: **p<0.01.

FIG. 16H depicts late passage (P14) hiPS-derived ECFC-like cells that were cultured in EGM-2 media wherein regular VEGF$_{165}$ was replaced with VEGF$_{121}$. These cells were treated with control, Fc-NRP-1 or NRP-1-B for 7 days. A bar graph represents fold expansion of P14 hiPS-derived ECFC-like cells in VEGF$_{121}$ treated media following 7 days of treatment with control, Fc-NRP-1 and NRP-1-B. Fc-NRP-1 or NRP-1-B treatment did not cause significant alteration in fold expansion in these cells compared to control in the presence of VEGF$_{121}$. All experiments were performed 4 times in triplicate; values represent mean±SD.

FIG. 16I depicts late passage (P14) hiPS-derived ECFC-like cells that were cultured in regular EGM-2 media containing VEGF$_{165}$ and EGM-2 media with VEGF$_{121}$. These cells were treated with control, Fc-NRP-1 and NRP-1-B for 7 days. After 7 days, cells were collected, counted and stained with propidium iodide and annexin V to examine for live, proapoptotic, and dead cells in each of these treatment groups. Percentages in each contour plots represent live, proapoptotic, and dead cells in control (left panels), Fc-NRP-1 (middle panels) and NRP-B (right panels) treated cells in the presence of VEGF$_{121}$ (panels on top row) or VEGF$_{165}$ (panels on bottom row). In the VEGF$_{121}$-treated cells, both Fc-NRP-1 and NRP-1-B increased the percentage of dead and pro-apoptotic cells compared to control. However, in VEGF$_{165}$s-treated cells, while Fc-NRP-1 decreased the percentages of both dead and proapoptotic cells and increased the percentage of live cells compared to control, NRP-1-B increased the percentages of both dead and pro-apoptotic cells and decreased the percentage of live cells compared to control. All experiments were performed 4 times in triplicate; a representative contour plot is shown for each group.

FIGS. 17A-N illustrate PAD patients derived ECs possess diminished NRP-1 expression, undergo early cell senescence, fail to exhibit a complete hierarchy of clonal proliferative potential and have deficient in vivo vessel forming ability, however, exogenous NRP-1 treatment in PAD ECs decreases cell senescence, reduces multi nuclear cell formation and rescues PAD-EC proliferative potential.

FIG. 17A depicts artery and peripheral blood ECs that were derived from patients with peripheral vascular disease who underwent lower extremity amputations. A representative phase contrast photomicrograph indicates the homogenous characteristic cobblestone morphology of endothelial cells derived from PB (left panel) and artery (right panel) obtained from patients with PAD and CLI. All experiments were performed 6 times in duplicate. Scale bar, 50 μm.

FIG. 17B depicts ECs derived from PAD patients that were subjected to flow cytometric analysis to determine expression of typical endothelial markers. PAD patient artery or PB derived endothelial cells were stained with monoclonal antibodies against human CD31, CD144, KDR and NRP-1. The percentage indicated in the upper right quadrant of contour plots indicates CD31 and CD144 double positive cells (left contour plot). Percentages in right contour plots indicate the percentage of cells co-expressing NRP-1 and KDR (upper right); NRP-1 expression (upper Left); KDR expression in lower right. While all of these cells maintained high levels of co-expression for CD31 and CD144 and more than 60% of the cells exhibited KDR expression, less than 10% of cells exhibited NRP-1 expression. All experiments were performed 5 times in triplicate.

FIG. 17C depicts representative immunofluorescence micrographs of hiPS-derived ECFC-like cells and PAD artery ECs indicating surface expression for endothelial markers CD31, CD144, NRP-1 and the non-endothelial marker α-SMA. In top panels, NRP-1 expression represented in green; CD31 expression represented in red. In bottom panels, α-SMA expression represented in green; CD144 expression represented in red. DAPI was used to stain the nucleus in blue. While hiPS ECFC-like cells exhibited NRP-1 and CD31 co-expression, stained positive for CD144 and completely lacked α-SMA expression, PAD-artery-ECs did not exhibit NRP-1 and CD31 co-expression, however, they did stain positive for CD31 and CD144, and completely lacked α-SMA expression. All experiments were performed 4 times in duplicate. Scale bars, 100 μm.

FIG. 17D depicts CB-ECFCs, hiPS-derived ECFC-like cells and ECs derived from PAD patients that were subjected to single cell proliferative potential assays. Single cells from each of these groups were plated in 96-well plates and scored after 14 days of plating. Endothelial cells from PAD patients exhibited poor proliferative behavior as about 70% of resident vessel wall (artery) and more than 30% of PB derived endothelial cells remained as a single non dividing cell. In contrast only 2% of the single plated cells in CB-ECFCs and hiPS-derived ECFC-like cell groups remained as non-dividing cells after 14 days of culture. Those PAD derived cells that divided mostly formed endothelial clusters (28% PAD-artery-ECs and 60% PAD-PB-ECs), few formed LPP-ECFC (0.5% PAD-artery-ECs and 4% PAD-PB-ECs) and none of them gave rise to HPP-ECFC. However, cells from CB-ECFCs and hiPS-derived ECFC-like cells groups that divided formed few endothelial clusters and mostly formed LPP-ECFCs (44.3% CB-ECFCs and 44.7% hiPS ECFC-like cells) and HPP-ECFCs (35% CB-ECFCs and 43% hiPS-derived ECFC-like cells). All experiments were performed 4 times in triplicate. Student's t-test: ***p<0.001.

FIG. 17E depicts representative phase contrast photomicrographs of PAD patient derived ECs from artery and peripheral blood demonstrating the ability to form capillary-like networks on Matrigel™. All experiments were performed 5 times in duplicate. Scale bar, 100 μm.

FIG. 17F depicts ECs derived from PAD patients that were implanted in immunodeficient mice. Gels were recovered after 14 days of implantation, fixed, permeabilized and stained with specific anti-human CD31 antibody that does not cross react with mouse host cells. Arrows indicated in a representative photomicrograph identify a few small anti-human CD31$^+$ blood vessels that are perfused with circulating host red blood cells. All experiments were performed 5 times in triplicate. Scale bar, 50 μm.

FIG. 17G depicts a bar graph representing quantification of functional hCD31$^+$ vessels counted per mm$^2$ in each group. ECs derived from PAD patients exhibited a significantly diminished number of functional hCD31 vessels compared to the CB-ECFC control. All experiments were performed 5 times in triplicate; values represent mean±SD. Student's t-test: ***p<0.001.

FIG. 17H depicts PAD-ECs and hiPS-derived ECFC-like cells (P7) that were stained with β-galactosidase as per manufacturer instructions. Almost all cells were β-galactosidase positive blue cells in the PAD-EC group, whereas fewer cells were (indicated by circles) β-galactosidase positive in the hiPS-derived ECFC-like cell group. All experiments were performed 4 times in triplicate. Scale bar, 50 μm.

FIG. 17I depicts a bar graph showing the percentages of β-galactosidase positive PAD ECs compared to hiPS-derived ECFC-like cells. A significantly higher percentage of β-galactosidase positive blue cells were observed in PAD-ECs compared to hiPS-derived ECFC-like cells. All experiments were performed 4 times in triplicate; values represent mean±SD. Student's t-test: ***p<0.001.

FIG. 17J depicts PAD-artery ECs (P7) that were treated with control, Fc-NRP-1 and NRP-1-B for 7 days. A bar graph represents fold expansion of PAD-artery ECs following 7 days of treatments with control, Fc-NRP-1 and NRP-1-B. While a significantly higher fold expansion was observed in Fc-NRP-1 treated group compared to control, a significantly decreased expansion was observed in NRP-1-B treated group compared to the control group. All experiments were performed 4 times in triplicate; values represent mean±SD. Student's t-test: p<0.01 and *p<0.001.

FIG. 17K PAD-artery ECs (P7) were treated with control, Fc-NRP-1 and NRP-1-B for 7 days and were stained with β-galactosidase as per manufacturer's instruction. Almost all cells stained positive for β-galactosidase staining in the control and NRP-1-B treated groups, whereas some cells in the Fc-NRP-1 treated group did not stain positive for β-galactosidase staining (indicated by circles). All experiments were performed 4 times in triplicate. Scale bar, 50 μm.

FIG. 17L depicts a bar graph indicating the percentages of β-galactosidase positive cells following the treatment of PAD-artery endothelial cells with control, Fc-NRP-1 and NRP-1-B for 7 days. Significantly decreased β-galactosidase positive blue cells were observed in Fc-NRP-1 treated cells compared to control treated cells. All experiments were performed 4 times in triplicate; values represent mean±SD. Student's t-test: *p<0.05 and ***p<0.001.

FIG. 17M depicts PAD-artery ECs (P7) that were treated with control and Fc-NRP-1 for 7 days and photomicrographs of the cells obtained to count nuclei numbers in treated cells. A representative photomicrograph with arrows indicating multinucleated blue cells in control (left panel) and circles indicating non-blue cells with a single nucleus (right panel). All experiments were performed 4 times in triplicate. Scale bar, 25 μm.

FIG. 17N depicts a bar graph indicating the percentage of multi-nucleated PAD ECs in control compared to Fc-NRP-1 treated cells. A significantly reduced percentage of multi-nucleated cells were observed in Fc-NRP-1 treated cells compared to control treated cells. All experiments were performed 4 times in triplicate; values represent mean±SD. Student's t-test: ***p<0.001.

DETAILED DESCRIPTION OF THE DISCLOSURE

Figure 3E:
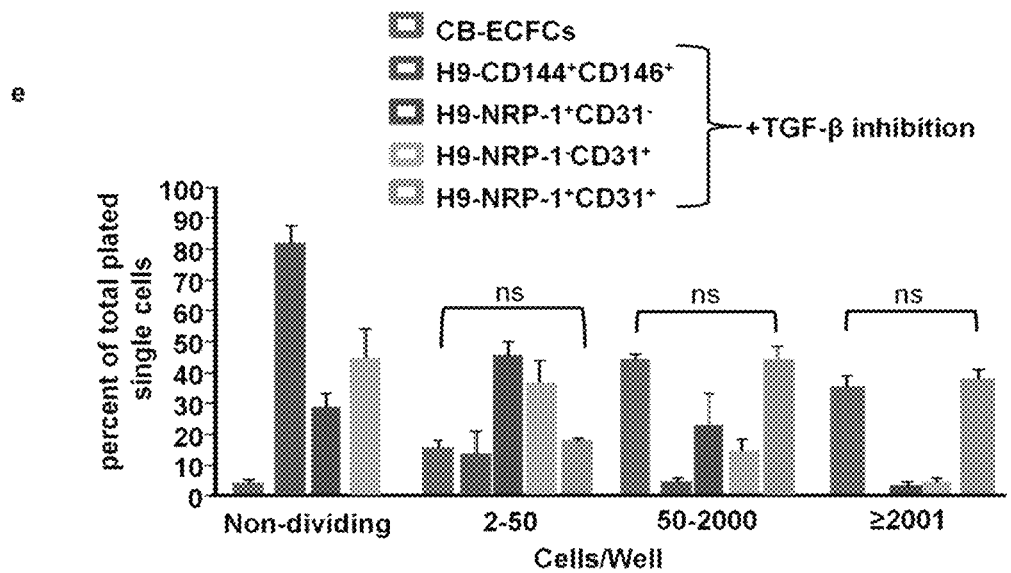

The present disclosure generally relates to methods for in vitro differentiation of pluripotent cells, such as, for example, human embryonic stem cells (hESC) or induced pluripotent stem cells (iPSC) (collectively, human pluripotent stem cells (hPSCs)), into endothelial colony forming cell-like cells (ECFC-like cells). In various embodiments of the method provided herein, pluripotent cells may be maintained, expanded, and differentiated under defined conditions, wherein the use of feeder cells and/or serum is not required. In one embodiment, the resulting ECFC-like cells may be further grown into blood vessels in vivo in the absence of co-culture and/or co-implantation cells.

In various embodiments, ECFC-like cells generated using the method disclosed herein have high proliferative potential (HPP) relative to endothelial cells (ECs) derived in vitro from hES or hiPS cells via co-culture with cells, such as OP9, or embryoid body (EB) formation. In one embodiment, ECFC-like cells generated using the method disclosed herein have proliferative potential that is greater than or equal to that of ECFCs isolated from human cord blood. In one embodiment, the methods disclosed herein can be used to reproducibly generate from each calculated stem cell at least $1 \times 10^8$ ECFC-like cells.

I: Definitions

The definitions of certain terms as used in this specification are provided below. Unless defined otherwise, all technical and scientific terms used herein generally have the same meaning as commonly understood by one of ordinary skill in the art to which this disclosure belongs.

As used herein, "endothelial colony forming cell" and "ECFC" refer to primary endothelial cells found in the blood that display the potential to proliferate and form an endothelial colony from a single cell and have a capacity to form blood vessels in vivo in the absence of co-implanted or co-cultured cells.

As used herein, "cord blood ECFC" and "CB-ECFC" refer to primary ECFCs that are derived from umbilical cord blood.

As used herein, "endothelial colony forming cell-like cell" and "ECFC-like cell" refer to non-primary endothelial cells that are generated in vitro from human pluripotent stem cells (hPSCs). ECFC-like cells have various characteristics of ECFCs, at least including the potential to proliferate and form an endothelial colony from a single cell and have a capacity to form blood vessels in vivo in the absence of co-implanted or co-cultured cells.

As used herein, the terms "proliferation potential" and "proliferative potential" refer to the capacity of a cell to divide when provided appropriate growth promoting signals.

As used herein, the terms "high proliferation potential", "high proliferative potential" and "HPP" refer to the capacity of a single cell to divide into more than about 2000 cells in a 14 day cell culture. Preferably, HPP cells have a capacity to self-replenish. For example, the HPP-ECFC-like cells provided herein have a capacity to self-replenish, meaning that an HPP-ECFC-like cell can give rise to one or more HPP-ECFC-like cells within a secondary HPP-ECFC-like colony when replated in vitro. In some embodiments, HPP-ECFC-like cells may also have the ability to give rise to one or more of LPP-ECFC-like cells and ECFC-like cell clusters within a secondary HPP-ECFC-like colony when replated in vitro.

As used herein, the terms "low proliferation potential" "low proliferative potential" and "LPP" refer to the capacity of a single cell to divide into about 51-2000 cells in a 14 day cell culture. In some embodiments, LPP-ECFC-like cells may also have the ability to give rise to ECFC-like cell clusters. However, LPP-ECFC-like cells do not have a capacity to give rise to secondary LPP-ECFC-like cells or HPP-ECFC-like cells.

As used herein, the term "ECFC-like cluster" refers to a cluster of ECFC-like cells having a capacity to divide into about 2-50 cells in a 14 day cell culture.

As used herein, "pluripotent cell" refers to a cell that has the potential to differentiate into any cell type, for example, cells of any one of the three germ layers: endoderm, mesoderm, or ectoderm.

As used herein, "embryonic stem cells", "ES cells" or "ESCs" refer to pluripotent stem cells derived from early embryos.

As used herein, "induced pluripotent stem cells," "iPS cells" or "iPSCs" refer to a type of pluripotent stem cell that has been prepared from a non-pluripotent cell, such as, for example, an adult somatic cell, or a terminally differentiated cell, such as, for example, a fibroblast, a hematopoietic cell, a myocyte, a neuron, an epidermal cell, or the like, by introducing into the non-pluripotent cell or contacting the non-pluripotent cell with one or more reprogramming factors.

As used herein, "endothelial differentiation medium" refers to any nutrient medium that supports and/or enhances differentiation of pluripotent cells into cells of the endothelial lineage.

As used herein, "endothelial growth medium" refers to any medium that is suitable for maintaining cells of the endothelial lineage.

II: Methods of Differentiating Pluripotent Cells into Endothelial Colony Forming Cell-Like Cells (ECFC-Like Cells)

In an aspect, the method provided herein involved at least three steps:

A: providing pluripotent stem cells;
B: inducing differentiation of the pluripotent stem cells into cells of the endothelial lineage; and
C: isolating ECFC-like cells from the differentiated cells of the endothelial lineage.

In various embodiments, the method includes a further step of:

D. expanding the isolated ECFC-like cells.

Each step in the aforementioned method is described further herein below. Various embodiments of the method provided herein may be referred to as the "ECFC-like protocol", the "ECFC-like cell protocol", the "hESC-derived ECFC-like cell protocol" or the "hiPSC-derived ECFC-like cell protocol".

A. Pluripotent Stem Cell Culture

In one aspect, a method for generating an isolated population of ECFCs in vitro from pluripotent cells is provided. Pluripotent cells that are suitable for use in the methods of the present disclosure can be obtained from a variety of sources. For example, one type of suitable pluripotent cell is an embryonic stem (ES) cell derived from the inner cell mass of a blastocyst. Methods for obtaining various types of ES cells, such as mouse, rhesus monkey, common marmoset, and human, are well known. The source of ES cells used in the method may be, for example, one or more established ES cell lines. Various ES cell lines are known and the conditions for their growth and propagation have been defined. It is contemplated herein that virtually any ES cell or ES cell line may be used with the methods disclosed herein. In one embodiment, the pluripotent cell is an induced pluripotent stem (iPS) cell derived by reprogramming somatic cells. Induced pluripotent stem cells have been obtained by various known methods. It is contemplated herein that virtually any iPS cell or cell line may be used with the methods disclosed herein. In other embodiments, the pluripotent cell is an embryonic stem cell derived by somatic cell nuclear transfer, in which a donor nucleus is transferred into a spindle-free oocyte. Various methods for producing stem cells by nuclear transfer are known. It is contemplated herein that virtually any ES cells or cell line derived by somatic cell nuclear transfer may be used with the methods disclosed herein.

In one embodiment, pluripotent cells are cultured under conditions suitable for maintaining pluripotent cells in an undifferentiated state. Methods for maintaining pluripotent cells in vitro, i.e., in an undifferentiated state, are well known. In one embodiment, pluripotent cells are cultured for about two days under conditions suitable for maintaining pluripotent cells in an undifferentiated state. For example, in the Examples below, hES and hiPS cells were maintained in mTeSR1 complete medium on Matrigel™ in 10 $cm^2$ tissue culture dishes at 37° C. and 5% $CO_2$ for about two days.

Additional and/or alternative methods for culturing and/or maintaining pluripotent cells may be used. For example, as the basal culture medium, any of TeSR, mTeSR1 alpha.MEM, BME, BGJb, CMRL 1066, DMEM, Eagle MEM, Fischer's media, Glasgow MEM, Ham, IMDM, Improved MEM Zinc Option, Medium 199 and RPMI 1640, or combinations thereof, may be used for culturing and or maintaining pluripotent cells.

The pluripotent cell culture medium used may contain serum or it may be serum-free. Serum-free refers to a medium comprising no unprocessed or unpurified serum. Serum-free media can include purified blood-derived components or animal tissue-derived components, such as, for example, growth factors. The pluripotent cell medium used may contain one or more alternatives to serum, such as, for example, knockout Serum Replacement (KSR), chemically-defined lipid concentrated (Gibco) or glutamax (Gibco).

Methods for splitting or passaging pluripotent cells are well known. For example, in the Examples below, after pluripotent cells were plated, medium was changed on days 2, 3, and 4 and cells were passaged on day 5. Generally, once a culture container is full (i.e., 70-100% confluence), the cell mass in the container is split into aggregated cells or single cells by any method suitable for dissociation and the aggregated or single cells are transferred into new culture containers for passaging. Cell "passaging" or "splitting" is a well-known technique for keeping cells alive and growing cells in vitro for extended periods of time.

B. Directed Differentiation of Pluripotent Cells into Cells of the Endothelial Lineage.

In one aspect of the method disclosed, in vitro pluripotent cells are induced to undergo endothelial differentiation. Various methods, including culture conditions, for inducing differentiation of pluripotent cells into cells of the endothelial lineage are known in the art. In the ECFC-like cell protocol provided herein it is preferable to induce differentiation of pluripotent cells in a chemically defined medium. For example, Stemline II serum-free hematopoietic expansion medium can be used as a basal endothelial differentiation medium. In the ECFC-like cell protocol provided herein various growth factors are used to promote differentiation of pluripotent cells into cells of the endothelial lineage, including ECFC-like cells. For example, Activin A, vascular endothelial growth factor (VEGF), basic fibroblast growth factor (FGF-2) and bone morphogenetic protein 4 (BMP-4) are included in a chemically defined differentiation medium to induce differentiation of pluripotent cells into cells of the endothelial lineage, including ECFC-like cells.

In one embodiment of the ECFC-like cell protocol provided herein, after 2 days (−D2) of culture in a basal culture medium (e.g., mTeSR1), differentiation of pluripotent cells was directed toward the endothelial lineage by contacting the cells for 24 hours with an endothelial differentiation medium comprising an effective amount of Activin A, BMP-4, VEGF and FGF-2. Following 24 hours of differentiation, Activin A was removed from the culture by replacing the endothelial differentiation medium with an endothelial differentiation medium comprising an effective amount of BMP-4, VEGF and FGF-2. By "effective amount", we mean an amount effective to promote differentiation of pluripotent cells into cells of the endothelial lineage, including ECFC-like cells. Further replacement of the endothelial differentiation medium comprising an effective amount of BMP-4, VEGF and FGF-2 may be done every 1-2 days.

Activin A is a member of the TGF-B superfamily that is known to activate cell differentiation via multiple pathways. Activin-A facilitates activation of mesodermal specification but is not critical for endothelial specification and subsequent endothelial amplification. In one embodiment, the endothelial differentiation medium comprises Activin A in a concentration of about 5-25 ng/mL. In one preferred embodiment, the endothelial differentiation medium comprises Activin A in a concentration of about 10 ng/mL.

Bone morphogenetic protein-4 (BMP-4) is a ventral mesoderm inducer that is expressed in adult human bone marrow (BM) and is involved in modulating proliferative and differentiative potential of hematopoietic progenitor cells (Bhardwaj et al., 2001; Bhatia et al., 1999; Chadwick 2003). Additionally, BMP-4 can modulate early hematopoietic cell development in human fetal, neonatal, and adult hematopoietic progenitor cells (Davidson and Zon, 2000; Huber et al., 1998; Marshall et al., 2000). In one embodiment, the endothelial differentiation medium comprises BMP-4 in a concentration of about 5-25 ng/mL. In one preferred embodiment, the endothelial differentiation medium comprises BMP-4 in a concentration of about 10 Ong/mL.

Vascular endothelial growth factor (VEGF) is a signaling protein involved in embryonic circulatory system formation and angiogenesis. In vitro, VEGF can stimulate endothelial cell mitogenesis and cell migration. In one embodiment, the endothelial differentiation medium comprises VEGF in a concentration of about 5-50 ng/mL. In one preferred embodiment, the endothelial differentiation medium comprises VEGF in a concentration of about 10 ng/mL. In one particularly preferred embodiment, the endothelial differentiation medium comprises $VEGF_{165}$ in a concentration of about 10 ng/mL.

Basic fibroblast growth factor, also referred to as bFGF or FGF-2, has been implicated in diverse biological processes, including limb and nervous system development, wound healing, and tumor growth. bFGF has been used to support feeder-independent growth of human embryonic stem cells. In one embodiment, the endothelial differentiation medium comprises FGF-2 in a concentration of about 5-25 ng/mL. In one preferred embodiment, the endothelial differentiation medium comprises FGF-2 in a concentration of about 10 ng/mL.

In contrast to previous protocols for generating ECs from hPSCs, the method disclosed herein does not require co-culture with supportive cells, such as, for example, OP9 stromal cells.

In contrast to previous protocols for generating ECs from hPSCs, the method disclosed herein does not require embryoid body (EB) formation.

In contrast to previous protocols for generating ECs from hPSCs, the method disclosed herein does not require exogenous TGF-β inhibition.

C. Isolating ECFC-Like Cells from the Differentiated Endothelial Cells

In one embodiment of the method disclosed herein, CD31+NRP-1+ cells are selected and isolated from the population of cells undergoing endothelial differentiation. Methods, for selecting cells having one or more specific molecular markers are known in the art. For example, cells may be selected based on expression of various transcripts by flow cytometry, including fluorescence-activated cell sorting, or magnetic-activated cell sorting.

In one embodiment, CD31+NRP-1+ cells are selected from a population of cells undergoing endothelial differentiation, as described herein, on day 10, 11 or 12 of differentiation. In one preferred embodiment, CD31+NRP-1+ cells are selected from the population of cells undergoing endothelial differentiation on day 12 of differentiation. The inventors have found that the day 12 population of cells undergoing endothelial differentiation contains a higher percentage of NRP-1+ cells relative to cell populations that are present on other days of differentiation.

In the Examples below, adherent ECs were harvested after day 12 of differentiation and made into a single cell suspension. Cells were counted and prepared for antibody staining with anti-human CD31, CD144 and NRP-1. $CD31^+$ CD144+NRP-1+ cells were sorted and selected using flow cytometry.

In one embodiment, the selected cells exhibit a cobblestone morphology, which is typical of ECs, including ECFCs.

In one embodiment, the selected cells have a capacity to form capillary-like networks on Matrigel™-coated dishes, which is typical of ECs, including ECFCs.

In one embodiment, the selected cells have a capacity for in vivo vessel formation in the absence of co-culture and/or co-implanted cells, which is typical of ECFCs.

In one embodiment, the selected cells exhibit clonal proliferation potential that is equal to or greater than CB-ECFCs and greater than ECs derived in vitro using known protocols.

In one embodiment, the selected cells exhibit high clonal proliferation potential. For example, in one embodiment, about 95% or more of isolated single ECFC-like cells proliferate and at least about 35-50% of the isolated single ECFC-like cells are HPP-ECFC-like cells that have a capacity to self-replenish, thereby giving rise to additional HPP-ECFC-like cells.

D. Expansion of Isolated ECFC-Like Cells.

In various embodiments, the isolated $CD31^+NRP-1^+$ ECFC-like cells are expanded under conditions suitable for endothelial growth. In one embodiment, culture conditions for endothelial cell growth that are known in the art may be used to expand the isolated $CD31^+NRP-1^+$ ECFC-like cells. In one embodiment, discussed further below, culture dishes are coated with type 1 collagen as a matrix attachment for the cells. Fibronectin, Matrigel or other cell matrices may also be used to facilitate attachment of cells to the culture dish. In one embodiment, discussed further below, Endothelial Growth Medium 2 (EGM2) plus VEGF, IGF1, EGF, and FGF2, vitamin C, hydrocortisone, and fetal calf serum may be used to expand the isolated $CD31^+NRP-1^+$ ECFC-like cells.

In the Examples below, CD31$^+$NRP-1$^+$ isolated ECFC-like cells were centrifuged and re-suspended in 1:1 endothelial growth medium and endothelial differentiation medium. To generate ECFC-like cells from the selected population of cells, about 2500 selected cells per well were seeded on collagen-coated 12-well plates. After 2 days, the culture medium was replaced with a 3:1 ratio of endothelial growth medium and endothelial differentiation medium. ECFC-like colonies appeared as tightly adherent cells and exhibited cobblestone morphology on day 7 of expansion.

In the Examples below, ECFC-like cell clusters were cloned to isolate substantially pure populations of HPP-ECFC-like cells. By "pure" or "substantially pure" we mean a population of cells that is at least about 75% (e.g., at least about 75%, 85%, 90%, 95%, 98%, 99% or more) pure, with respect to HPP-ECFC-like cells making up a total cell population. In other words, the term "substantially pure" refers to a population of ECFC-like cells, as provided herein, that contains fewer than about 25%, 20%, about 10%, or about 5% of non-ECFC-like cells when directing differentiation to obtain cells of the endothelial cell lineage. The term "substantially pure" also refers to a population of ECFC-like cells, as provided herein, that contains fewer than about 25% 20%, about 10%, or about 5% of non-ECFC-like cells in an isolated population prior to any enrichment, expansion step, or differentiation step. In some cases, a substantially pure isolated population of ECFC-like cells generated according to a method provided herein is at least about 95% (e.g., at least about 95%, 96%, 97%, 98%, 99%) pure with respect to cells of the endothelial cells making up a total cell population. Cloning techniques that are known in the art can be used in methods disclosed herein.

In the Examples below, confluent ECFC-like cells were passaged by plating 10,000 cells per cm$^2$ as a seeding density and maintaining ECFC-like cells in complete endothelial growth media (collagen coated plates and cEGM-2 media) with media change every other day. Cell passaging techniques that are known in the art can be used in methods disclosed herein.

In one embodiment, the ECFC-like cells generated using the method provided herein can be expanded in a composition comprising endothelium growth medium and passaged up to 18 times, while maintaining a stable ECFC-like cell phenotype. By "stable ECFC-like cell phenotype", we mean cells exhibiting cobblestone morphology, expressing the cell surface antigens CD31 and CD144, and having a capacity to form blood vessels in vivo in the absence of co-culture and/or co-implanted cells. In a preferred embodiment, ECFC-like cells having a stable phenotype also express CD144 and KDR but do not express α-SMA (alpha-smooth muscle actin).

III. Isolated Populations of ECFC-Like Cells

In one embodiment, an isolated population of human NRP-1$^+$/CD31$^+$ ECFC-like cells is provided. In one embodiment, the purified human cell population of NRP-1$^+$/CD31$^+$ ECFC-like cells provided is generated using the in vitro method for generating ECFC-like cells from hPSCs disclosed herein.

In the Examples below, the method disclosed herein is used to generate a purified human cell population of NRP-1$^+$ and CD31$^+$ ECFC-like cells. The isolated ECFC-like cells of the population exhibit cobblestone morphology and have a capacity for blood vessel formation in vivo without co-culture and/or co-implanted cells. In one embodiment, the ECFC-like cells of the population are further characterized by one or more of CD144+, KDR+ and α-SMA-.

In one embodiment, at least some of the ECFC-like cells in the population have a high proliferation potential that is greater than or equal to the proliferation potential of CB-ECFCs and greater than the proliferation potential of ECs generated in vitro using other known protocols. In one preferred embodiment, the ECFC-like cell population comprises HPP-ECFCs having a proliferative potential to generate at least 1 trillion ECFC-like cells from a single starting pluripotent cell.

In one preferred embodiment, the isolated ECFC-like cell population is substantially pure.

In one preferred embodiment, the isolated ECFC-like cell population provided herein contains at least about 35-50% ECFC-like cells having the following characteristics:
A. characteristic ECFC-like molecular phenotype;
B. capacity to form capillary-like networks in vitro on Matrigel™;
C. high proliferation potential;
D. self-replenishing potential;
E. capacity for blood vessel formation in vivo without co-culture cells; and
F. increased cell viability and/or decreased senescence.

Each of the aforementioned ECFC-like characteristics is discussed further herein below.

A. ECFC-Like Cell Molecular Phenotype

Cells of the endothelial lineage have characteristic molecular markers including, for example, CD31, CD144, KDR and NRP-1. Cord blood ECs are known to express various endothelial markers, including CD31, CD144, KDR and NRP-1. At present, the inventors are not aware of a specific marker that distinguishes CB-ECFCs from any other ECs derived from blood vessels. Methods of measuring molecular expression patterns in ECs, including ECFCs, are known. For example, various known immunocytochemistry techniques for assessing expression of various markers in cells generated using the method of the present disclosure.

In the Examples herein, ECFC-like cells are CD31$^+$NRP-1$^+$. In one preferred embodiment, ECFC-like cells derived using the method provided herein also express CD144 and KDR and do not express α-SMA. In contrast, ECs produced in vitro from hPSCs using protocols that require co-culture with OP9 cells or EB development often express α-SMA.

B. Capacity to Form Capillary-Like Networks In Vitro on Matrigel™

Like various other ECs, ECFCs derived from cord blood can form capillary-like networks when cultured in vitro on Matrigel™

In one embodiment, the ECFC-like cells and populations generated from hPSCs in vitro using the method provided herein have the capacity to form capillary-like networks when cultured in vitro on Matrigel™.

C. High Proliferation Potential

Endothelial cells (ECs) derived from hPSCs in vitro using various different protocols have different proliferation potentials relative to CB-ECFCs. For example, as shown in the Examples herein, approximately 45% of single cell CB-ECFCs have low proliferative potential (LPP) and approximately 37% of single cell CB-ECFCs have high proliferative potential (HPP). As shown in the Examples herein, at least about 35% of ECFC-like cells in the isolated ECFC-like cell populations provided herein are HPP-ECFC-like cells. In a preferred embodiment, at least about 50% of ECFC-like cells in the isolated ECFC-like cell populations provided herein are HPP-ECFC-like cells.

In contrast, ECs produced in vitro using a protocol comprising co-culture of cells with OP9 cells (e.g., Choi et al; Stem Cells 2009) exhibit a clonal proliferation potential wherein fewer than 3% of cells give rise to HPP-ECs. Endothelial cells produced using an in vitro protocol comprising EB formation (e.g., Cimato et al. Circulation 2009), exhibit a clonal proliferation potential, wherein fewer than 3% of cells give rise to HPP-ECs. Endothelial cells produced using an in vitro protocol, which comprises exogenous TGF-β inhibition (e.g., James et. al. 2010), exhibit a clonal proliferation potential, wherein about 30% of cells give rise to HPP-ECs, but only in the continued presence of TGF-β inhibition (i.e., if exogenous TGF-β inhibition is removed from this protocol the ECs lose all their HPP activity).

Various techniques for measuring proliferative potential of cells are known in the art and can be used with the method provided herein to confirm the proliferative potential of the ECFC-like cells. In the Examples herein, single cell assays were used to evaluate clonogenic proliferative potential of CB-ECFCs, iPS derived-ECFC-like cells, EB-derived ECs and peripheral artery disease (PAD)-derived ECs. Briefly, CB-ECFCs, ECFC-like cells and ECs were treated to obtain a single cell suspension. Suspended cells were counted, diluted and single cells were cultured in each well of 96-well plates. After several days of culture, each well was examined to quantitate the number of cells. Those wells containing two or more cells were identified as positive for proliferation. Wells with EC counts of 1 were categorized as non-diving, wells with EC counts of 2-50 were categorized as endothelial cell clusters (ECCs), wells with EC counts of 51-500 or 501-2000 were categorized as low proliferative potential (LPP) cells and wells with EC counts of ≥2001 were categorized as high proliferative potential (HPP) cells.

D. Self-Replenishing Potential

Endothelial cells derived using various different protocols have different capacities for self-replenishment. By self-replenish, we mean the ability to divide into like cells. For example, the HPP-ECFC-like cells provided herein have a capacity to give rise to one or more HPP-ECFC-like cells within a secondary HPP-ECFC-like colony when replated in vitro. In one embodiment, the self-replenishing HPP-ECFC-like cells are suitable for use in cell therapy, at least because a therapeutically sufficient number of HPP-ECFC-like cells may be generated in vitro using the methods provided herein.

E. Capacity for Blood Vessel Formation In Vivo without Co-Culture Cells.

Endothelial colony forming cells derived using various different protocols have different capacities for blood vessel formation in vivo. For example, CB-ECFCs can form blood vessels when implanted in vivo in a mammal, such as, for example, a mouse.

In contrast, ECs produced using the protocol of Choi et al (2009), which comprises co-culture of cells with OP9 cells for generation of ECs, do not form host murine red blood cell (RBC) filled functional human blood vessels when implanted in vivo in a mammal. ECs produced using the protocol of Cimato et al. (2009), which comprises EB formation for generation of ECs, do not form host RBC filled functional human blood vessels when implanted in vivo in a mammal. ECs produced using the protocol of James et. al. (2010), which comprises TGF-β inhibition for generation of ECs, form significantly fewer functional human blood vessels when implanted in vivo in a mammal (i.e., 15 times fewer than cells from the presently disclosed protocol). Further the cells of James et al. can only form functional human blood vessels when implanted in vivo in a mammal if the culture continues to contain TGF-beta; if TGF-beta is removed the cells completely lose the ability to make RBC-filled human blood vessels. ECs produced using the protocol of (Samuel et al PNAS 2013), which lacks the step of selecting day 12 CD31$^+$NRP1$^+$, can only form blood vessels when implanted in vivo in a mammal if the ECs are implanted with supportive cells (i.e., mesenchymal precursor cells).

In contrast to the above prior art methods, in the Examples herein, cells in the ECFC-like cell populations can form blood vessels when implanted in vivo in a mammal, even in the absence of supportive cells.

Various techniques for measuring in vivo vessel formation are known and can be used. In the Examples herein, in vivo vessel formation was assessed by adding to three-dimensional (3D) cellularized collagen matrices ECFC-like cells generated using the methods of the present disclosure. The collagen mixture containing the ECFC-like cell suspension allowed to polymerize in tissue culture dishes to form gels. Cellularized gels were then implanted into the flanks of 6- to 12-week-old NOD/SCID mice. Two weeks after implantation, gels were recovered and examined for human endothelial-lined vessels perfused with mouse red blood cells.

The capacity to form blood vessels in vivo in the absence of exogenous supportive cells is one indicator that the cells produced using the methods disclosed herein are ECFCs.

F. Increased Cell Viability and/or Decreased Senescence

Endothelial cells derived using various different protocols have different levels of cell viability and/or levels of senescence relative to CB-ECFCs. For example, in the Examples herein, viable CB-ECFCs can be passaged up to 18 times.

In contrast, EC cells produced using the protocol of Choi et al (2009), which comprises co-culture of cells with OP9 cells for generation of ECs, have a viability of 6 passages. ECs produced using the protocol of Cimato et al. (2009), which comprises EB formation for generation of ECs, have a viability of 7 passages. ECs produced using the protocol of James et. al. (2010), which comprises exogenous TGF-β inhibition for generation of endothelial cells, have a viability of 9 passages and tin the absence of TGF-β inhibition, the EC of James et al. transition to a mesenchymal cell type, thereby losing their endothelial characteristics. ECs produced using the protocol of Samuel et al., which lacks the step of selecting day 12 CD31$^+$NRP-1$^+$ cells, could be expanded for up to 15 passages.

In contrast to the above methods for generating ECs in vitro, in the Examples herein, viable cells in the ECFC-like cell populations could be expanded for up to 18 passages. CB-ECFCs may be passaged between 15-18 times.

Various techniques for measuring cell viability and senescence are known in the art and useful in the present disclosure. In the Examples herein, cell viability was assessed by trypan blue exclusion and cell senescence was assessed using a senescence assay kit (Biovision). Other methods of assessing cell viability and/or senescence are known in the art and can be used.

IV. Use of ECFC-Like Cells Disclosed Herein

In contrast to ECFCs, which are primary cells, the ECFC-like cells generated using the method disclosed herein can be generated in vitro in a volume that can be useful for various clinical applications, as described below.

A. Therapy

In one aspect, methods, cells and compositions suitable for cell transplantation, cell replenishment, and/or cell or tissue replacement are provided herein. The method can comprise providing to a subject in need thereof a therapeutically effective amount of ECFC-like cells derived according to a method provided herein, whereby providing ECFC-like cells treats the subject. By "therapeutically effective amount", we mean an amount effective to treat a subject who is in need of epithelial repair. The cells and/or compositions provided herein may be administered to a subject in a manner that permits the ECFC-like cells to graft or migrate to an intended tissue site and reconstitute or regenerate the functionally deficient area.

Subjects suitable for receiving therapy using the ECFC-like cells provided herein include those having endothelial dysfunction and/or damage of various kinds. For example, subjects having cardiovascular disease, myocardial infarction, cardiac stroke, or peripheral artery disease (PAD) can be suitable subjects for receiving therapy using the ECFC-like cells of the present disclosure. Subjects having lung or kidney disease or damage can be suitable subjects for receiving therapy using the ECFC-like cells of the present disclosure. In preferred embodiments, PAD patients developing critical limb ischemia (CLI) can be suitable subjects for receiving therapy using the ECFC-like cells of the present disclosure.

In one embodiment, the ECFC-like cells can be provided to a subject in the form of a pharmaceutical composition suitable for human administration. For example, the composition may comprise one or more pharmaceutically acceptable carriers, buffers, or excipients. The composition may further comprise, or be provided to the subject with, one or more ingredients that facilitate the engraftment ECFC-like cells. For example, the pharmaceutical composition may also comprise, or be provided to a subject with, one or more growth factors or cytokines (e.g., angiogenic cytokines) that promote survival and/or engraftment of transplanted cells, promote angiogenesis, modulate the composition of extracellular or interstitial matrix, and/or recruit other cell types to the site of transplantation.

In one embodiment, the pharmaceutical composition may be formulated, produced, and stored according to standard methods that provide proper sterility and stability.

For example, in one embodiment, the ECFC-like cells provided herein may be directly injected into a tissue that is lacking in adequate blood flow (as determined by a physician). In one embodiment, the ECFC-like cells provided herein may be suspended in a matrix comprised of collagen, fibronectin, or a synthetic material and this gelatinous suspension of the ECFC-like cells may be directly injected into a tissue that is lacking in adequate blood flow. The concentration of ECFC-like cells injected into the tissue may vary, for example, from about 10,000 to about 100,000 cells/microliter of delivery vehicle or matrix material. In some tissues, the cells may be delivered on a single occasion with recovery of adequate blood flow whereas other tissues may require multiple injections and sequential injections over time to rescue adequate blood flow.

After administering the ECFC-like cells into the subject, the effect of the treatment method may be evaluated, if desired and the treatment may be repeated as needed or required. Therapy efficacy can be monitored by clinically accepted criteria known in the art, such as, for example, reduction in area occupied by scar tissue, revascularization of scar tissue, frequency and severity of angina; an improvement in developed pressure, systolic pressure, end diastolic pressure, subject mobility and/or quality of life.

ECFC cells can rescue an eye from hypoxia and neovascularization. Therefore, it is contemplated herein that the ECFC-like cells provided herein be used to treat various eye diseases in which hypoxia and neovascularization occurs, such as, for example, retinopathy of prematurity, diabetic retinopathy, central vein occlusion, or macular degeneration.

It is also contemplated that the ECFC-like cells provided herein may be used to coat at least a portion of the inside of a vascular stent and optionally any area of a vessel that became denuded of endothelial cells during the stent placement. In this case, the intravenously injected ECFC-like cells would bind to areas of injury and re-endothelialize the vessels to prevent blood clot formation and/or restenosis of the vessel area in which the stent has been placed.

It is known that placement of human veins (saphenous or umbilical) as grafts into arteries of patients that have areas of stenosis and blockade of blood flow, have a high incidence of subsequent stenosis and blocked blood flow. This is associated with loss of the blood vessel endothelial cells early in the process of vessel remodeling in vivo. It is contemplated herein that the ECFC-like cells provided herein can be intravenously injected into the vasculature of such a patient in order to re-endothelialize the implanted graft and to preserve the function of the vessel in the patient.

B. Test Agent Screening

The ECFC-like cells disclosed herein can be used to screen for factors (such as solvents, small molecule drugs, peptides, oligonucleotides) or environmental conditions (such as culture conditions or manipulation) that affect the characteristics of ECFC-like cells and any tissues developed therefrom. In one embodiment, test agents, such as, for example, pharmaceutical compounds, can be screened using the ECFC-like cells of the present disclosure to determine their effect on endothelial health and/or repair. For example, screening may be done either because the compound is designed to have a pharmacological effect on the endothelial cells, or because a compound designed to have effects elsewhere may have unintended side effects on endothelial cells. In various embodiments, the ECFC-like cells herein are particularly useful for test agent screening, at least because they are differentiated in vitro from cultured pluripotent cells. In contrast, CB-ECFCs are primary cells obtained from patient blood. Various methods of screening test agent compounds are known in the art and can be used with the ECFC-like cells disclosed herein.

For example, screening the activity of test agents may comprise: i) combining the ECFC-like cells disclosed herein with a test agent, either alone or in combination with other agents; ii) determining changes in the morphology, molecular phenotype, and/or functional activity of the ECFC-like cells that can be attributed to the test agent, relative to untreated cells or cells treated with a control agent; and iii) correlating the effect of the test agent with the observed change.

In one embodiment, cytotoxicity of a test agent on the ECFC-like cells provided herein can be determined by the effect the agent has on one or more of ECFC-like cell viability, survival, morphology, and molecular phenotype and/or receptors.

In one embodiment, ECFC-like cell function can be assessed using a standard assay to observe phenotype or activity of the ECFC-like cells. For example, one or more of molecular expression, receptor binding, either in cell culture or in vivo, may be assessed using the ECFC-like cells disclosed herein.

C. Kits

In one embodiment, kits for use with methods and cells disclosed herein are contemplated. In one embodiment, a kit can comprise a differentiation and/or growth medium, as described herein, in one or more sealed vials. In one embodiment, the kit can include one or more cells, such as pluripotent cells and/or ECFC-like cells, as disclosed herein. In one embodiment, the kit can include instructions for generating ECFC-like cells from pluripotent cells. In one embodiment, kits can include various reagents for use with the present disclosure in suitable containers and packaging materials.

The disclosure will be more fully understood upon consideration of the following non-limiting Examples.

EXAMPLES

Example 1: Materials and Methods

Culturing of hES and hiPS Cells:

Human Embryonic stem cell (hESC) line H9[47] and fibroblast-derived human iPS cell line (DF19-9-11T)[48] were purchased from WiCell Research institute (Madison, Wis.). Several other hiPS cell lines (FCB-iPS-1 and FCB-iPS-2) derived in the Broxmeyer and Yoder laboratories were also used to generate ECFCs[20, 21] (Table 1). Both hESC and hiPSCs were maintained in mTeSR1 complete media (Stem Cell Technologies) on Matrigel™ in 10 cm² tissue culture dishes at 37° C. and 5% $CO_2$. After the plating of cells, media was changed on days 2, 3, and 4. Cells were passaged on Day 5. Media was aspirated and 4-5 mL of dispase (2 mg/mL, Gibco) containing media was added to each plate, which was then incubated at 37° C. for 3-5 minutes or until the edges of colonies had lifted from the plate. Dispase-containing media was aspirated from the plate and cells were gently washed with DMEM-F12 (Gibco) 3 times to remove any residual enzyme. Fresh media was then used to collect colonies from the plate using a forceful wash and scraping with a 5 mL disposable pipette, taking care to avoid bubbles. Collected colonies were centrifuged at 300×g for 5 minutes. The supernatant was aspirated and the pellet was resuspended in mTeSR1 complete media. Prior to passaging, 10 cm² tissue culture dishes were coated with Matrigel™ for 30 minutes. Unattached Matrigel™ was removed from the tissue culture dishes and 7 mL of mTeSR1 complete medium was added to dishes. Colonies evenly distributed in mTeSR1 media were added to each plate. Cells were then spread out within the dish using multiple side-to-side shaking motions while avoiding swirling. Cultures were checked for growth quality and morphology on day 2. Teratoma formation assays were performed, as previously described[20].

TABLE 1 hES and hiPS cell lines used in the Examples herein.

| Cell line | Description |
|---|---|
| DF19-9-11T | Induced pluripotent stem cells reprogrammed from human foreskin fibroblasts using nonintegrating episomal vectors[48] |
| FCB-iPS-1 | Induced pluripotent stem cells reprogrammed from frozen human cord blood derived CD34+ cells using lentiviral vectors[20] |
| FCB-iPS-2 | Induced pluripotent stem cells reprogrammed from frozen human cord blood derived CD34+ cells using lentiviral vectors[20] |
| H9 | Human embryonic stem cell line derived from the inner cell mass of a blastocyst-stage embryo[47] |

Directed Differentiation of hESC and hiPSCs into the EC Lineage, Including ECFC-Like Cells:

After 2 days (−D2) of culture in mTeSR1 media, cultures were directed toward the mesodermal lineage with addition of activin A (10 ng/mL) in the presence of FGF-2, $VEGF_{165}$, and BMP4 (10 ng/mL) for 24 hrs. The following day, activin-A containing media was removed and replaced with 8 mL of Stemline II complete media (Sigma) containing FGF-2 (Stemgent), $VEGF_{165}$ (R&D) and BMP4 (R&D). Media was replaced with 8 ml of fresh Stemline II differentiation media on days 3, 5, 7, and 8. On day 9 and thereafter media was changed with 10 mL of Stemline II differentiation media.

Flow Cytometry:

On day 12 after differentiation, adherent cells were harvested using TrypleE and made into a single cell suspension in EGM-2 medium. Cells were counted and aliquots of the cell suspension were prepared for antibody staining. FcR blocking reagent (Miltyni Biotech cat #120-000-442) was added to prevent the non-specific binding of antibodies. Anti-human CD31 (CD31-FITC, clone WM59 from BD Pharmingen, Cat #555445), CD144 (CD144-PE, clone 16B1 from ebioscience, Cat #12-1449-82) and NRP-1 (NRP-1-APC, clone AD5-176 from Miltenyi Biotech, Cat #130-090-900) antibodies were used at concentrations that were titrated prior to use. Propidium Iodide (PI, Sigma) was added to the cell suspension for dead cell staining. Flow cytometric detection of the cell surface antigens and cells sorting were performed on an LSR II and FACS Aria (Becton Dickinson), respectively. Compensation was set by single positive controls using cord blood derived ECFCs. A gating of targeted cell population was determined based on fluorescent minus one (FMO) controls for each fluorescent color.

Cell Culture of Sorted Cells:

$CD31^+$, $CD144^+$ or $KDR^+$ and $NRP-1^+$ sorted cells were centrifuged at 300×g for 5 minutes then resuspended in 50% EGM-2 and 50% complete Stemline II differentiation media. To generate ECFCs from the sorted population, 2500 cells per well were seeded on rat tail type I collagen-coated 12 well plates. After 2 days, the media was aspirated and three parts of EGM-2 and one part of differentiation media were added to the cultures. ECFC-like cell colonies appeared as tightly adherent cells and exhibited cobblestone morphology on day 7. On occasion, cloning cylinders were used to isolate ECFC-like cell colonies from heterogeneous cell populations. Cloning of endothelial cell clusters was performed to isolate pure populations of highly proliferative endothelial cells as described previously[1, 2, 49]. Confluent ECFC-like cells were passage by plating 10,000 cells per cm² as a seeding density and ECFC-like cells were maintained in complete endothelial growth media (collagen coated plates and cEGM-2 media) with media changes every other day, as described previously[1, 2, 49].

In Vitro Capillary-Like Network Formation Assay on Matrigel™:

Endothelial cells derived from various different protocols were trypsinized and resuspended in EGM-2 media. Cells were plated at a density of 1.0×10⁴ cells per well in triplicate in 96-well plates coated with 50 μL of growth factor-reduced Matrigel™ (BD Biosciences). Plates were incubated overnight at 37° C. After 8-16 hours of incubation, photomicrographs were taken of each well at ×10 magnification using a Zeiss Axiovert 25 CFL inverted microscope with a 10× CP-ACHROMAT/0.12 NA objective. Images were acquired using a SPOT RT color camera (Diagnostic Instruments) with the manufacturer's software. Phase contrast images were taken with air objectives.

Immunochemistry:

ECFC-like cells were fixed with 4% (w/v) paraformaldehyde for 30 minutes and permeabilized with 0.1% (v/v) TritonX-100 in PBS for 5 minutes. After blocking with 10%

(v/v) goat serum for 30 min, cells were incubated overnight at 4° C. with the following primary antibodies: anti-CD31 (Santa Cruz), anti-CD144 (ebioscience), anti-NRP-1 (Santa Cruz) and anti-α-SMA, (Chemicon). Cells were washed with PBS, then incubated with secondary antibodies conjugated with Alexa-488 or Alexa-565 (Molecular Probe) and visualized by confocal microscopy after counterstaining with 2 g/ml DAPI (Sigma-Aldrich). The confocal images were obtained with an Olympus FV1000 mpE confocal microscope using as an Olympus uplanSApo 60×W/1.2NA/ eus objective. All images were taken as Z-stacks with individual 10μ thick sections at room temperature and images were analyzed using FV10-ASW 3.0 Viewer.

Single Cell Assay:

CB-ECFCs or iPS derived-ECFC-like cells or EB-derived ECs and PAD-derived ECs were subjected to a single cell assay to evaluate clonogenic proliferative potential. Briefly, ECs were treated with trypLE Express (Invitrogen) to obtain a single cell suspension. Cell counts and serial dilutions were performed to obtain a concentration of 0.68 cells per well in individual wells of 96-well culture plates. Wells were examined the day after plating to ensure the presence of a single cell per well. Culture media was changed on days 4, 8, and 12. On day 14 of culture, cells were stained with Sytox reagent (Invitrogen), and each well was examined by fluorescent microscopy to quantitate the number of cells (10× magnification; Zeiss Axiovert 25 CFL inverted microscope with a 10× CP-ACHROMAT/0.12 NA objective). Wells containing two or more cells were identified as positive for proliferation (10× magnification; Zeiss Axiovert 25 CFL inverted microscope with a 10× CP-ACHROMAT/ 0.12 NA objective). Wells with EC counts of 1 were categorized as non-diving, wells with EC counts of 2-50 were categorized as endothelial cell clusters (ECCs), wells with EC counts of 51-500 or 501-2000 were categorized as low proliferative potential (LPP) cells and wells with EC counts of ≥2001 were categorized as high proliferative potential (HPP) cells, as previously described[1, 2, 49].

Cell Viability, Senescence and Cell Proliferation Assay:

Endothelial cells were plated at a density of $5 \times 10^4$ per well or $1 \times 10^5$ per well on type I collagen-coated 12-well and 6 well plates respectively. After 24 h, growth media was replaced with Fc-control, Fc-NRP-1 dimer (R&D Systems) or NRP-1 blocking antibodies containing EGM-2 medium for 7 days and media was replaced on every alternative day. NRP-1A and NRP-1B antibodies were generously provided by Genentech[42]. Cell viability and proliferation was assessed by trypan blue exclusion, and the numbers of dye-free cells were counted under a phase microscope in triplicate per condition.

A senescence assay kit was purchased from Biovision (cat # K320-250) and the assay performed according to the manufacturer's instructions. Briefly, endothelial cells were seeded onto 12 well plates for overnight culture to form a monolayer. The following day, cells were fixed in 0.5 ml of the commercial fixative solution for 10-15 min at room temperature. Cells were washed twice with 1 ml of 1×PBS and stained with 0.5 ml of the commercial staining solution overnight at 37° C. Cells were observed under a microscope for development of a blue color. Photomicrographs were taken from each well at 10× magnification using a Zeiss Axiovert 25 CFL inverted microscope with a 10×CP-ACHROMAT/0.12 NA objective. Images were acquired using a SPOT RT color camera (Diagnostic Instruments) with the manufacturer's software. Phase contrast images were taken with air objectives.

Mice:

All animal procedures were carried in accordance with the Guidelines for the Care and Use of Laboratory Animals and were approved by the Institutional Animal Care and Use Committees (IACUCs) at Indiana University School of Medicine (Indianapolis, Ind.). Both male and female 6-12 week old NOD/SCID mice (T- and B-cell deficient, impaired complement) were used for all animal studies. NOD-SCID mice were maintained under specific-pathogen-free conditions at the Indiana University Laboratory Animal Resource Center (LARC). Previous work with this animal model was used to determine the minimum number of animals needed to obtain statistically significant results[1, 50]. Previous studies have shown that 8 out of 10 matrices (one animal received two matrices) implanted inosculate with the host vasculature and that 8 matrices (4 animals) with functional vessels are needed for each group for statistical significance[1, 50]. Method of randomization was not used while allocating samples and animals to each experimental group. Also, investigator was not blinded to the group allocation both during the experiment and when accessing the outcomes.

In Vivo Vessel Formation Assay:

Pig skin type I collagen was used to generate three-dimensional (3D) cellularized collagen matrices, as previously described[4, 50]. Briefly, type 1 collagen gel mixture was prepared by mixing together ice-cold porcine skin collagen solution in 0.01N HCL, and neutralized with phosphate buffered saline and 0.1N NaOH to achieve neutral pH (7.4). Neutralized gel mixtures (~1.5 mg/mL) were kept on ice before induction of polymerization by warming at 37° C., in 5% $CO_2$. Cultured CB-ECFCs or ECFC-like cells or ECs were added to the collagen mixture to a final concentration of two million cells/ml collagen. The collagen mixture (250 μL) containing the cell suspension was added to 48-well tissue culture dishes and was allowed to polymerize to form gels by incubation in $CO_2$ at 37° C. for 30 minutes. The gels were then overlaid with 500 μl of culture medium for overnight at 37° C., in 5% $CO_2$.

After 18 hours of ex vivo culture, cellularized gels were implanted into the flanks (a bluntly dissected subcutaneous pouch of anterior abdominal wall with close proximity of host vasculature) of 6- to 12-week-old NOD/SCID mice, as previously described[1, 49]. Surgical procedures to implant collagen gels were conducted under anesthesia and constant supply of oxygen. Incisions were sutured and mice were monitored for recovery. Two weeks after implantation, gels were recovered by excising engrafts in animals that had been humanely sacrificed per approved IACUC protocol. Immunohistochemistry was performed as described previously using H&E and anti-human CD31 staining to examine the gels for human endothelial-lined vessels perfused with mouse red blood cells. hCD31$^+$ blood vessels were imaged from each explant using a Leica DM 4000B microscope (Leica Microsystems, Bannockburn, Ill.) with attached Spot-KE digital camera (Diagnostic Instruments, Sterling Heights, Mich.). Functional vessels were counted only if they contained at least 1 mouse erythrocyte.

Oxygen-Induced Retinopathy Model:

All experiments were performed in conformity to the ARVO Statement for the Use of Animals in Ophthalmic and Vision Research and the UK Home Office Regulations. Oxygen-induced retinopathy was induced in C57/BL6 wild-type mice, as previously described2. Briefly, postnatal day (P) 7 newborn mice and their nursing dams were exposed to 75% oxygen (Pro-Ox 110 Chamber Controller; Biospherix, Redfield, N.Y.) for 5 d. At P12 they were transferred back to room air. At P13, mice received a 1 μl intravitreal injection containing $1 \times 10^5$ hiPSC-ECFC-like cells, hiPSC-EBT- CD144+ ECs or CB-ECFCs that had previously been labeled (Qtracker 655; Invitrogen). Phenol red-free DMEM without growth factors and serum was used as vehicle and injected in the left eye of each pup as a control. All pups were euthanized 72 h later with sodium pentobarbital and eyes fixed in 4% paraformaldehyde. Retinal flat mounts were stained with isolectin B4 (Sigma) and streptavidin-AlexaFlour488 (Invitrogen), and stained retinas were visualized and imaged using a confocal microscope. Area quantification was performed using ImageJ software by three independent, blinded investigators as described[2].

Mouse Hind Limb Ischemia Model:

Hind limb ischemia experiments were performed as we previously described[24]. Briefly, 6-week-old male athymic nude mice (body weight 25-30 g; Orient bioAnimal Inc., Seoul, Korea) were anesthetized with rompun (20 mg/kg) and ketamine (100 mg/kg). The femoral artery and its branches were ligated through a skin incision with 6-0 silk (Ethicon). The external iliac artery and all of the arteries above it were then ligated. The femoral artery was excised from its proximal origin as a branch of the external iliac artery to the distal point where it bifurcates into the saphenous and popliteal arteries. Immediately after arterial dissection, athymic mice were randomly assigned to 1 of 4 experimental groups. After the ischemic surgery, the hiPSC-ECFC-like cells or CB-ECFCs or hiPS-EBT-CD144+ ECs ($1.0 \times 10^6$ cells per mouse) were suspended in 200 µl of EGM-2 and these cells or vehicle control were injected intramuscularly into six sites of the gracilis muscle in the medial thigh with 29-gauge tuberculin syringes. A Laser Doppler perfusion imager (Moor Instruments) was used to measure the blood flow in the hind limbs on days 0 and 28 post-treatment as previously described[24]. Digital color-coded images were analyzed to quantify the blood flow in the region from the knee joint to the toe, and the mean perfusion values were calculated. All animal care and experimental procedures for hind limb ischemia experiments were performed under the approval of the animal care committees of CHA University (IACUC No. 130024).

Isolation of Arterial ECs from Patients with Peripheral Vascular Disease (PAD):

Disease artery (DA) ECs were obtained from patients with peripheral vascular disease who underwent lower extremity amputations following informed consent and use of a protocol that was approved by the Indiana University human IRB panel. Patients with active cellulitis, purulent drainage or wet gangrene were not used in this study, due to the high risk of yeast contamination. Likewise, patients with hepatitis B or C, and patients with HIV were excluded from this study. Following transection, amputated legs were immediately explored in the operating room for suitable specimens of arteries on a sterile table separate from the operative field. Samples deemed suitable were placed into a container filled with Hank's balanced salt solution (HBSS; Invitrogen) and taken to the lab for processing. Under sterile conditions, the vessels were opened length wise in a tissue culture dish and immersed in EGM-2 culture media (Lonza). The intima of each vessel was scraped with a cell scraper (TPP, Zurich, Switzerland) and washed with DMEM. The cell fraction left from the washings was centrifuged at 1620 rpm for 10 minutes, after which it was plated onto rat-tail type I collagen-coated six-well plates. After several days, growing endothelial colonies could be seen via light microscopy, and these colonies were isolated with cloning cylinders, trypsinized and replated onto new six-well plates to prevent mesenchymal cell contamination. The purified ECs were passage 1-2 times more, and then expanded in T-75 tissue culture flasks (TPP) prior to cryopreservation.

Culture of Endothelial Cells from Peripheral Blood of PAD Patient:

Mononuclear cells isolated from each patient's peripheral blood or cord blood were seeded on 6-well tissue culture plate pre-coated with type I rat tail collagen and were cultured in complete endothelial growth medium (EGM-2) supplemented with 10% FBS, 2% penicillin-streptomycin. Cells were maintained in a 37° C., 5% $CO_2$ humidified incubator, and medium was changed every other day for 2-3 weeks or until cobblestone-appearing endothelial colonies appeared. After initial appearance of colonies, cells were transferred to a new well of a 6-well plate and further passaged in 25-$cm^2$ flasks and at passages at 85-95% confluence. PAD cells at passages 3-7 at approximately 70% confluence were used in all studies.

Western Blot Analysis:

Cell lysates were prepared by resuspending cells in lysis buffer (20 mM Tris-HCl pH 7.5, 150 mM NaCl, 10% glycerol, 1% Triton X-100, 2 mM EDTA, 1 mM $Na_3VO_4$, 1 ug/ml each of aprotinin and leupeptin) followed by incubation on ice for 20 min. Insoluble components were removed by centrifugation at 12,000×g for 15 min. Protein concentrations were determined with a protein assay kit (Bio-rad). Proteins were separated by electrophoresis on 4-20% Tris-glycine minigels and then transferred onto immobilon-FL PVDF membrane (Millipore). Nonspecific binding was blocked with blocking buffer for 1 hr at room temperature and incubated overnight at 4° C. with primary antibodies against phospho-PYK2 (1:1,000; Cell Signaling) and phospho-p130$^{Cas}$ (1:1,000; Cell Signaling) in Odyssey blocking buffer. Blots were washed with PBS containing 0.1% Tween20, followed by incubation for 1 hour at room temperature with anti-rabbit antibody (1:10,000; LI-COR). Immunoreactive bands were detected using the Odyssey Infrared Imager (LI-COR).

RNA Sequence Library Construction, Sequencing and Analysis:

Total RNA was isolated from the samples using Trizol reagent (Invitrogen) and the RNA quality was examined as previously described[32]. An RNA sequence library was generated using 1 µg of high quality total RNA and sequencing was performed using Illumina HiSeq2000 sequencer as previously described[32]. RNA-sequence analysis was performed on total RNA isolated from hiPSCs-day 0 differentiation, hiPSC-derived cells-day 3 differentiation, hiPS-derived ECFC-like cells day 12 differentiation, hES-derived ECFC-like cells and CB-ECFCs. The resulting sequence reads were mapped to the human genome (hg18) using TopHat with default parameters, and the RefSeq (June 2010) transcript levels (FPKMs) were quantified using CuffLinks. Heatmaps of select transcripts belonging to individual germ layer and lineages were then analyzed by plotting using red-to-green scale using R statistical software package of heatmap.2 from RNA-seq data.

Further analysis of transcript expression to detect genes that were differentially expressed in hiPS-ECFC-like cells relative to CB-ECFCs involved (1) read mappings using STAR (Dobin et al. (2012) Bioinformatics, doi:10.1093/bioinformatics/bts635) (2) expression estimation using HTseq (Anders et al. (2014) Bioinformatics, doi: 10.1093/bioinformatics/btu638), and (3) differential analysis using DESeq (Anders and Huber (2010) Genome Biology 11:R106). First the RNA-Seq reads were mapped to reference genomes based on a specific gene model, i.e., the location of exons and junction sites on the genomes. STAR uses the reference genomes, GTF files, and RNA-Seq reads as its input, and uses uncompressed suffix arrays for storing sequences to detect known junctions (junctions in known isoforms), de novo detection of canonical junctions (junctions between known exons), non-canonical splices and chimeric transcripts such as fusions. Specifically, STAR 2.4.0 was run along with Human Genome GRCH37 using Ensembl version 70 gene models. Based on the mapping results, HTseq 0.6.1 was used to count the number of mappings that overlapped each gene as the expression values in group 2 (hiPSC-derived cells D3 differentiation), 3 (hiPSC-derived ECFC-like cells), and 4 (CB-ECFCs). Once the read counts were obtained, the genes which were not expressed in group 2 but were at least expressed in either group 3 or 4 were considered. Then DESeq was used to detect differential expressed genes from these candidates. In the DESeq model the data in the sample were counted via negative binomial (NB) distributions to resolve an overdispersion problem in traditional Poisson models (i.e. variations might be underestimated.) DESeq also includes several models from other groups to improve data fitting so even the number of replicates is not high (three replicates in this case), the model estimations are still robust for detecting differences.

Statistical Analysis:

All experiments were performed ≥3 times in triplicates and data are represented as mean value±SD for statistical comparison. A power of analysis with a 95% confidence interval was used to calculate sample size required to obtain statistically significant results. The sampling number used gave a normal distribution. Significance of differences was assessed by a two tailed student's t-test.

Example 2: hES and hiPS-Derived ECs Generated Using Prior Art Protocols Lack Properties of Cord Blood ECFCs Human endothelial cells have previously been derived from human pluripotent stem cells through co-culture with OP9 stromal cells[22, 25, 30, 31] or through embryoid body (EB) formation[23, 24, 26-29] followed by application of various growth factors and/or receptor signaling pathway inhibitors to promote endothelial cell differentiation.

In the present study, hES or hiPS cells were differentiated in OP9 co-cultures or under EB conditions for 1 week and then expanded cells in endothelial media (FIGS. 1a and 2a, respectively).

Differentiation with OP9 Co-Cultures (FIG. 1):

OP9-co-culture differentiated cells at day 8 exhibited areas of cells with endothelial like morphology (FIG. 1a top panels). Upon isolation and culture in endothelial culture medium, OP9 co-culture differentiated cells initially displayed endothelial cobblestone-like morphology at P1 (FIG. 1a, upper middle panels) and progressively became a heterogeneous population of cells with few cells displaying an endothelial cobblestone morphology by P4 and most cells comprising a fibroblastic-like appearance (FIG. 1a, lower middle panels). The cells at P4 comprised a heterogeneous pattern of CD31, CD144, and CD146 expression, with only a portion of cells expressing each of these antigens (FIG. 1b).). When plated on Matrigel™, OP9-co-cultured cells formed vascular-like networks with a few large branches (FIG. 1c). At P3 or P4, single cells were plated for clonal proliferative potential analysis and the outcomes were scored as single cells that did not divide or divided to form colonies of 2-50 (EC clusters), 51-500 (low proliferative potential EC; LPP-ECFC), 501-2000 (LPP-EC), or ≥2000 cells (high proliferative potential-ECFC; HPP-EC) as previously described[1,2]. The distribution pattern of HPP-EC and LPP-EC colonies formed by OP9 co-cultured hES-derived cloned cells was significantly different to the distribution pattern displayed by CB-ECFC clones (FIG. 1d).

Less than 2% of the ECs derived from OP9 co-cultures cells gave rise to HPP-ECs, in fact, most of the OP9 co-culture derived ECs did not divide or give rise to EC clusters (FIG. 1d). These patterns of EC colony formation were significantly different from the pattern displayed by single ECs derived from CB-ECFCs (FIG. 1d). Expansion of the OP9 co-culture derived ECs was not possible beyond P7 due to replicative senescence (FIG. 1e). Further, ECs at P5 failed to give rise to human blood vessels in vivo upon implantation.

EB-Differentiated Cells (FIG. 2):

KDR$^+$NRP-1$^+$ cells upon isolation and culture in endothelial culture medium displayed a heterogeneous population of cell morphologies, where only a portion of cells displayed endothelial features (FIG. 2a, upper middle panels). Upon further expansion (P4) these cells became predominantly comprised of cells with fibroblastic-like appearance and little endothelial cobblestone morphology (FIG. 2a, lower middle panels). In both hiPS and hES derived EC cells, a heterogeneous pattern of CD31, CD144 and CD146 expression was exhibited with only a portion of the cells expressing each of these antigens (FIG. 2b) and EB-cultured cells formed vascular-like networks with numerous smaller incomplete sprout-like branches (FIG. 2c). At P3 or P4, single cells were plated for clonal proliferative potential analysis and the outcomes were scored as single cells that did not divide or divided to form colonies of 2-50 (EC clusters), 51-500 (low proliferative potential EC; LPP-EC), 501-2000 (LPP-EC), or ≥2000 cells (high proliferative potential-ECFC; HPP-EC) as previously described[1,2]. The distribution pattern of HPP-EC and LPP-EC derived colonies formed by EB-based hES-derived cells was significantly different to the distribution pattern displayed by the CB-ECFC clones. Less than 2% of the ECs derived from EB-derived cells gave rise to HPP-ECs, in fact, most of the EB-derived ECs did not divide or gave rise to EC clusters (FIG. 2d). These patterns of EC colony formation were significantly different from the pattern displayed by single endothelial cells derived from CB-ECFC (FIG. 2d). Expansion of EB-derived endothelial cells was not possible beyond P7 due to replicative senescence (FIG. 2e). Further, endothelial cells at P5 failed to give rise to human blood vessels in vivo upon implantation.

Cells Differentiated in the Presence of an Exogenous TGF-β Inhibitor (FIG. 3):

An alternative 2-step endothelial differentiation protocol that involves initial EB formation followed by 2D adherent cell culture (with added growth factors) was tested to determine whether hES and/or hiPS cells could be used to generate cells with ECFC-like properties. Based upon the known importance of the vascular endothelial growth factor (VEGF) signaling pathway in the emergence of endothelial cells during development[33, 34] and endothelial lineage differentiation of hES cells[23], neuropilin-1 (NRP-1) was used as a marker for identifying emergence of ECFC-like cells. NRP-1 is a VEGF co-receptor and Semaphorin 3A binding multifunctional protein that is expressed in various tissues including endothelial cells, vascular smooth muscle cells and lymphocytes[35]. While the role of NRP-1 in vasculogenesis is unknown, a double knock out of NRP-1 and NRP-2 in mice leads to an embryonic lethal phenotype similar to that of the VEGFR-2 knockout[35, 36] hES (H9 line) and hiPS cell-derived (DF19-9-11T, FCB-iPS-1 and FCB-iPS-2) EBs were generated in suspension culture for 4 days, and seeded them on Matrigel™ coated dishes for 10 days[24] (FIG. 3a,b). This protocol required continuous exposure of the differentiating endothelial cells to TGFβ inhibition starting on day 7 (FIG. 3a). When EBs (FIG. 3b, 2$^{nd}$ panel from left) were attached to Matrigel™ coated plates on day 4, EB-derived cells in 2D culture adhered and grew to form areas of cells with endothelial-like morphology (at days 6 and 9) and became confluent by day 14.

Cells co-expressing NRP-1 and CD31 (NRP-1$^+$CD31$^+$ cells) appeared on day 3 (0.17%) and increased overtime, peaking at day 14 (1.6%) (FIG. 3c). Different subsets of sorted cells were subsequently cultured in endothelial growth (EGM-2) media supplemented with TGF-β inhibitor (10 μM SB431542) for 2 weeks, as TGF-β inhibition has been reported to promote endothelial lineage differentiation from hES or hiPS cells and to prevent the cells from transitioning to a mesenchymal cells[24]. The NRP-1$^+$CD31$^+$ subset gave rise to cells with a characteristic endothelial cobblestone morphology similar to that displayed by CB-ECFCs (FIG. 3d, top panels). While most hES-derived cell subsets formed incomplete capillary-like networks upon plating in Matrigel™, NRP-1$^+$CD31$^+$ cells formed complete structures similar to those exhibited by CB-derived ECFCs (FIG. 3d). The distribution pattern of HPP-EC and LPP-EC colonies formed by NRP-1$^+$CD31$^-$, NRP-1$^-$CD31$^+$ and CD144$^+$CD146$^+$ subsets was significantly different to the pattern displayed by CB-ECFCs (FIG. 3e). However, the distribution pattern of HPP-EC and LPP-EC colonies formed by single NRP-1$^+$CD31$^+$ cells was similar to the pattern displayed by CB-ECFC clones (FIG. 3e). At a clonal level, all of the individual NRP-1$^+$CD31$^+$ plated cells divided and many clones (37%) formed HPP-ECs, while few NRP-1$^+$CD31$^-$ or NRP-1$^-$CD31$^+$ cells formed HPP-ECs (FIG. 3e). Thus, co-expression of NRP-1 and CD31 in hES-derived cells undergoing endothelial differentiation (EB plus 2D protocol) identified a progenitor subset that gave rise to ECs with high clonal proliferative potential and angiogenic activity, but only if cultured in the continual presence of TGF-β inhibition (removal of the TGF-β inhibitor was associated with diminished proliferative potential, loss of endothelial morphology, and increased expression of alpha-smooth muscle actin [α-SMA] as previously described[24]).

In summary, all of the methods tested above failed to facilitate emergence of stable ECs with properties similar to cord blood ECFCs.

Example 3: Protocol for Generating Stable NRP-1$^+$CD31$^+$ ECFC-Like Cells from Both hES and hiPS Cells The inventors sought to develop an endothelial lineage differentiation protocol that facilitates a yield of NRP-1$^+$ CD31$^+$ cells possessing ECFC-like properties, but does not require TGF-β inhibition, the yield being sufficiently large to support expansion of cells into a clinically useful volume of cells.

Figure 4A:
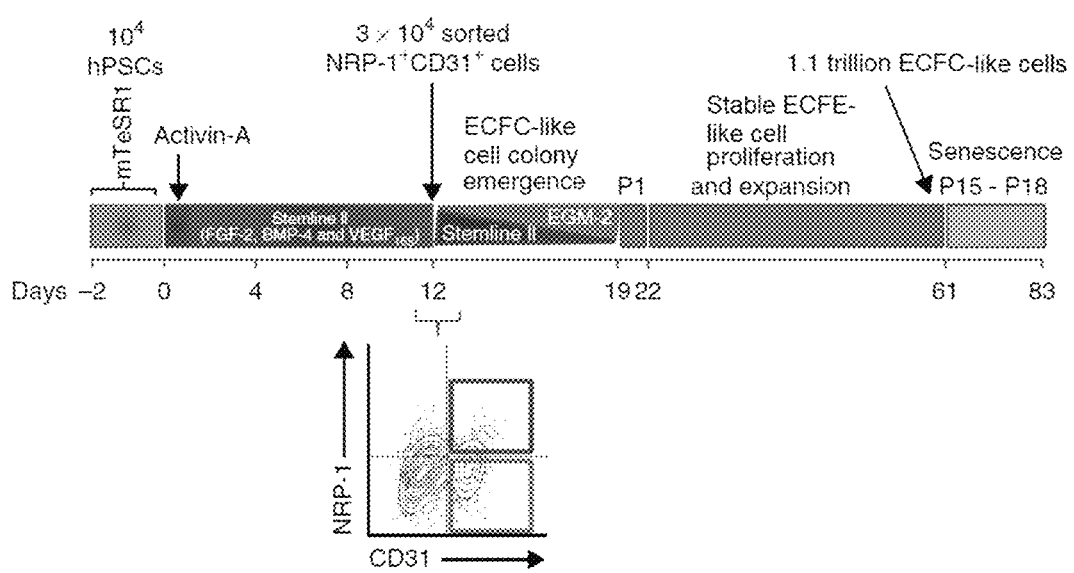
Figure 4B:
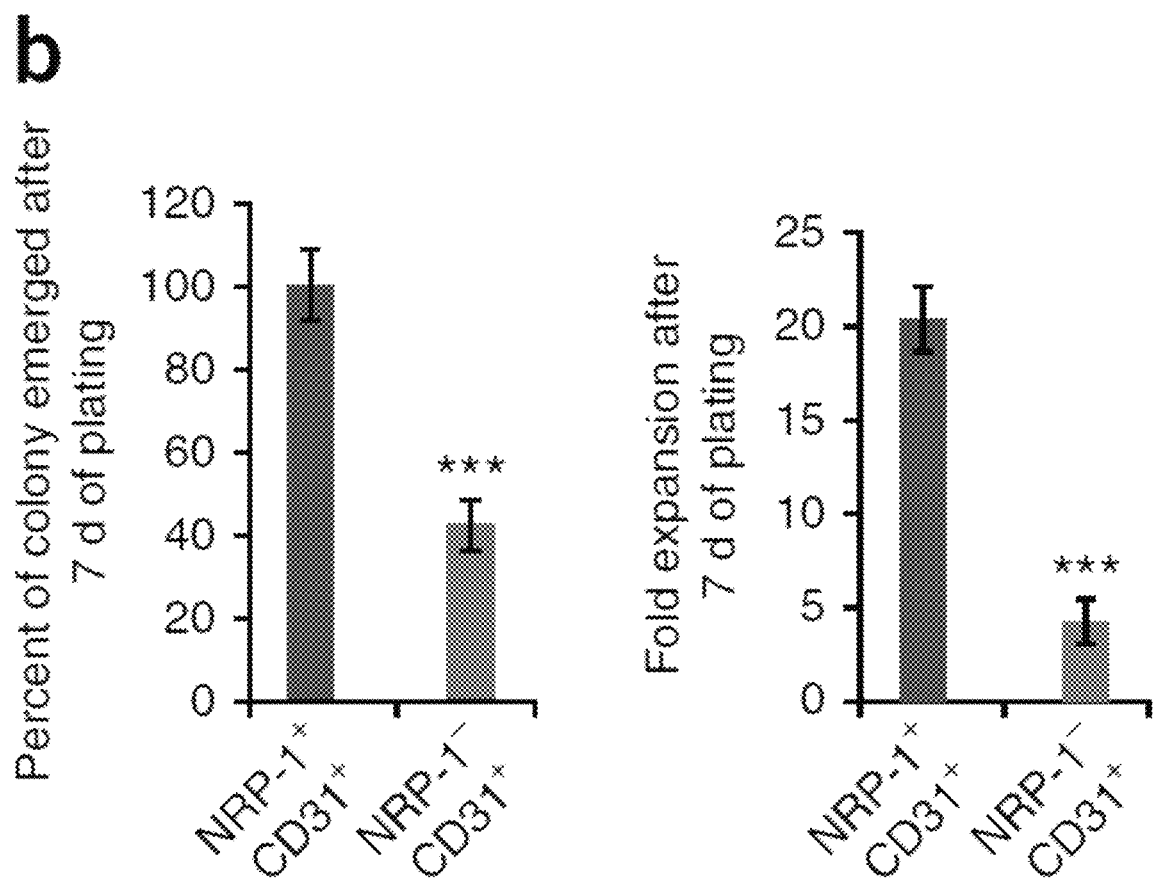
Figure 4F:
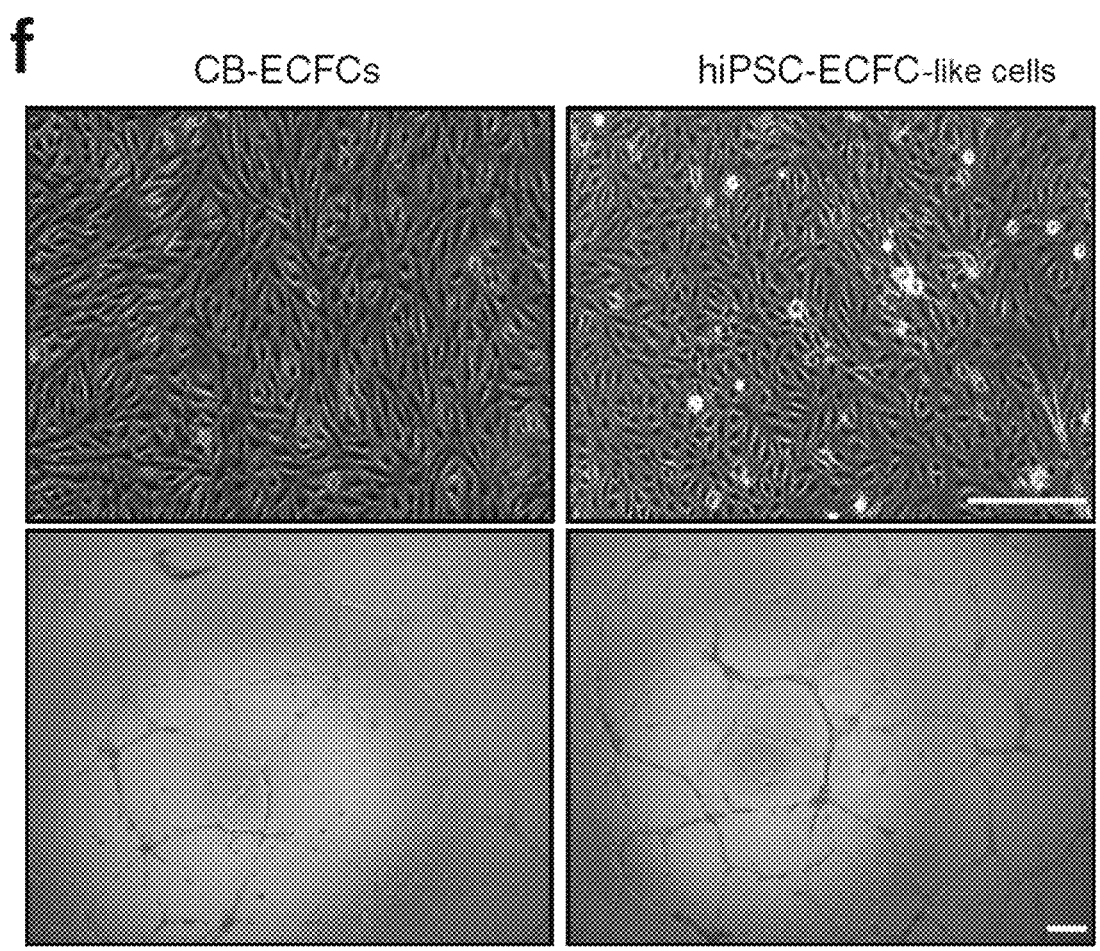

Human pluripotent cells were cultured on Matrigel™-coated plates in mTeSR1 media for two days[37]. To induce endothelial lineage differentiation, mTeSR1 media was replaced with Stemline II media supplemented with 10 ng/mL Activin-A, BMP4, VEGF$_{165}$ and FGF-2 on day 0 of differentiation. The tissue culture media was replaced the following day with fresh Stemline II media supplemented with selected growth factors until day 12 when cultures were analyzed for cells co-expressing CD31 and NRP-1 antigens (FIG. 4a). Using this protocol, it was possible to harvest an average of 4.5% and 2% NRP-1$^+$CD31$^+$ cells from hiPS and hES cells, respectively. NRP-1$^+$CD31$^+$ cells gave rise to 60% more endothelial colonies (FIG. 4B, left panel) and 15 fold more total endothelial cells (FIG. 4B, right panel) compared to NRP-1$^-$CD31$^+$ cells in 7 days culture. NRP-1$^+$CD31$^+$ progeny were homogenous and displayed a cobblestone appearance (FIGS. 4c and 4f), whereas, a heterogeneous cell population was found within the colonies obtained from NRP-1$^-$CD31$^+$ cells (FIG. 6a). A significant (15 fold) increase in total cell number was found in 7 day expansion cultures initiated with NRP-1$^+$CD31$^+$ cells compared to NRP-1$^-$CD31$^+$ cells (FIG. 4b). Further, cells grown from the NRP-1$^+$CD31$^+$ sorted fraction exhibited surface co-expression of CD31 and NRP-1 (FIG. 4d) and uniform expression of CD144, but completely lacked expression of α-SMA (FIG. 4d) in contrast to NRP-1$^-$CD31$^+$ progeny (FIG. 6b). Only 2% of the NRP-1$^+$CD31$^+$ cell subset failed to divide and 48% formed HPP-ECFCs (FIG. 4e and FIG. 6e) with a distribution pattern very similar to cord blood ECFCs (FIG. 4e) but greatly different from the NRP-1$^-$CD31$^+$ subset. Furthermore, when plated on Matrigel™, NRP-1$^+$CD31$^+$ cells formed highly branching capillary-like structures (FIG. 4f) that NRP-1$^-$CD31$^+$ cells did not form when plated on Matrigel™ (FIG. 6d).

Figure 4G:
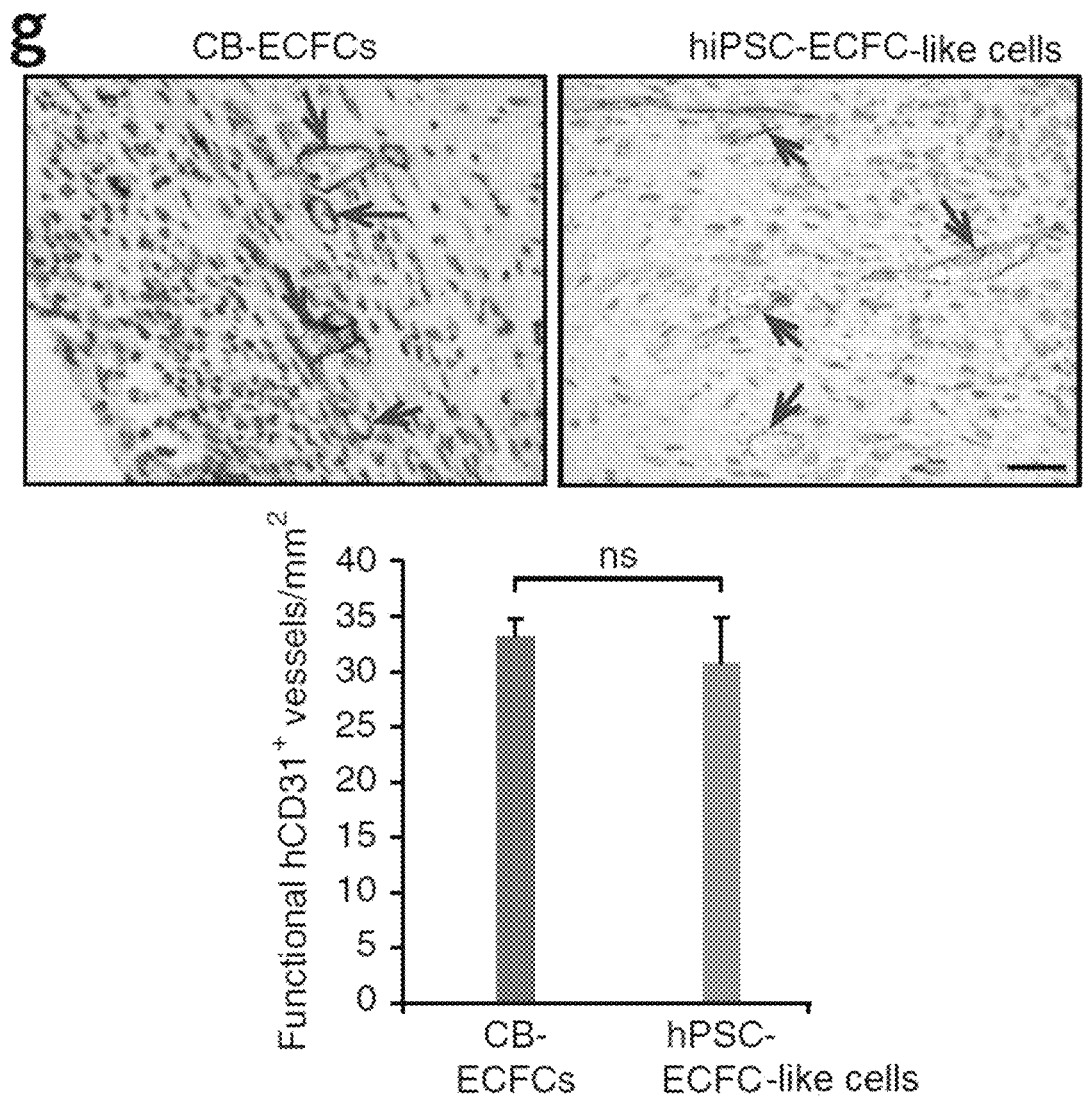

ECFCs (both CB-ECFCs and hiPS-derived ECFC-like cells) disposed in cellularized collagen gels were implanted in immunodeficient (NOD/SCID) mice in a subcutaneous pouch under anaesthesia. Gels were recovered after humanely euthanizing the mice 14 days after implantation. Gels were fixed, permeabilized, and stained with a specific anti-human CD31 antibody that does not cross react with mouse host cells, as previously described[1, 49]. hES and hiPS-derived NRP-1$^+$CD31$^+$ cells produced ECs with robust in vivo vessel forming ability that inosculated with the host murine vessels (FIGS. 4g and f) similar to that of CB-ECFCs previously described[1]. NRP-1$^+$CD31$^+$ cells did not induce teratoma formation after more than 3 months of implantation into immunodeficient mice in more than 24 animals (data not shown). However, NRP-1$^-$CD31$^+$ cells failed to generate functional human blood vessels (FIG. 6c). Collectively, ECFC-like cell protocol day 12-derived NRP-1$^+$CD31$^+$ cells exhibited substantially pure cobblestone morphology, expressed typical endothelial antigens, formed capillary-like networks on Matrigel™ in vitro, exhibited high clonal proliferative potential, and produced robust in vivo human blood vessels filled with host murine red blood cells. Therefore, the day 12 differentiated hES and hiPS derived NRP-1$^+$CD31 cell fraction produced endothelial cells that possess numerous properties similar to CB-ECFCs. Such cells are referred to herein as ECFC-like cells.

Figure 5:
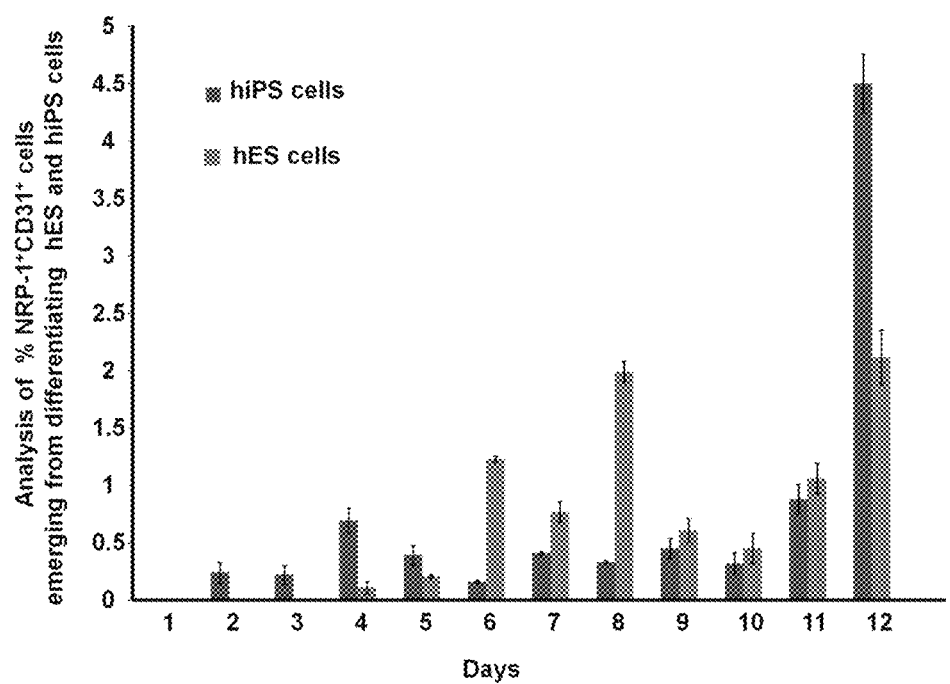
FIG. 5 illustrates kinetic analysis of emergence of NRP-1$^+$CD31$^+$ cells from differentiating hES and hiPS cells in the ECFC-like cell protocol. All experiments were performed 4 times in duplicate; values represent mean±SD.

It was determined that day 1 differentiated hES and hiPS cells did not co-express CD31 and NRP-1 (FIG. 5), but that the percentage of NRP-1$^+$CD31$^+$ cells progressively increased and reached the highest levels at day 12 of culture (FIG. 5; FIG. 7a). Both hES and hiPS cells undergoing ECFC differentiation revealed emergence of cobblestone like morphology at day 9 and day 12 (FIG. 7b and FIGS. 8a and 9a) and colonies of NRP-1$^+$CD31$^+$ cells were observed to emerge among other differentiated cells (FIGS. 8b and 9b). The highest percentage of cells co-expressing CD144 and CD31 appeared from NRP-1$^+$CD31$^+$ cells derived on day 12 (FIG. 7c; FIG. 9d). Day 6-derived cells formed incomplete capillary-like networks upon plating on Matrigel™ (FIG. 9e). Day 9- and day 12-derived cells formed complete capillary-like networks (FIG. 9e). In sum, the NRP-1$^+$CD31$^+$ ECs derived at day 12 gave rise to ECFC-like cells that exhibited the highest frequency of co-expression of the typical endothelial antigens without expression of the mesenchymal antigen α-SMA (FIGS. 8 and 9) and were used for further studies.

Two additional models were used to test the endothelial function of hiPSC-ECFC-like cells in addition to the above subcutaneous implant method. The following three study groups were compared: (i) hiPSC-ECFC-like cells, (ii) hiPSC-embryoid body-derived TGFβ-inhibited CD144$^+$ endothelial cells (hiPSC-EBT-CD144$^+$ ECs) (James et al. 2010) and (iii) CB-ECFCs (Yoder et al. 2007; and Ingram et al. 2004).

Figure 11A:
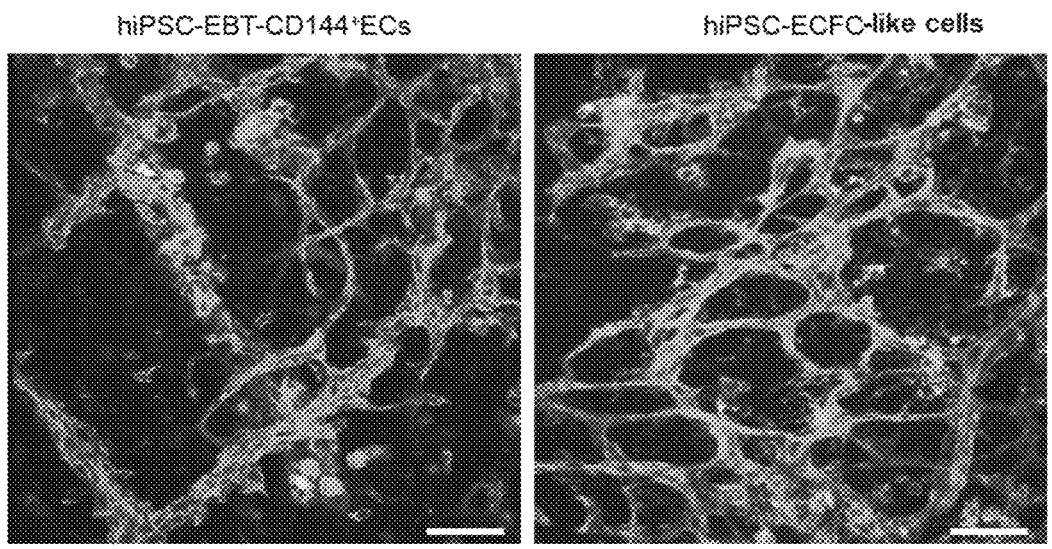
FIGS. 11A-B depict hiPSC-derived ECFC-like cell integration into the ischemic retinal vasculature in vivo.
Figure 11B:
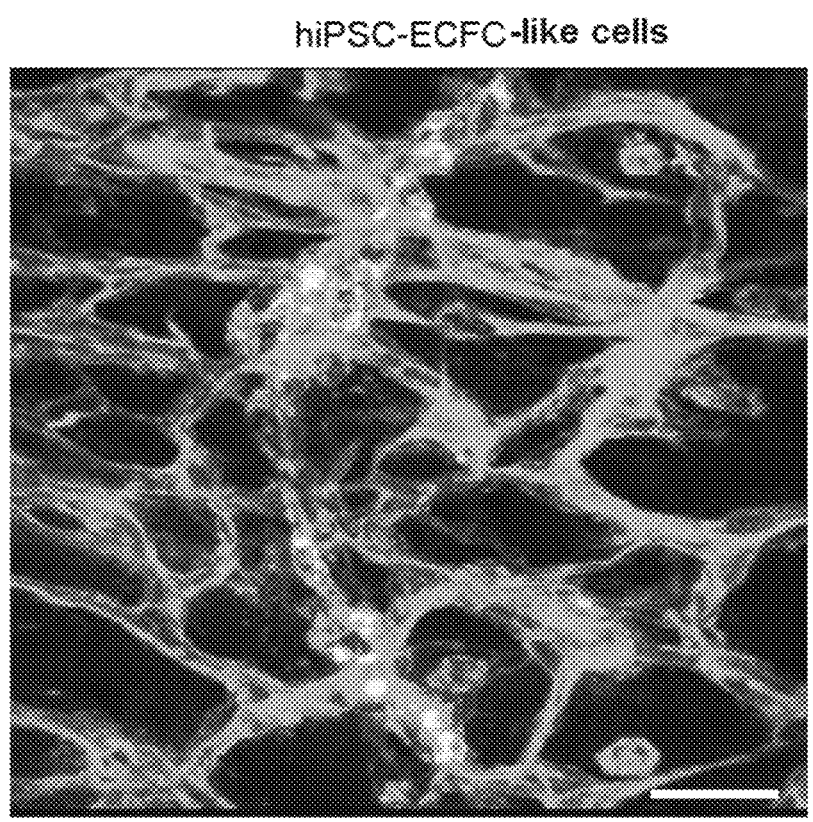

In the first model, rescue of blood vessel formation and reduction of neovascular tufts in newborn mice exposed to high oxygen concentration were measured (Medina et al. 2010). Oxygen-induced retinopathy (OIR) in the neonatal pups results from hypoxia-induced loss of retinal vessels followed by an over-exuberant retinal hypoxic response. A significant reduction of the post-injury avascular area occurred in retinas that received hiPSC-ECFC-like cells (≥36% reduction; P<0.01) but not in retinas that received hiPSC-EBT-CD144$^+$ ECs (≤14% reduction in avascular area; P=not significant (ns)) (FIG. 10a,b). In addition, only hiPSC-ECFC-like cells significantly reduced preretinal neovascular tufts (FIG. 10c; hiPSC-EBT-CD144 EC results not shown). Pre-labeling of the cells with Qdots 655 and imaging at 72 h after cell delivery showed that hiPSC-ECFC-like cells integrated in higher numbers and with wider distribution in host retinal tissue compared with hiPSC-EBT-CD144 ECs (FIG. 11a). The hiPSC-ECFC-like cells, but not the hiPSC-EBT-CD144$^+$ ECs, appeared to form vascular tube structures in the superficial retinal plexus (FIG. 11**b).

A second model of hind limb femoral vessel removal in nude mice was also studied[24]. Salvage of ischemic limbs and blood flow were significantly improved by hiPSC-ECFC-like cells compared with hiPSC-EBT-CD144$^+$ ECs (P<0.05; FIG. 10d-f and data not shown). In these assays, hiPSC-ECFC-like cells functioned similarly to CB-ECFCs.

Primary cells do not proliferate indefinitely but instead undergo senescence after long term in vitro culture[38]. It was possible to expand both hiPS-ECFC-like cells and CB-ECFCs up to P18 without loss of typical endothelial cell features (FIG. 12a,b). Human iPS-ECFC-like cells exhibited a homogenous cobblestone endothelial monolayer similar to that of the CB-ECFC control (FIG. 12a). CB-ECFCs and hiPS-ECFC-like cells were successfully expanded to P18 (FIG. 12b). Only 3% of hiPS-ECFC-like cells exhibited expression of the cell senescence marker 1-galactosidase at P7 and 80% or more cells exhibited replicative senescence by P18, similar to the senescence profile exhibited by the CB-ECFC control cells (FIG. 12c). Importantly, while the majority of hiPS-ECFC-like and CB-ECFCs were senescent and exhibiting characteristics of mortal primary cells[38] at P18, they still maintained an endothelial cobblestone morphology and expression of endothelial antigens CD31, NRP-1 and CD144 but not α-SMA expression (expression for α-SMA was completely absent in these cells; FIG. 12d). Thus, hiPS-derived ECFC-like cells maintained a stable endothelial phenotype throughout long term expansion culture.

Example 4: NRP-1$^+$CD31$^+$ ECFC-Like Cells Display a Molecular Profile that has Similarities and Differences Relative to CB-ECFCs To perform a more complex molecular comparison of the various EC subsets, whole transcriptome sequencing (RNA-seq) analysis was performed to identify and compare molecular profiles of: i) undifferentiated hiPS cells (hiPS-Day 0); ii) day 3-differentiated hiPS cells (hiPS-Day 3); iii) day 12 hiPS-derived NRP-1$^+$CD31$^+$ ECFC-like cells (hiPS-ECFC-like cells); iv) day 12 hES-derived NRP-1$^+$CD31$^+$ ECFC-like cells (hES-ECFC-like cells); and v) CB-ECFCs, as previously described[32].

Figure 13A:
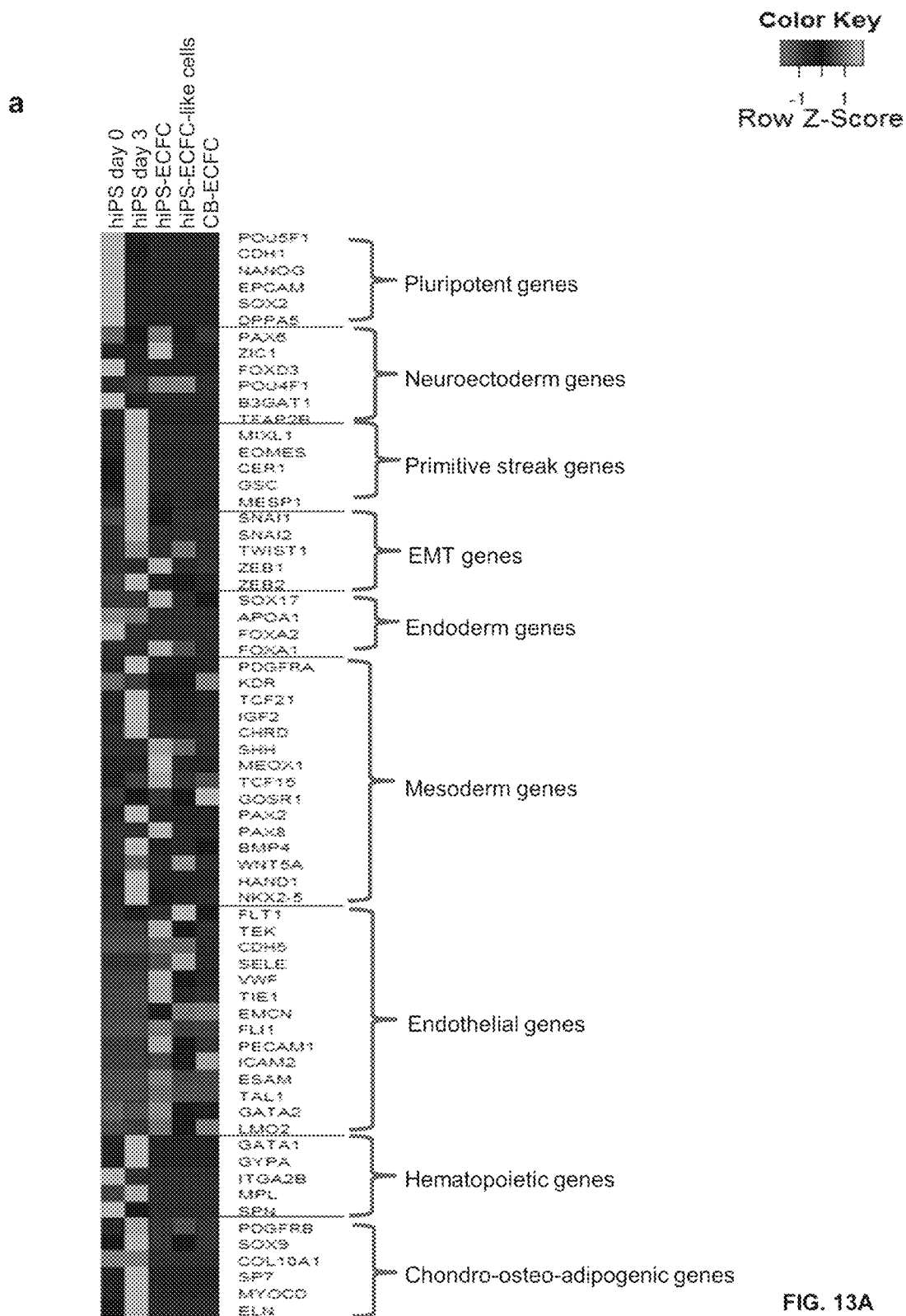
FIGS. 13A-B illustrate that NRP-1$^+$CD31$^+$ ECFC-like cells display molecular signatures similar to CB-ECFCs.
Figure 13B:
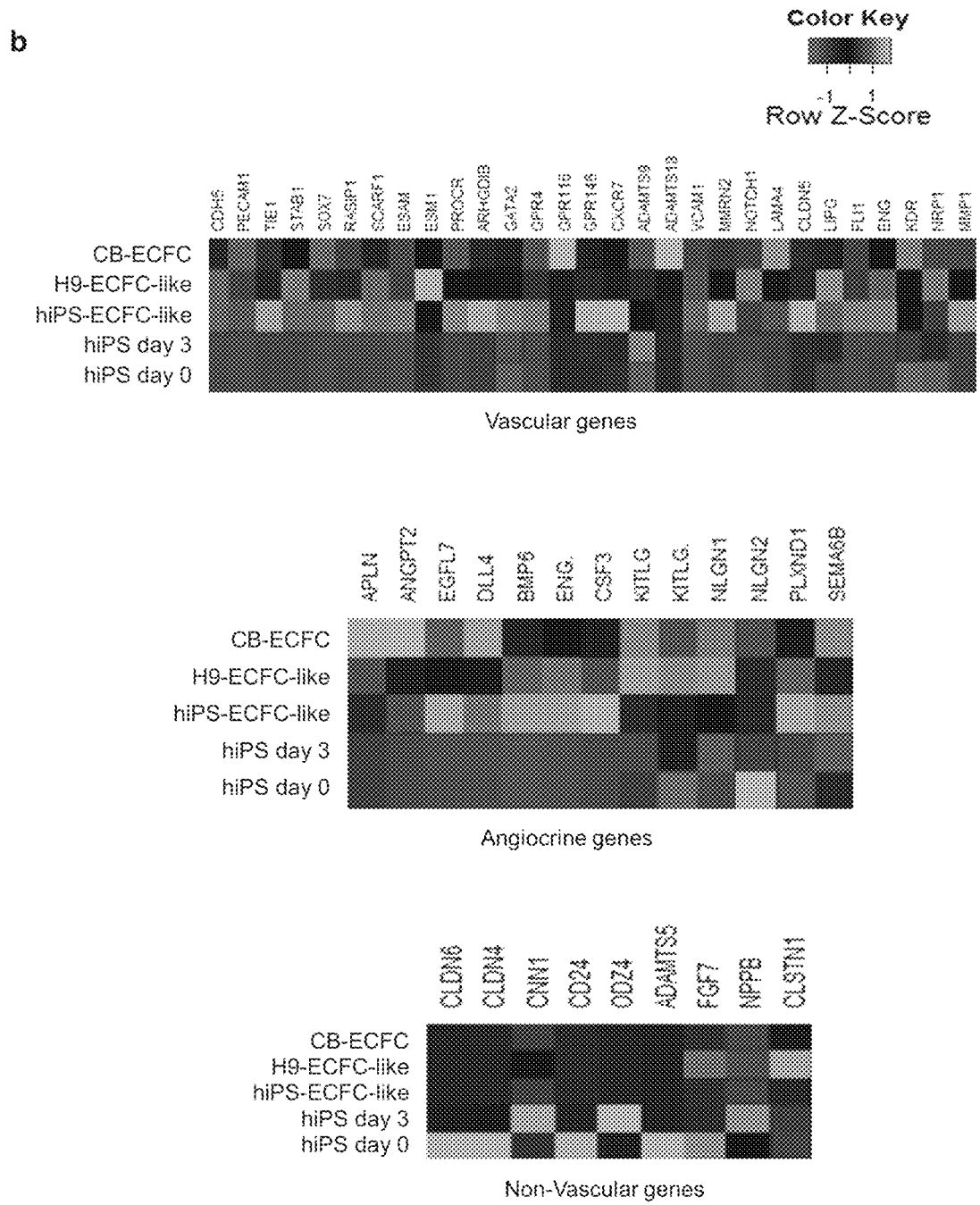
Figure 14E:
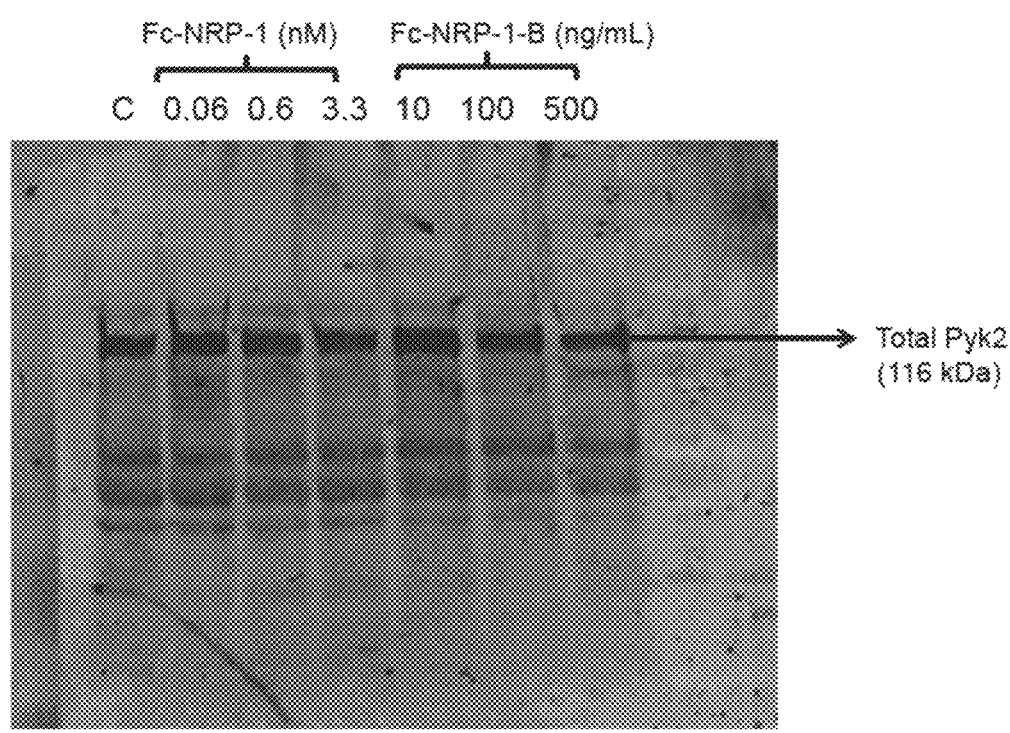

Human iPS-ECFC-like cells and hES-ECFC-like cells exhibited similar relative gene expression profiles to those displayed by CB-ECFCs (FIG. 13a). Human iPS-Day 0 cells displayed a transcriptome profile characteristic of pluripotent cells with limited expression of transcripts typically seen in differentiated cells (FIG. 13a). However, hiPS-Day 3 cells displayed increased expression for multiple lineage specific genes (primitive streak, endoderm, mesoderm, hematopoietic, and chondro-osteo-adipogenic genes), indicating initiation of pluripotent cell differentiation (FIG. 13a). Both hiPS- and hES-derived ECFC-like cells exhibited decreased expression for pluripotent and non-endothelial lineage specific gene transcripts (FIG. 13a) but, increased expression for endothelial gene transcripts (FIGS. 13a and b), similar to CB-ECFCs.

Various differences in transcript expression were also identified in hiPS-derived ECFC-like cells relative to cord blood-derived ECFCs (Table 2). For example, the following genes were overexpressed in hiPS-derived ECFC-like cells relative to cord blood-derived ECFCs: hypothetical protein LOC100132288, CUB and Sushi multiple domains 1, lymphoid-restricted membrane protein, arylacetamide deacetylase (esterase), follistatin-like 5, ENSG00000215262, hypothetical LOC84856, guanylate cyclase activator 2B (uroguanylin), keratin 75, fibroblast activation protein, alpha (FAP), chromosome 22 open reading frame 34, gasdermin C, ENSG00000222954, hydroxysteroid (11-beta) dehydrogenase 1, indoleamine 2,3-dioxygenase 2 and Zic family member 4. The following genes were underexpressed in hiPS derived ECFC-like cells relative to cord blood-derived ECFCs: receptor (chemosensory) transporter protein 4, chromosome X open reading frame 61, acyl-CoA synthetase medium-chain family member 2A, serpin peptidase inhibitor, clade A (alpha-1 antiproteinase, antitrypsin), member 3, ENSG00000218052, chemokine (C—C motif) ligand 23, coiled-coil domain containing 48 and RAS (RAD and GEM)-like GTP-binding 1.

TABLE 2

Transcripts differentially expressed in hiPS ECFC-like cells relative to CB-ECFCs.

| Gene From | To | Gene Name | hiPS-ECFC-1 | hiPS-ECFC-2 | hiPS-ECFC-3 | Avg. expression hiPS-ECFC-like cells | CB-ECFC-1 | CB-ECFC-2 | CB-ECFC-3 | Avg. expression CB-ECFCs |
|---|---|---|---|---|---|---|---|---|---|---|
| ENSG00000136514 | 781730 | receptor (chemosensory) transporter protein 4 | 16 | 12 | 14 | 14 | 128 | 144 | 83 | 118.3333333 |

TABLE 2-continued

Transcripts differentially expressed in hiPS ECFC-like cells relative to CB-ECFCs.

| Gene From | To | Gene Name | hiPS-ECFC-1 | hiPS-ECFC-2 | hiPS-ECFC-3 | Avg. expression hiPS-ECFC-like cells | CB-ECFC-1 | CB-ECFC-2 | CB-ECFC-3 | Avg. expression CB-ECFCs |
|---|---|---|---|---|---|---|---|---|---|---|
| ENSG00000204019 | 817403 | chromosome X open reading frame 61 | 0 | 0 | 0 | 0 | 14 | 6 | 17 | 12.33333333 |
| ENSG00000215750 | 797830 | hypothetical protein LOC100132288 | 17 | 27 | 18 | 20.66666667 | 1 | 3 | 2 | 2 |
| ENSG00000183117 | 805568 | CUB and Sushi multiple domains 1 | 273 | 808 | 593 | 558 | 2 | 8 | 6 | 5.333333333 |
| ENSG00000118308 | 799756 | lymphoid-restricted membrane protein | 5 | 4 | 6 | 5 | 0 | 0 | 0 | 0 |
| ENSG00000066813 | 803346 | acyl-CoA synthetase medium-chain family member 2A | 0 | 0 | 0 | 0 | 5 | 1 | 6 | 4 |
| ENSG00000196136 | 787607 | serpin peptidase inhibitor, clade A (alpha-1 antiproteinase, antitrypsin), member 3 | 2 | 1 | 2 | 1.666666667 | 17 | 12 | 6 | 11.66666667 |
| ENSG00000114771 | 783651 | arylacetamide deacetylase (esterase) | 305 | 142 | 223 | 223.3333333 | 4 | 9 | 1 | 4.666666667 |
| ENSG00000218052 | 816780 | ENSG00000218052 | 4 | 0 | 0 | 1.333333333 | 18 | 15 | 15 | 16 |
| ENSG00000168843 | 802349 | follistatin-like 5 | 76 | 213 | 265 | 184.6666667 | 2 | 7 | 0 | 3 |
| ENSG00000167236 | 820201 | chemokine (C-C motif) ligand 23 | 112 | 31 | 48 | 63.667 | 734 | 728 | 542 | 668 |
| ENSG00000215262 | 778460 | ENSG00000215262 | 6 | 9 | 19 | 11.333 | 0 | 0 | 0 | 0 |
| ENSG00000185904 | 797448 | hypothetical LOC84856 | 615 | 529 | 663 | 602.333 | 187 | 164 | 194 | 181.667 |
| ENSG00000044012 | 818133 | guanylate cyclase activator 2B (uroguanylin) | 58 | 40 | 55 | 51 | 1 | 1 | 0 | 0.667 |
| ENSG00000170454 | 820640 | keratin 75 | 6 | 13 | 5 | 8 | 0 | 0 | 0 | 0 |
| ENSG00000078098 | 775626 | fibroblast activation protein, alpha (FAP) | 217 | 135 | 139 | 163.667 | 4 | 3 | 1 | 2.667 |
| ENSG00000188511 | 800051 | chromosome 22 open reading frame 34 | 343 | 383 | 472 | 399.333 | 134 | 112 | 146 | 130.667 |
| ENSG00000147697 | 790531 | gasdermin C | 254 | 113 | 184 | 183.667 | 51 | 45 | 72 | 56 |
| ENSG00000222954 | 822482 | ENSG00000222954 | 13 | 13 | 12 | 12.667 | 1 | 1 | 3 | 1.667 |
| ENSG00000117594 | 812968 | hydroxysteroid (11-beta) dehydrogenase 1 | 11 | 3 | 8 | 7.333 | 1 | 0 | 0 | 0.333 |
| ENSG00000114654 | 812611 | coiled-coil domain containing 48 | 34 | 47 | 51 | 44 | 151 | 141 | 170 | 154 |
| ENSG0000088320 | 825849 | RAS (RAD and GEM)-like GTP-binding 1 | 59 | 24 | 37 | 40 | 160 | 124 | 91 | 125 |
| ENSG00000188676 | 797469 | indoleamine 2,3-dioxygenase 2 | 21 | 21 | 8 | 16.667 | 0 | 0 | 0 | 0 |
| ENSG00000174963 | 800278 | Zic family member 4 | 18 | 9 | 19 | 15.333 | 0 | 0 | 0 | 0 |

Example 5: NRP-1 Potentiates KDR-Mediated Signaling Essential During ECFC-Like Cells Emergence Although, the role of NRP-1 in cardiovascular development and angiogenesis is well established[35, 36, 39], the mechanism through which NRP-1 functions in ECs is not fully understood. It has been proposed that NRP-1 present on the EC surface binds to $VEGF_{165}$ as a co-receptor and forms signaling complexes with VEGF receptor 2 (KDR)[40]. NRP-1 has a small cytoplasmic domain, which has no defined intrinsic kinase activity. KDR possesses intrinsic kinase activity and formation of NRP-1-$VEGF_{165}$-KDR signaling complexes enhances VEGF-KDR-mediated signaling activity and biological function[40-43]. NRP-1 does not seem to be necessary for mediating $VEGF_{165}$ signaling through KDR[42-44] but, has been clearly shown to be required for maximum KDR activity and/or KDR tyrosine phosphorylation[35, 40-43] and to selectively mediate VEGF-KDR signaling through p130$^{cas}$/Pyk2 activation in endothelial cells[43, 44]. Dimeric Fc-NRP-1, a surrogate for membrane NRP-1[45], and specific monoclonal antibody blocking NRP-1 binding to VEGF (NRP-1-B)[42] have been used to enhance and block NRP-1-mediated activity, respectively. While Fc-NRP-1 acts as proxy for native oligomerized membrane NRP-1[45], NRP-1-B specifically blocks $VEGF_{165}$ binding to NRP-1[42]. Since the data provided herein suggested that Day 6 differentiated hiPS cells exhibited abundant up-regulation in KDR expression but limited NRP-1 expression (insert from FIG. 15b) the inventors hypothesized that augmenting NRP-1 activity might enhance KDR activation. Time and dose response experiments were performed to identify a specific dose (3.3 nM for Fc-NRP-1 dimer and 500 ng/mL for NRP-1-B) and length of time (4 to 6 days) for treatment that consistently gave reproducible results (data not shown and FIG. 15a), as reported[42, 45]. After 4 days of treatment, it was found that a significantly increased generation of NRP-1$^+$CD31$^+$ cells in FC-NRP-1 dimer treated cells (FIG. 15b) and that the blocking antibody NRP-1-B significantly diminished generation of NRP-1$^+$CD31$^+$ cells (FIG. 15b). This effect was further potentiated at day 12 (FIG. 15b).

Referring to FIG. 15 c, in the top blots, hiPS cells undergoing ECFC-like cell differentiation were treated with Fc-control (3.3 nM), Fc-NRP-1 dimer (3.3 nM) or NRP-1-B (500 ng/mL) as described in FIG. 13A. Cells were starved for 5.5 hours and stimulated with $VEGF_{165}$ (30 ng/mL) for 5 min. Cell lysates were subjected to Western blot analysis using antibodies against phospho-KDR and total KDR. Arrows show the expression of phospho-KDR in NRP-1 dimer and NRP-1-B treated hiPS cells. In the bottom panel total KDR levels are depicted in each lane.

KDR phosphorylation was observed in VEGF stimulated groups and Fc-NRP-1 dimer treatment increased phosphorylation of KDR compared to control treated cells. However, decreased phosphorylation was observed in NRP-1-B treated cells (n=3). In the bottom blots, hiPS cells undergoing ECFC-like cell differentiation were treated with the indicated concentration of Fc-control, Fc-NRP-1 dimer or NRP-1-B. Cells were starved and stimulated with $VEGF_{165}$ (30 ng/mL) for 5 mins. Cell lysates were subjected to Western blot analysis using antibodies against phospho-$p130^{Cas}$, phospho-Pyk2 and total Pyk2. Upper panel arrow shows the expression of phospho-$p130^{Cas}$ and the middle panel arrow indicates phospho-Pyk2 expression; the bottom panel indicates total pyk2 in Fc-control (C; 3.3 nM), Fc-NRP-1 dimer and NRP-1-B treated iPS cells. The bottom panel shows total KDR levels in each lane. Increased $P-130^{Cas}$ and Pyk2 phosphorylation was observed in a dose depended manner in the Fc-NRP-1 dimer-treated group compared to control treated cells. However, diminished $P-130^{Cas}$ and Pyk2 phosphorylation was observed in NRP-1-B treated cells compared to control treated cells. We also found increased KDR activation and activation of $p130^{Cas}$, a downstream molecule known to be specifically activated by NRP-1-mediated activation of $KDR^{40,44}$, in Fc-NRP-1 dimer treated cells (FIG. 15c). In contrast, NRP-1-B treated cells displayed decreased KDR phosphorylation and reduced activation of downstream molecules (FIG. 15c). These data suggested that NRP-1 enhances the generation of ECFC-like cells from human pluripotent stem cells by potentiating KDR signaling.

Next, the inventors hypothesized that NRP-1 might also be involved in the maintenance of proliferative potential of cultured ECFC-like cells. It was found that NRP-1 expression was progressively down-regulated in late passage hiPS-ECFC-like cells and was associated with decreased total proliferative potential (FIGS. 16a and b). Analysis for KDR expression in late passage (P14) ECs indicated 40-50% KDR expression (FIG. 16c). However, when cultured in the presence of Fc-NRP-1 for 7 days, P14 ECs displayed significantly increased expansion but decreased 1-galactosidase expression (senescence marker) compared to control and NRP-1-B treated groups (FIGS. 16d-f).

Fc-NRP-1 treated P14 ECs displayed a significant decrease in the percentage of pro-apoptotic cells compared to control treated cells, as seen in late passage (P14) hiPS-ECFC-like cells that were cultured in regular EGM-2 media containing $VEGF_{165}$ and EGM-2 media with $VEGF_{121}$ and treated with control, Fc-NRP-1 and NRP-1-B for 7 days (FIG. 16g). After 7 days, cells were collected, counted and stained with propidium iodide and annexin V to examine for live, proapoptotic, and dead cells in each treatment group. The percentage of proapoptotic cells in $VEGF_{165}$ and $VEGF_{121}$ containing media following 7 days of treatment with control, Fc-NRP-1 and NRP-1-B were significantly decreased in cells cultured in $VEGF_{165}$ containing media compared to cells cultured in the presence of $VEGF_{121}$.

It was confirmed that the effects of Fc-NRP-1 on KDR activation were dependent upon the presence of $VEGF_{165}$, since $VEGF_{121}$ failed to promote interaction between Fc-NRP-1 and KDR bearing P14 ECFC-like cells (FIGS. 16g-i). Thus, Fc-NRP-1 activation of KDR via $VEGF_{165}$ plays a role in the rescue of proliferation and diminished expression of senescent markers and pro-apoptotic behavior in near senescent hiPS-derived ECFC-like cells.

In preliminary studies, it was determined that primary ECs derived from patients with PAD and CLI exhibit low levels of NRP-1 expression, possess low clonal proliferative potential, exhibit markers of senescence and do not form robust in vivo human vessels upon implantation in immunodeficient mice (FIGS. 17a-g). However, Fc-NRP-1 treatment facilitated proliferation, survival, and modestly diminished evidence of senescence in circulating and resident arterial-derived endothelial cells isolated from patients with PAD and CLI (FIGS. 17h-n). Thus, Fc-NRP-1 treatment of late passage near senescent hiPS-ECFC-like cells and patient-derived PAD-ECs increases proliferative potential, decreases apoptosis, and diminishes markers of senescence in a $VEGF_{165}$ dependent fashion.

Example 6: Discussion

In the above Examples, a method for reproducibly deriving and isolate a substantially pure and stable population of ECs possessing umbilical cord blood ECFC-like properties, referred to herein as ECFC-like cells, has been provided and tested.

Figure 18:
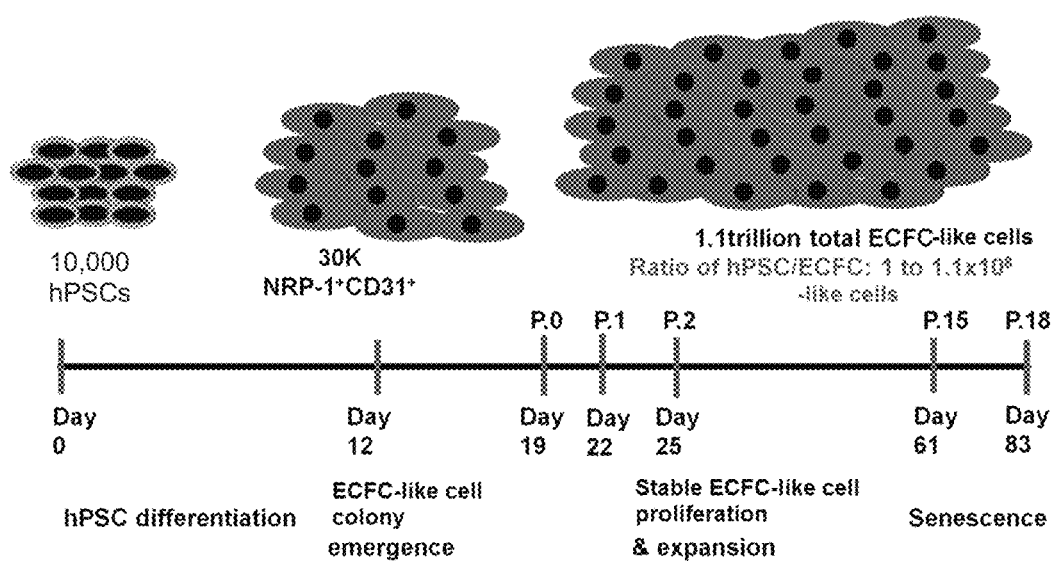
FIG. 18 is a schematic representation showing an estimated generation of over a trillion cells in 83 days, starting from $10^4$ hES or hiPS cells using the ECFC-like cell differentiation protocol of the present disclosure. Day 12 derived NRP-1$^+$CD31$^+$ cells gave rise to stable ECFC-like cell colonies that underwent extensive expansion to give rise to more than a trillion cells. This study was performed with 1 hES line and 3 hiPS lines on two occasions.

ECFC-like cells have properties similar to CB-ECFCs: $NRP-1^+CD31^+$ cells formed a homogenous monolayer with a characteristic cobblestone appearance, exhibited high clonal proliferative potential, demonstrated angiogenic behavior by forming complete capillary like structures when cultured on Matrigel™, and formed robust in vivo inosculated vessels when implanted in immune deficient mice in the absence of co-implantation cells. These human pluripotent stem cell-derived ECFC-like cells were stable and did not transition to non-endothelial cells over prolonged culture (18 passages) and could be expanded to over a trillion ECs in less than 3 months from a single starting pluripotent cell (FIG. 18). Unlike primary CB-ECFCs, the ECFC-like cells provided herein exhibit stable ECFC characteristics and have the potential to be expanded into a volume of cells that are suitable for use in various clinical applications. Further, the ECFC-like cells provided herein may be patient-specific, for example, if they are derived from iPSCs from the patient.

ECFC-like cells have properties different from ECs generated in vitro using known protocols: The highly efficient output of functional ECs from ECFC-like cells (i.e., over one trillion ECs in less than three months) contrasts with reported yields of $0.6^{22}$, $7.4^{24}$ and $11.6^{46}$ ECs derived from hPSCs using other published protocols. Further, ECs derived from hPSCs using other published protocols do not have a capacity to form blood vessels when implanted in vivo in the absence of co-implantation cells It was found that NRP-1-$VEGF_{165}$-KDR-mediated activation of KDR and its downstream signaling molecules is a mechanism for the emergence and derivation of ECFC-like cells from hPSCs, and for enhancing survival and proliferative potential of late passage, near senescent hPSC-derived ECFC-like cells and patient-derived near senescent ECFCs. The results provided herein suggest it is feasible to consider use of patient-derived ECFC-like cells as a therapy for treating patients with cardiovascular disease.

Although the disclosure has been described with reference to certain specific embodiments, various modifications thereof will be apparent to those skilled in the art without departing from the purpose and scope of the disclosure as outlined in the claims appended hereto. Any examples provided herein are included solely for the purpose of illustrating the disclosure and are not intended to limit the disclosure in any way. Any drawings provided herein are solely for the purpose of illustrating various aspects of the disclosure and are not intended to be drawn to scale or to limit the disclosure in any way. The disclosures of all prior art recited herein are incorporated herein by reference in their entirety.

REFERENCE LIST

1. Yoder, M. C. et al. Redefining endothelial progenitor cells via clonal analysis and hematopoietic stem/progenitor cell principals. *Blood* 109, 1801-1809 (2007).
2. Ingram, D. A. et al. Vessel wall-derived endothelial cells rapidly proliferate because they contain a complete hierarchy of endothelial progenitor cells. *Blood* 105, 2783-2786 (2005).
3. Ingram, D. A. et al. Identification of a novel hierarchy of endothelial progenitor cells using human peripheral and umbilical cord blood. *Blood* 104, 2752-2760 (2004).
4. Critser, P. J., Kreger, S. T., Voytik-Harbin, S. L. & Yoder, M. C. Collagen matrix physical properties modulate endothelial colony forming cell-derived vessels in vivo. *Microvasc Res* 80, 23-30 (2010).
5. Au, P. et al. Differential in vivo potential of endothelial progenitor cells from human umbilical cord blood and adult peripheral blood to form functional long-lasting vessels. *Blood* 111, 1302-1305 (2008).
6. Melero-Martin, J. M. et al. Engineering robust and functional vascular networks in vivo with human adult and cord blood-derived progenitor cells. *Circ Res* 103, 194-202 (2008).
7. Lin, Y., Weisdorf, D. J., Solovey, A. & Hebbel, R. P. Origins of circulating endothelial cells and endothelial outgrowth from blood. *J Clin Invest* 105, 71-77 (2000).
8. Ikpeazu, C., Davidson, M. K., Halteman, D., Browning, P. J. & Brandt, S. J. Donor origin of circulating endothelial progenitors after allogeneic bone marrow transplantation. *Biol Blood Marrow Transplant* 6, 301-308 (2000).
9. Moubarik, C. et al. Transplanted late outgrowth endothelial progenitor cells as cell therapy product for stroke. *Stem Cell Rev* 7, 208-220 (2011).
10. Schwarz, T. M. et al. Vascular incorporation of endothelial colony-forming cells is essential for functional recovery of murine ischemic tissue following cell therapy. *Arterioscler Thromb Vasc Biol* 32, e13-21 (2012).
11. Saif, J. et al. Combination of injectable multiple growth factor-releasing scaffolds and cell therapy as an advanced modality to enhance tissue neovascularization. *Arterioscler Thromb Vasc Biol* 30, 1897-1904 (2010).
12. Dubois, C. et al. Differential effects of progenitor cell populations on left ventricular remodeling and myocardial neovascularization after myocardial infarction. *J Am Coll Cardiol* 55, 2232-2243 (2010).
13. Schuh, A. et al. Transplantation of endothelial progenitor cells improves neovascularization and left ventricular function after myocardial infarction in a rat model. *Basic Res Cardiol* 103, 69-77 (2008).
14. Stitt, A. W. et al. Vascular stem cells and ischaemic retinopathies. *Prog Retin Eye Res* 30, 149-166 (2011).
15. Medina, R. J., O'Neill, C. L., Humphreys, M. W., Gardiner, T. A. & Stitt, A. W. Outgrowth endothelial cells: characterization and their potential for reversing ischemic retinopathy. *Invest Ophthalmol Vis Sci* 51, 5906-5913 (2010).
16. Bouvard, C. et al. alpha6-integrin subunit plays a major role in the proangiogenic properties of endothelial progenitor cells. *Arterioscler Thromb Vasc Biol* 30, 1569-1575 (2010).
17. Lee, J. H., Lee, S. H., Yoo, S. Y., Asahara, T. & Kwon, S. M. CD34 Hybrid Cells Promote Endothelial Colony-Forming Cell Bioactivity and Therapeutic Potential for Ischemic Diseases. *Arterioscler Thromb Vasc Biol* (2013).
18. Stroncek, J. D., Ren, L. C., Klitzman, B. & Reichert, W. M. Patient-derived endothelial progenitor cells improve vascular graft patency in a rodent model. *Acta Biomater* 8, 201-208 (2012).
19. Robbins, R. D., Prasain, N., Maier, B. F., Yoder, M. C. & Mirmira, R. G. Inducible pluripotent stem cells: not quite ready for prime time? *Curr Opin Organ Transplant* 15, 61-67 (2010).
20. Broxmeyer, H. E. et al. Hematopoietic stem/progenitor cells, generation of induced pluripotent stem cells, and isolation of endothelial progenitors from 21- to 23.5-year cryopreserved cord blood. *Blood* 117, 4773-4777 (2011).
21. Lee, M. R. et al. Epigenetic regulation of NANOG by miR-302 cluster-MBD2 completes induced pluripotent stem cell reprogramming. *Stem Cells* 31, 666-681 (2012).
22. Choi, K. D. et al. Hematopoietic and endothelial differentiation of human induced pluripotent stem cells. *Stem Cells* 27, 559-567 (2009).
23. Cimato, T. et al. Neuropilin-1 identifies endothelial precursors in human and murine embryonic stem cells before CD34 expression. *Circulation* 119, 2170-2178 (2009).
24. James, D. et al. Expansion and maintenance of human embryonic stem cell-derived endothelial cells by TGFbeta inhibition is Id1 dependent. *Nat Biotechnol* (2010).
25. Taura, D. et al. Induction and isolation of vascular cells from human induced pluripotent stem cells—brief report. *Arterioscler Thromb Vasc Biol* 29, 1100-1103 (2009).
26. Goldman, O. et al. A boost of BMP4 accelerates the commitment of human embryonic stem cells to the endothelial lineage. *Stem Cells* 27, 1750-1759 (2009).
27. Feng, Q. et al. Hemangioblastic derivatives from human induced pluripotent stem cells exhibit limited expansion and early senescence. *Stem Cells* 28, 704-712 (2010).
28. Rufaihah, A. J. et al. Endothelial cells derived from human iPSCS increase capillary density and improve perfusion in a mouse model of peripheral arterial disease. *Arterioscler Thromb Vasc Biol* 31, e72-79 (2011).
29. Nourse, M. B. et al. VEGF induces differentiation of functional endothelium from human embryonic stem cells: implications for tissue engineering. *Arterioscler Thromb Vasc Biol* 30, 80-89 (2010).
30. Sone, M. et al. Pathway for differentiation of human embryonic stem cells to vascular cell components and their potential for vascular regeneration. *Arterioscler Thromb Vasc Biol* 27, 2127-2134 (2007).
31. Vodyanik, M. A., Bork, J. A., Thomson, J. A. & Slukvin, II Human embryonic stem cell-derived CD34+ cells: efficient production in the coculture with OP9 stromal cells and analysis of lymphohematopoietic potential. *Blood* 105, 617-626 (2005).
32. Ginsberg, M. et al. Efficient direct reprogramming of mature amniotic cells into endothelial cells by ETS factors and TGFbeta suppression. *Cell* 151, 559-575 (2012).
33. Carmeliet, P. et al. Abnormal blood vessel development and lethality in embryos lacking a single VEGF allele. *Nature* 380, 435-439 (1996).

34. Gerber, H. P. et al. VEGF is required for growth and survival in neonatal mice. *Development* 126, 1149-1159 (1999).
35. Staton, C. A., Kumar, I., Reed, M. W. & Brown, N. J. Neuropilins in physiological and pathological angiogenesis. *J Pathol* 212, 237-248 (2007).
36. Takashima, S. et al. Targeting of both mouse neuropilin-1 and neuropilin-2 genes severely impairs developmental yolk sac and embryonic angiogenesis. *Proc Natl Acad Sci USA* 99, 3657-3662 (2002).
37. Evseenko, D. et al. Mapping the first stages of mesoderm commitment during differentiation of human embryonic stem cells. *Proc Natl Acad Sci USA* 107, 13742-13747 (2010).
38. Kuilman, T., Michaloglou, C., Mooi, W. J. & Peeper, D. S. The essence of senescence. *Genes Dev* 24, 2463-2479 (2010).
39. Kitsukawa, T., Shimono, A., Kawakami, A., Kondoh, H. & Fujisawa, H.
Overexpression of a membrane protein, neuropilin, in chimeric mice causes anomalies in the cardiovascular system, nervous system and limbs. *Development* 121, 4309-4318 (1995).
40. Zachary, I. C. How neuropilin-1 regulates receptor tyrosine kinase signalling: the knowns and known unknowns. *Biochem Soc Trans* 39, 1583-1591 (2011).
41. Soker, S., Miao, H. Q., Nomi, M., Takashima, S. & Klagsbrun, M. VEGF165 mediates formation of complexes containing VEGFR-2 and neuropilin-1 that enhance VEGF165-receptor binding. *J Cell Biochem* 85, 357-368 (2002).
42. Pan, Q. et al. Blocking neuropilin-1 function has an additive effect with anti-VEGF to inhibit tumor growth. *Cancer Cell* 11, 53-67 (2007).
43. Herzog, B., Pellet-Many, C., Britton, G., Hartzoulakis, B. & Zachary, I. C.
VEGF binding to NRP1 is essential for VEGF stimulation of endothelial cell migration, complex formation between NRP1 and VEGFR2, and signaling via FAK Tyr407 phosphorylation. *Mol Biol Cell* 22, 2766-2776 (2011).
44. Evans, I. M. et al. Neuropilin-1 signaling through p130Cas tyrosine phosphorylation is essential for growth factor-dependent migration of glioma and endothelial cells. *Mol Cell Biol* 31, 1174-1185 (2011).
45. Uniewicz, K. A., Cross, M. J. & Fernig, D. G. Exogenous recombinant dimeric neuropilin-1 is sufficient to drive angiogenesis. *J Biol Chem* 286, 12-23 (2011).
46. Lippmann, E. S. et al. Derivation of blood-brain barrier endothelial cells from human pluripotent stem cells. *Nat Biotechnol* 30, 783-791 (2012).
47. Thomson, J. A. et al. Embryonic stem cell lines derived from human blastocysts. *Science* 282, 1145-1147 (1998).
48. Yu, J. et al. Human induced pluripotent stem cells free of vector and transgene sequences. *Science* 324, 797-801 (2009).
49. Prasain, N., Meador, J. L. & Yoder, M. C. Phenotypic and functional characterization of endothelial colony forming cells derived from human umbilical cord blood. *J Vis Exp* (2012).
50. Bailey, J. L. et al. Collagen oligomers modulate physical and biological properties of three-dimensional self-assembled matrices. *Biopolymers* 95, 77-93 (2011).
51. Samuel et al. Generation of functionally competent and durable engineered blood vessels from human induced pluripotent cells. *PNAS* Early Edition 1310675110.

We claim:

1. A method for generating an isolated population of endothelial colony forming cell-like cells (ECFC-like cells) from pluripotent stem cells, the method comprising:
contacting pluripotent stem cells with a first endothelial differentiation medium comprising Activin A, bone morphogenetic protein-4 (BMP-4), vascular endothelial growth factor (VEGF) and fibroblast growth factor-2 (FGF-2);
culturing the pluripotent stem cells for about 24 hours in the first endothelial differentiation medium;
contacting the pluripotent stem cells with a second endothelial differentiation medium comprising BMP-4, VEGF and FGF-2, wherein the second endothelial differentiation medium does not include Activin A;
isolating ECFC-like cells that are $CD31^+NRP-1^+$;
wherein the pluripotent stem cells are cultured in the absence of co-culture cells, embryoid body formation, and/or exogenous inhibition of transforming growth factor-β (TGF-β).

2. The method of claim 1, wherein the isolated ECFC-like cells are further characterized by one or more of CD144+, KDR+ and a-SMA-expression.

3. The method of claim 1, wherein the first endothelial differentiation medium comprises about 5-25 ng/mL Activin A, about 5-25 ng/mL BMP-4 and about 5-25 ng/mL FGF-2.

4. The method of claim 1, wherein the first endothelial differentiation medium or the second endothelial differentiation medium comprises 5-50 ng/mL VEGF.

5. The method of claim 1, wherein the ECFC-like cells are isolated on day 10, 11 or 12 after contacting pluripotent stem cells with the first endothelial differentiation medium.

6. The method of claim 5, wherein the ECFC-like cells are isolated on day 12 after contacting pluripotent stem cells with the first endothelial differentiation medium.

7. The method of claim 1, wherein the ECFC-like cells are isolated by flow cytometry or magnetic activated cell sorting.

8. The method of claim 1, wherein the isolated ECFC-like cells forms blood vessels when implanted into a mammal in the absence of co-implanted cells.

9. The method of claim 1, wherein at least about 95% of the ECFC-like cells in the isolated population of ECFC-like cells proliferate.

10. The method of claim 1, wherein at least about 35-50% of the ECFCs in the isolated population of ECFC-like cells are high proliferative potential (HPP) ECFC-like cells.

11. The method of claim 10, wherein the HPP ECFC-like cells produces at least about 2001 cells per starting cell.

12. The method of claim 10, wherein the HPP-ECFC-like cells self-replenish.

13. The method of claim 1, further comprising:
expanding the isolated ECFC-like cells in a composition comprising endothelium growth medium.

14. The method of claim 13, further comprising:
passaging the expanded ECFC-like cells up to 18 times.

15. The method of claim 13, wherein the isolated cells are expanded into a population of at least about one trillion cells in less than about three months.

* * * * *